(12) United States Patent
Neufeld et al.

(10) Patent No.: US 8,815,823 B2
(45) Date of Patent: Aug. 26, 2014

(54) PHARMACEUTICAL COMPOSITIONS AND METHODS USEFUL FOR MODULATING ANGIOGENESIS, INHIBITING METASTASIS AND TUMOR FIBROSIS, AND ASSESSING THE MALIGNANCY OF COLON CANCER TUMORS

(75) Inventors: Gera Neufeld, Haifa (IL); Gal Akiri, Haifa (IL); Zahava Vadasz, Haifa (IL); Stela Gengrinovitch, Merom Galil (IL)

(73) Assignee: Technion Research & Development Foundation Ltd. (IL)

( * ) Notice: Subject to any disclaimer, the term of this patent is extended or adjusted under 35 U.S.C. 154(b) by 232 days.

(21) Appl. No.: 13/416,976

(22) Filed: Mar. 9, 2012

(65) Prior Publication Data

US 2012/0165398 A1 Jun. 28, 2012

Related U.S. Application Data

(62) Division of application No. 12/571,167, filed on Sep. 30, 2009, now Pat. No. 8,168,180, which is a division of application No. 10/536,440, filed as application No. PCT/IL03/01008 on Nov. 27, 2003, now Pat. No. 8,163,494.

(51) Int. Cl.
*C07H 21/04* (2006.01)
*C12N 15/11* (2006.01)

(52) U.S. Cl.
USPC ........................ 514/44 A; 536/24.5

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,485,088 A | 11/1984 | Chvapil |
| 4,545,382 A | 10/1985 | Higgins et al. |
| 4,637,403 A | 1/1987 | Garcia et al. |
| 4,666,828 A | 5/1987 | Gusella |
| 4,683,202 A | 7/1987 | Mullis |
| 4,731,374 A | 3/1988 | Griss et al. |
| 4,748,116 A | 5/1988 | Simonsson et al. |
| 4,801,531 A | 1/1989 | Frossard |
| 4,816,567 A | 3/1989 | Cabilly et al. |
| 4,843,086 A | 6/1989 | Griss et al. |
| 4,879,219 A | 11/1989 | Wands et al. |
| 4,886,812 A | 12/1989 | Griss et al. |
| 4,943,593 A | 7/1990 | Palfreyman et al. |
| 4,946,778 A | 8/1990 | Ladner et al. |
| 4,965,288 A | 10/1990 | Palfreyman et al. |
| 4,997,854 A | 3/1991 | Kagan et al. |
| 5,011,771 A | 4/1991 | Bellet et al. |
| 5,021,404 A | 6/1991 | Folkman et al. |
| 5,021,456 A | 6/1991 | Palfreyman et al. |
| 5,059,714 A | 10/1991 | Palfreyman et al. |
| 5,120,764 A | 6/1992 | McCarthy et al. |
| 5,182,297 A | 1/1993 | Palfreyman et al. |
| 5,192,659 A | 3/1993 | Simons |
| 5,252,608 A | 10/1993 | Palfreyman et al. |
| 5,262,035 A | 11/1993 | Gregg et al. |
| 5,272,057 A | 12/1993 | Smulson et al. |
| 5,281,521 A | 1/1994 | Trojanowski et al. |
| 5,545,806 A | 8/1996 | Lonberg et al. |
| 5,545,807 A | 8/1996 | Surani et al. |
| 5,625,126 A | 4/1997 | Lonberg et al. |
| 5,633,425 A | 5/1997 | Lonberg et al. |
| 5,641,484 A | 6/1997 | Hung et al. |
| 5,661,016 A | 8/1997 | Lonberg et al. |
| 5,721,138 A | 2/1998 | Lawn |
| 6,015,562 A | 1/2000 | Hinman et al. |
| 6,140,056 A | 10/2000 | Khodadoust |
| 6,225,118 B1 | 5/2001 | Grant et al. |
| 6,277,622 B1 | 8/2001 | Weiss |
| 6,300,092 B1 * | 10/2001 | Khodadoust et al. ............. 506/9 |
| 6,303,318 B1 | 10/2001 | O'Brien |
| 6,316,416 B1 | 11/2001 | Patierno et al. |
| 6,326,174 B1 | 12/2001 | Joyce et al. |
| 6,391,602 B1 | 5/2002 | Khodadoust |
| 6,534,261 B1 | 3/2003 | Cox, III et al. |
| 6,808,707 B2 | 10/2004 | Ensley |
| 7,112,668 B2 | 9/2006 | Rastelli et al. |
| 7,208,300 B2 | 4/2007 | Evans et al. |
| 7,255,856 B2 | 8/2007 | Li et al. |
| 7,255,857 B2 | 8/2007 | Li et al. |
| 7,335,294 B2 | 2/2008 | Heller et al. |
| 7,348,170 B2 | 3/2008 | Yuuki et al. |

(Continued)

FOREIGN PATENT DOCUMENTS

| | | |
|---|---|---|
| EP | 0186087 | 8/1989 |
| EP | 0375408 | 6/1990 |

(Continued)

OTHER PUBLICATIONS

Behlke et al (Integrated DNA Technologies (2005)).*

(Continued)

*Primary Examiner* — Richard Schnizer
(74) *Attorney, Agent, or Firm* — Cooley LLP

(57) ABSTRACT

Methods and compositions suitable for modulating angiogenesis in a mammalian tissue are provided. Further provided are methods suitable for inhibiting metastasis and fibrosis in a mammalian tissue and for assessing the malignancy of colon cancer tumors.

19 Claims, 19 Drawing Sheets

(56) References Cited

U.S. PATENT DOCUMENTS

| | | |
|---|---|---|
| 7,396,920 B2 | 7/2008 | Hemmings et al. |
| 7,445,920 B2 | 11/2008 | Evans et al. |
| 7,585,634 B2 | 9/2009 | Kim et al. |
| 8,163,494 B2 | 4/2012 | Neufeld et al. |
| 8,168,180 B2 | 5/2012 | Neufeld et al. |
| 8,461,303 B2 | 6/2013 | Smith et al. |
| 2001/0005581 A1 | 6/2001 | Grant et al. |
| 2001/0012890 A1 | 8/2001 | Thompson |
| 2002/0072089 A1 | 6/2002 | Holtzman et al. |
| 2002/0123476 A1 | 9/2002 | Emanuele et al. |
| 2002/0128218 A1 | 9/2002 | Emanuele et al. |
| 2002/0151007 A1 | 10/2002 | Khodadoust et al. |
| 2002/0156263 A1 | 10/2002 | Chen |
| 2003/0008023 A1 | 1/2003 | Lu |
| 2003/0017068 A1 | 1/2003 | Larrain et al. |
| 2003/0092037 A1 | 5/2003 | Matsuzaki et al. |
| 2003/0096980 A1 | 5/2003 | Froehler et al. |
| 2003/0099213 A1 | 5/2003 | Lee et al. |
| 2003/0114410 A1 | 6/2003 | Neufeld et al. |
| 2003/0129672 A1 | 7/2003 | Dyer et al. |
| 2003/0149997 A1 | 8/2003 | Hageman |
| 2003/0152926 A1 | 8/2003 | Murray et al. |
| 2003/0211076 A1 | 11/2003 | Li |
| 2004/0009154 A1 | 1/2004 | Khan et al. |
| 2004/0029114 A1 | 2/2004 | Mack et al. |
| 2004/0156854 A1 | 8/2004 | Mulligan et al. |
| 2004/0171110 A1 | 9/2004 | Evans et al. |
| 2004/0176296 A1 | 9/2004 | Holtzman et al. |
| 2004/0197328 A1 | 10/2004 | Young et al. |
| 2004/0213756 A1 | 10/2004 | Michael et al. |
| 2004/0248871 A1 | 12/2004 | Farjanel et al. |
| 2004/0253220 A1 | 12/2004 | Perrier et al. |
| 2004/0253606 A1 | 12/2004 | Aziz et al. |
| 2004/0258676 A1 | 12/2004 | Perrier et al. |
| 2004/0265230 A1 | 12/2004 | Martinez et al. |
| 2005/0020521 A1 | 1/2005 | Rana et al. |
| 2005/0079538 A1 | 4/2005 | Griffin et al. |
| 2005/0119202 A1 | 6/2005 | Kreutzer et al. |
| 2005/0181375 A1 | 8/2005 | Aziz et al. |
| 2005/0259483 A1 | 11/2005 | Nakamura et al. |
| 2005/0260639 A1 | 11/2005 | Nakamura et al. |
| 2006/0019256 A1 | 1/2006 | Clarke et al. |
| 2006/0083736 A1 | 4/2006 | Law et al. |
| 2006/0088532 A1 | 4/2006 | Alitalo et al. |
| 2006/0088882 A1 | 4/2006 | Jain et al. |
| 2006/0127402 A1 | 6/2006 | Neufeld et al. |
| 2006/0127902 A1 | 6/2006 | Madden et al. |
| 2006/0134172 A1 | 6/2006 | Shepard et al. |
| 2006/0134801 A1 | 6/2006 | Chada et al. |
| 2006/0216722 A1 | 9/2006 | Betholtz et al. |
| 2006/0223760 A1 | 10/2006 | Li et al. |
| 2007/0010469 A1 | 1/2007 | Chan et al. |
| 2007/0021365 A1 | 1/2007 | Erler et al. |
| 2007/0037203 A1 | 2/2007 | Kapeller-Libermann et al. |
| 2007/0054278 A1 | 3/2007 | Cargill |
| 2007/0059745 A1 | 3/2007 | Sharp et al. |
| 2007/0148173 A1 | 6/2007 | Huang et al. |
| 2007/0154481 A1 | 7/2007 | Gelinas et al. |
| 2007/0184439 A1 | 8/2007 | Guilford et al. |
| 2007/0197424 A1 | 8/2007 | Friedman et al. |
| 2007/0225242 A1 | 9/2007 | Erler et al. |
| 2007/0231323 A1 | 10/2007 | Phillips |
| 2007/0243214 A1 | 10/2007 | Schiemann et al. |
| 2008/0031817 A1 | 2/2008 | Mazar et al. |
| 2008/0118928 A1 | 5/2008 | Hageman |
| 2008/0137893 A1 | 6/2008 | Ross et al. |
| 2008/0181896 A1 | 7/2008 | Khan et al. |
| 2008/0187523 A1 | 8/2008 | Zhang et al. |
| 2008/0220424 A1 | 9/2008 | Haber et al. |
| 2008/0248477 A1 | 10/2008 | Holtzman et al. |
| 2008/0261870 A1 | 10/2008 | Trackman et al. |
| 2008/0274453 A1 | 11/2008 | Hageman |
| 2008/0279857 A1 | 11/2008 | Skerry et al. |
| 2008/0286808 A1 | 11/2008 | Schellenberger et al. |
| 2008/0292547 A1 | 11/2008 | Tolleshaug et al. |
| 2008/0305965 A1 | 12/2008 | Moorhouse et al. |
| 2009/0022703 A1 | 1/2009 | Li et al. |
| 2009/0023149 A1 | 1/2009 | Knudsen et al. |
| 2009/0035348 A1 | 2/2009 | Zadini et al. |
| 2009/0053224 A1 | 2/2009 | Smith et al. |
| 2009/0104201 A1 | 4/2009 | Smith et al. |
| 2009/0142301 A1 | 6/2009 | Bevec et al. |
| 2009/0232773 A1 | 9/2009 | Kato et al. |
| 2009/0233270 A9 | 9/2009 | St. Croix et al. |
| 2009/0239947 A1 | 9/2009 | Dai et al. |
| 2009/0275633 A1 | 11/2009 | Esteller |
| 2010/0119515 A1 | 5/2010 | Neufeld et al. |
| 2010/0144603 A1 | 6/2010 | Watnick |
| 2010/0203062 A1 | 8/2010 | Stalmans et al. |
| 2010/0209415 A1 | 8/2010 | Smith et al. |
| 2010/0317721 A1 | 12/2010 | Neufeld et al. |
| 2011/0044907 A1 | 2/2011 | Marshall et al. |
| 2011/0044981 A1 | 2/2011 | Spangler et al. |
| 2011/0076272 A1 | 3/2011 | Smith et al. |
| 2011/0076285 A1 | 3/2011 | Stalmans et al. |
| 2011/0076739 A1 | 3/2011 | McCauley et al. |
| 2011/0200606 A1 | 8/2011 | McCauley et al. |
| 2011/0207144 A1 | 8/2011 | Marshall et al. |
| 2012/0087917 A1 | 4/2012 | Smith et al. |
| 2012/0202206 A1 | 8/2012 | Neufeld et al. |
| 2012/0309020 A1 | 12/2012 | Smith et al. |
| 2013/0017207 A1 | 1/2013 | Smith et al. |

FOREIGN PATENT DOCUMENTS

| | | |
|---|---|---|
| EP | 0799891 | 10/1997 |
| EP | 0960192 | 12/1999 |
| EP | 1149169 | 10/2001 |
| EP | 1616881 | 1/2006 |
| EP | 1690932 | 8/2006 |
| EP | 1693448 | 8/2006 |
| EP | 1715035 | 10/2006 |
| EP | 2078531 | 7/2009 |
| EP | 1315519 | 12/2010 |
| WO | WO-89/12060 | 12/1989 |
| WO | WO-92/20702 | 11/1992 |
| WO | WO-96/00614 | 1/1996 |
| WO | WO-96/40746 | 12/1996 |
| WO | WO-97/00441 | 1/1997 |
| WO | WO-98/06830 | 12/1998 |
| WO | WO-99/65928 | 12/1999 |
| WO | WO-00/44910 | 3/2000 |
| WO | WO-01/83702 | 8/2001 |
| WO | WO-91/83792 | 8/2001 |
| WO | WO-01/92495 | 12/2001 |
| WO | WO-02/11667 | 2/2002 |
| WO | WO-02/061092 | 8/2002 |
| WO | WO-02/079492 | 10/2002 |
| WO | WO-02/086443 | 10/2002 |
| WO | WO-03/031939 | 4/2003 |
| WO | WO-03/100016 | 12/2003 |
| WO | WO-2004/023973 | 3/2004 |
| WO | WO-2004/047720 | 6/2004 |
| WO | WO-2004/061423 | 7/2004 |
| WO | WO-2004/091655 | 10/2004 |
| WO | WO-2005/100604 | 10/2005 |
| WO | WO-2006/128740 | 7/2006 |
| WO | WO-2007/045927 | 4/2007 |
| WO | WO-2007/126457 | 11/2007 |
| WO | WO-2008/063479 | 5/2008 |
| WO | WO-2008/070616 | 6/2008 |
| WO | WO-2008/132453 | 11/2008 |
| WO | WO-2008/138578 | 11/2008 |
| WO | WO-2009/010974 | 1/2009 |
| WO | WO-2009/017833 | 2/2009 |
| WO | WO-2009/035791 | 3/2009 |
| WO | WO-2010/080769 | 7/2010 |
| WO | WO-2010/091279 | 8/2010 |
| WO | WO-2011/022667 | 2/2011 |
| WO | WO-2011/022670 | 2/2011 |
| WO | WO-2011/022706 | 2/2011 |
| WO | WO-2011/022709 | 2/2011 |
| WO | WO-2011/022710 | 2/2011 |
| WO | WO-2011/041309 | 4/2011 |

(56) References Cited

FOREIGN PATENT DOCUMENTS

| | | |
|---|---|---|
| WO | WO-2011/097513 | 8/2011 |
| WO | WO-2012/139045 | 10/2012 |
| WO | WO-2012/167181 | 12/2012 |

OTHER PUBLICATIONS

Final Office Action mailed May 10, 2013 in U.S. Appl. No. 12/185,054.
Office Action mailed Apr. 2, 2013, in U.S. Appl. No. 13/707,495.
Extended Search Report mailed Mar. 21, 2013, for EP 12172214.4.
Notice of the Second Office Action mailed Dec. 31, 2012 for CN 200880110519.8.
Notice of Allowance mailed Feb. 6, 2013, in U.S. Appl. No. 12/185,050.
Notice of Reasons for Rejection (translation) mailed Feb. 1, 2013 for JP 2010-519263.
Office Action mailed Feb. 28, 2013, in U.S. Appl. No. 12/652,687.
Office Action mailed Jun. 3, 2013, in U.S. Appl. No. 13/619,139.
Office Action mailed Feb. 15, 2013, in U.S. Appl. No. 13/021,555.
First Examination Report dated Apr. 4, 2013, in NZ 601615.
Extended Search Report mailed Mar. 5, 2013, for EP 10810702.0.
Communication Pursuant to Rules 70(2) and 70a(2) EPC mailed Mar. 22, 2013, for EP 10810702.0.
Caldas et al. (2003) "Humanization of the Anti-CD 18 Antibody 6.7: An Unexpected Effect of a Framework Residue in Binding to Antigen," Mol. Immunol. 39(15): 941-952.
Campbell, Monoclonal Antibody Technology, "General Properties and Applications of Monoclonal Antibodies," Chapter 1, 1-32 (Elsevier Science Publishers B.V.) (1984).
Casset et al. (2003) A Peptide Mimetic of an Anti-CD4 Monoclonal Antibody by Rational Design, Biochem. Biophys. Res. Commun. 307(1):198-205.
Chien et al. (1989) "Significant Structural and Functional Change of an Antigen-binding Site by a Distant Amino Acid Substitution: Proposal of a Structural Mechanism,"Proc. Natl. Acad. Sci. USA 86(14): 5532-5536.
Fujimoto et al. (2009) "Reciprocal Regulation of LOX and LOXL2 Expression During Cell Adhesion and Terminal Differentiation in Epidermal Keratinocytes," Journal of Dermatological Science 55(2):91-98.
Giusti et al. (1987) "Somatic Diversification of S107 from an Antiphosphocholine to an Anti-DNA Autoantibody is Due to a Single Base Change in its Heavy Chain Variable Region," Proc. Natl. Acad. Sci. USA 84(9): 2926-2930.
Gussow et al. (1991) "Humanization of Monoclonal Antibodies," Methods in Enzymology 203: 99-121.
Harmsen and Haard (2007) "Properties, Production, and Applications of Camelid Singledomain Antibody Fragments," Appl. Microbiol. Biotechnol. 77:13-22.
Holm et al. (2007) "Functional Mapping and Single Chain Construction of the Anti-Cytokeratin 8 Monoclonal Antibody TS1," Mol. Immunol. 44(6): 1075-1084.
Jiang et al., (2005) "A Novel Peptide Isolated from a Phage Display Peptide Library with Trastuzumab can Mimic Antigen Epitope of HER-2," J. Biol. Chem. 280 (6):4656-4662.
MacCallum et al. "Antibody-antigen Interactions: Contact Analysis and Binding Site Topography," (1996) J. Mol. Biol. 262(5):732-745.
Maki et al. (2002) "Inactivation of the Lysyl Oxidase Gene Lox Leads to Aortic Aneurysms, Cardiovascular Dysfunction, and Perinatal Death in Mice," Circulation 106(19):2503-2509.
Mariuzza et al. (1987) "The Structural Basis of Antigen-antibody Recognition," Annu. Rev. Biophys. Chem. 16:139-159.
Mollenhauer, et al. (1987) "Distribution of Extracellular Matrix Proteins in Pancreatic Ductal Adenocarcinoma and Its Influence on Tumor Cell Proliferation in Vitro," 2(1): 14-24.
Pascalis, et al. (2002). "Grafting of "Abbreviated" Complementarity-Determining Regions Containing Specificity-Determining Residues Essential for Ligand Contact to Engineer a Less Immunogenic Humanized Monoclonal Antibody," J. Immunol. 169(6): 3076-3084.

Peroutka, et al. (2008) "Enhanced Protein Expression in Mammalian Cells Using Engineered SUMO Fusions: Secreted phospholipase A2" Protein Sci. 17(9):1586-1595.
Stancoviski et al. (1991) "Mechanistic Aspects of the Opposing Effects of Monoclonal Antibodies to the ERBB2 Receptor on Tumor Growth," Proc. Natl. Acad. Sci UAS 88: 8691-8695.
Tannock. "Experimental Chemotherapy," Ch. 19, p. 338 and 352-359, in The Basic Science of Oncology, Tannock and Hill, eds., New York 1992.
Terui, et al. (2006) "Blockade of bulky lymphoma-associated CD55 expression by RNA interference overcomes resistance to complement-dependent cytotoxicity with rituximab," Cancer Sci. 97: 72-79.
Vajdos et al. (2002) "Comprehensive Functional Maps of the Antigen-binding Site of an Anti-ErbB2 Antibody Obtained with shotgun Scanning Mutagenesis," J. Mol. Biol. 320(2): 415-428.
Wu et al. (1999) "Humanization of a Murine Monoclonal Antibody by Simultaneous Optimization of Framework and CDR Residues," J. Mol. Biol. 294(1):151-162.
Adamson et al., "The Pathogenesis of Bleomycin-Induced Pulmonary Fibrosis in Mice," Am. J. Pathol. (1974) 77(2):185-189.
Akhtar et al., "The Sponge/Matrigel Angiogenesis Assay," Angiogenesis (2002) 5(1-2):75-80.
Akiri et al., "Lysyl Oxidase-Related Protein-1 Promotes Tumor Fibrosis and Tumor Progression In Vivo," Cancer Res. (2003) 63(7):1657-1666.
Albini et al., "The Chemoinvasion Assay: A Tool to Study Tumor and Endothelial Cell Invasion of Basement Membranes," Int. J. Dev. Biol. (2004) 48:563-571.
Arguello et al., "Incidence and Distribution of Experimental Metastases in Mutant Mice with Defective Organ Microenvironments (Genotypes S1/S1d and W/Wv)." Cancer Research (1992) 52(8):2304-2309.
Asuncion et al., "A Novel Human Lysyl Oxidase-Like Gene (LOXL4) on Chromosome 10q24 has an Altered Scavenger Receptor Cysteine Rich Domain," Matrix Biol. (2001) 20(7):487-491.
Atabani et al., "Identification of an Immunodominant Neutralizing and Protective Epitope from Measles Virus Fusion Protein by Using Human Sera from Acute Infection," J. Virology (1997) 71(10):7240-7245.
Atsawasuwan et al., "Expression of Lysyl Oxidase Isoforms in MC3T3-E1 Osteoblastic Cells," Biochem. Biophys. Res. Commun. (2005) 327(4):1042-1046.
Auerbach et al., "A Simple Procedure for the Long-Term Cultivation of Chicken Embryos," Devel. Biol. (1974) 41(2):391-394.
Auerbach et al., "Angiogenesis Assays: A Critical Overview," Clinical Chemistry (2003) 49(1):32-40.
Barzu et al., "Characterization of B-Cell Epitopes on IpaBeta, an Invasion-Associated Antigen of Shigella flexneri: Identification of an Immunodominant Domain Recognized During Natural Infection," Infection and Immunity (1993) 61(9):3825-3831.
Bendig, Methods: "Humanization of Rodent Monoclonal Antibodies by CDR Grafting," A Companion to Methods in Enzymology (1995) 8:83-93.
Betakova et al., "Monoclonal Anti-Idiotypic Antibodies Mimicking the Immunodominant Epitope of Influenza Virus Haemagglutinin Elicit Biologically Significant Immune Responses," J. Gen. Virology (1998) 79(Pt.3):461-470.
Blacher et al., "Improved Quantification of Angiogenesis in the Rat Aortic Ring Assay," Angiogenesis (2001) 4(2):133-142.
Borel et al., "Lysyl Oxidase-Like Protein from Bovine Aorta. Isolation and Maturation to an Active Form by Bone Morphogenetic Protein-1," J. Biol. Chem. (2001)276(52):48944-48949.
Bouez et al., "The Lysyl Oxidase LOX is Absent in Basal and Squamous Cell Carcinomas and its Knockdown Induces an Invading Phenotype in a Skin Equivalent Model," Clinical Cancer Res. (2006) 12(5):1463-1469.
Breihaupt et al., "Demyelinating Myelin Oligodendrocyte Glycoprotein-Specific Autoantibody Response is Focused on One Dominant Conformational Epitope Region in Rodents," J. Immunology (2008) 181(2):1255-1263.
Brody et al., "Lung Lysyl Oxidase and Elastin Synthesis During Coompensatory Lung Growth," Chest (1976) 69(2 Supp):271-272.

(56) References Cited

OTHER PUBLICATIONS

Brown et al., "A Novel in Vitro Assay for Human Angiogenesis," Laboratory Investigation (1996) 75(4):539-555.
Brown et al., "Exploiting Tumour Hypoxia in Cancer Treatment," Nature Reviews (2004) 4:437-447.
Bruns et al., "Vascular Endothelial Growth Factor is an In Vivo Survival Factor for Tumor Endothelium in a Murine Model of Colorectal Carcinoma Liver Metastases," Cancer (2000) 89(3):488-499.
Burbelo et al., "Monoclonal Antibodies to Human Lysyl Oxidase," Coll. Relat. Res. (1986) 6(2):153-162.
Cairns et al., "Acute Hypoxia Enhances Spontaneous Lymph Node Metastasis in an Orthotopic Murine Model of Human Cervical Carcinoma," CVancer Res. (2004) 64:2054-2061.
Cancer Reference Information; Detailed Guide: Breast Cancer, How is Breast Cancer Diagnosed: www.cancerorg/docroot/CRI_2_4_3X_How_is_breast_cancer_diagnosed, dated Nov. 16, 2009.
Cardone et al., "Prognostic Value of Desmoplastic Reaction and Lumphocytic Infiltration in the Management of Breast Cancer," Panminerva Med. (1997) 39(3):174-177.
Chang et al., "The Many Faces of Metalloproteases: Cell Growth, Invasion, Angiogenesis and Metastasis," Trends Cell. Biol. (2001) 11(11):S37-43.
Chanoki et al., "Increased Expression of Lysyl Oxidase in Skin with Scleroderma," Br. J. Dermatol. (1995) 133(5):710-715.
Chichester et al., "Lung Lysyl Oxidase and Prolyl Hydroxylase: Increases Induced by Cadmium Chloride Inhalation and the Effect of β-Aminopropionitrile in Rats," Am. Rev. Respir. Dis. (1981) 124(6):709-713.
Chioza et al., "Mutations in the Lysyl Oxidase Gene are not Associated with Amyotrophic Lateral Sclerosis," Amyotroph. Lateral Scler. Other Motor Neuron. Disord. (2001) 2(2):93-97.
Chow et al., "Identification and Exrpession of an Allergen Asp f13 from *Aspergillus fumigatus* and Epitope Mapping Using Human IgE Antibodies and Rabbit Polyclonal Antibodies," Biochem. J. (2000) 346:423-431.
Christiansen et al., "Biological Impediments to Monoclonal Antibody-Based Cancer Immunotherapy," Mol. Cancer Ther. (2004) 3(11):1493-1501.
Colman, "Effects of Amino Acid Sequence Chances on Antibody-Antigen Interactions," Research in Immunology (1994) 145(1):33-36.
Csiszar et al., "Functional Analysis of the Promoter and First Intron of the Human Lysyl Oxidase Gene," Mol. Biol. Rep. (1996) 23(2):97-108.
Csiszar, "Lysyl Oxidases; A Novel Multifunctional Amine Oxidase Family," Progress in Nucleic Acid Research and Molecular Biology (2001) 7:1-32.
Csiszar, "Somatic Mutation of the Lysyl Oxidase Gene on Chromosome S023.1 in Colorectal Tumors," Int. J. Cancer (2002) 97:636-642.
Database Geneseq (Derwent, London, UK) Accession No. ABB07649; 99.9% identical to SEQ ID No. 2; dated Feb. 14, 2002.
Database Issued Patents (United States Patent & Trademark Office, Alexandria, VA) US Patent No. 6,300,092; 99.9% identical to SEQ ID No. 2; dated Oct. 9, 2001.
Decitre et al., "Lysyl Oxidase-Like Protein Localizes to Sites of De Novo Fibrinogenesis in Fibrosis and in the Early Stromal Reaction of Ductal Breast Carcinomas," Lab. Invest. (1998) 78(2):143-151.
Denko et al., "Investigating Hypoxic Tumor Physiology Through Gene Expression Patterns," Oncogene (2003) 22:5907-5914.
Dermer, :Another Anniversary for the War on Cancer, Biotechnology (1994) 12:320.
Dillman, "Monoclonal Antibodies for Treating Cancer," Ann. Intern. Med. (1989) 111(7):592-603.
Erler et al., "Hypoxia Promotes Invasion and Metastasis of Breast Cancer Cells by Increasing Lysyl Oxidase Expression," Breast Cancer Res. (2005) 7(Suppl 2):p. 5.05.
Erler et al., "Lysyl Oxidase is Essential for Hypoxia-Induced Metastasis," Nature (2006) 27:1222-1226.
Erler et al., "Lysyl Oxidase Mediates Hypoxic Control of Metastasis," Cancer Res. (2006) 66(21):10238-10241.
European Search Report for European Patent Application No. 10012458.5-2406, mailed Jul. 13, 2011, 5 pages.
Evans et al., "Vaccine Therapy for Cancer—Fact of Fiction?" QJM. (1999) 92(6):299-307.
Example from Wikipedia, the free encyclopedia, "Monoclonal Antibody Therapy," (http://en.wikipedia.org/wiki/antibody_therapy), accessed on Oct. 4, 2010.
Example of the USPTO's Written Description Training Materials, Revision 1, Mar. 25, 2008, 84 pgs.
Ferrari et al., "Identification of Immunodominant T Cell Epitopes of the Hepatitis B Virus Nucleocapsid Antigen," J. Clin. Invest. (1991) 88(1):214-222.
Fidler et al., "The Implications of Angiogenesis for the Biology and Therapy of Cancer Metastasis," Cell (1994) 79(2):185-188.
Fodstad et al., "A New Experimental Metastasis Model in Athymic Nude Mice, the Human Malignant Melanoma Lox," Intl. J. Cancer (1988) 41:442-449 (Abstract).
Fogelgren et al., "Cellular Fibronectin Binds to Lysyl Oxidase with High Affinity and is Critical for its Proteolytic Activation," J. Biol. Chem. (2005) 280(26):24690-24697.
Fong et al., "Lysyl Oxidase-Like 2 Expression is Increased in colon and Esophageal Tumors and Associated with Less Differentiated Colon Tumors," Genes, Chromosomes and Cancer (2007) 46(7):644-655.
Freshey, Culture of Animal Cells, A Manual of Basic Technique, Alan R. Liss, Inc., (1983), New York, p. 4.
Gacheru et al., "Transcriptional and Post-Transcriptional Control of Lysyl Oxidase Expression in Vascular Smooth Muscle Cells: Effects of TGF-β1 and Serum Deprivation," J. Cell Biochem. (1997) 65(3):395-407.
GenBank Public DNA Database Accession No. AAA59541.1 "Lysyl Oxidase [*Homo sapiens*]", Jan. 7, 1995.
GenBank Public DNA Database Accession No. AAB21243.1 "Lysyl Oxidase [*Homo sapiens*]", May 7, 1993.
GenBank Public DNA Database Accession No. AAB23549.1 "Lysyl oxidase [*Homo sapiens*]", May 8, 1993.
GenBank Public DNA Database Accession No. AAD02130.1 "Lysyl Oxidase [*Homo sapiens*]", May 6, 1999.
GenBank Public DNA Database Accession No. AAH15090.1 "Lysyl Oxidase-Like 1 [*Homo sapiens*]", Jul. 15, 2006.
GenBank Public DNA Database Accession No. AAH74820.1 "Lysyl Oxidase [*Homo sapiens*]", Jul. 15, 2006.
GenBank Public DNA Database Accession No. AAH74872.1 "Lysyl Oxidase [*Homo sapiens*]", Jul. 15, 2006.
GenBank Public DNA Database Accession No. AAK51671.1 "Lysyl Oxidase-Like 3 Protein [*Homo sapiens*]", May 9, 2001.
GenBank Public DNA Database Accession No. AAK71934.1 "Lysyl Oxidase-Related Protein C [*Homo sapiens*]", Jul. 11, 2001.
GenBank Public DNA Database Accession No. AF039291 "Homo Sapiens Lysyl Oxidase mRNA, Complete cds", May 6, 1999.
GenBank Public DNA Database Accession No. AF282619 "*Homo sapiens* Lysyl Oxidase-like 3 Protein mRNA, Complete cds", May 9, 2001.
GenBank Public DNA Database Accession No. AF338441 "*Homo sapiens* Lysyl Oxidase-Related Protein C (LOXC) mRNA, Complete cds", Jul. 11, 2001.
GenBank Public DNA Database Accession No. BC015090 "*Homo sapiens* Lysyl Oxidase-Like 1, mRNA (cDNA Clone MGC:16541 IMAGE:4040510), Complete cds", Jul. 15, 2006.
GenBank Public DNA Database Accession No. BC018439 "*Mus musculus* Lysyl Oxidase, mRNA (cDNA Clone MGC:11525 IMAGE:2655752), Complete cds", Jul. 15, 2006.
GenBank Public DNA Database Accession No. BC074820 "*Homo sapiens* Lysyl Oxidase, mRNA (cDNA Clone MGC:104085 IMAGE:30915536), complete cds", Jul. 15, 2006.
GenBank Public DNA Database Accession No. BC074872 "*Homo sapiens* Lysyl Oxidase, mRNA (cDNA Clone MGC:103851 IMAGE:30915233), Complete cds", Jul. 15, 2006.
GenBank Public DNA Database Accession No. M84150 "Human Lysyl Oxidase Gene, Partial cds", Jan. 7, 1995.

(56) References Cited

OTHER PUBLICATIONS

GenBank Public DNA Database Accession No. M94054 "Human Lysyl Oxidase (LOX) mRNA, Complete cds", Jan. 7, 1995.
GenBank Public DNA Database Accession No. NM_002317 "*Homo sapiens* Lysyl Oxidase (LOX), Transcript Variant 1, mRNA", Mar. 13, 2011.
GenBank Public DNA Database Accession No. NM_033325 "*Mus musculus* Lysyl Oxidase-Like 2 (Loxl2), mRNA", Mar. 10, 2011.
GenBank Public DNA Database Accession No. NP_002308 "Protein-Lysine 6-Oxidase Isoform 1 Preproprotein [*Homo sapiens*]", Mar. 13, 2011.
GenBank Public DNA Database Accession No. NP_002309 "Lysyl Oxidase 2 Precursor [*Homo sapiens*]", Mar. 27, 2011.
GenBank Public DNA Database Accession No. NP_005567 "Lysyl Oxidase Homolog 1 Preproprotein [*Homo sapiens*]", Mar. 27, 2011.
GenBank Public DNA Database Accession No. NP_034858 "Protein-Lysine 6-Oxidase Precursor [*Mus musculus*]", Mar. 11, 2011.
GenBank Public DNA Database Accession No. NP_034859 "Lysyl Oxidase Homolog 1 Precursor [*Mus musculus*]", Mar. 12, 2011.
GenBank Public DNA Database Accession No. NP_115587 "Lysyl Oxidase Homolog 4 Precursor [*Homo sapiens*]", Mar. 13, 2011.
GenBank Public DNA Database Accession No. NP_115882 "AP-1 Complex Subunit mu-1 Isoform 2 [*Homo sapiens*]", Mar. 13, 2011.
GenBank Public DNA Database Accession No. NP_201582 "Lysyl Oxidase Homolog 2 Precursor [*Mus musculus*]", Mar. 10, 2011.
GenBank Public DNA Database Accession No. S45875 "Lysyl Oxidase [Human, Skin Fibroblasts, mRNA Partial, 1254 nt]", May 8, 1993.
GenBank Public DNA Database Accession No. S78694 "Lysyl Oxidase [Human, mRNA, 1780 nt]", May 7, 1993.
GenBank Public DNA Database Accession No. U89942 "Human Lysyl Oxidase-Related Protein (WS9-14) mRNA, Complete cds", Aug. 18, 2003.
GenBank Public DNA Database, Accession No. AAA59525.1 "Lysyl Oxidase [*Homo sapiens*]", Jan. 7, 1995.
Giampuzzi et al. "Lysyl Oxidase Activates the Transcription Activity of Human Collagene III Promoter. Possible Involvement of Ku Antigen," J. Biol. Chem. (2000) 275(46):36341-36349.
Giampuzzi et al., "Down-Regulation of Lysyl Oxidase-Induced Tumorigenic Transformation in NRK-49F Cells Characterized by Constitutive Activation of Ras Proto-Oncogene," J. Biol. Chem. (2001) 276(31):29226-292232.
Go et al., "The Rat Aortic Ring Assay for In Vitro Study of Angiogenesis," Methods Mol. Med. (2003) 85:59-64.
Gonzalez-Iriate et al., "A Modified Chorioallantoic Membrane Assay Allows for Specific Detection of Endothelial Apoptosis Induced by Antiangiogenic Substances," Angiogenesis (2003) 6(3):251-254.
Grant et al., "Overview: Rational Integration of Agents Directed at Novel Therapeutic Targets into Combination Chemotherapeutic Regimens," Curr.Opin. Investig. Drugs (2001) 2(11):1600-1605.
Gross et al., "Idiopathic Pulmonary Fibrosis," N. Engl. J. Med. (2001) 345(7):517-525.
Guedez et al., "Quantitative Assessment of Angiogenic Responses by the Directed In Vivo Angiogenesis Assay," Am. J. Pathol. (2003) 162(5):1431-1439.
Gura, "Systems for Identifying New Drugs are Often Faulty," Science (1997) 278(5347):1041-1042.
Harris et al., "Connective Tissue Amine Oxidase II. Purification and Partial Characterization of Lysyl Oxidase from Chick Aorta," Biochim. Biophys. Acta (1974) 341(2):332-344.
Harrison et al., "High Dose Continuous Infusion of Bleomycin in Mice: A New Model for Drug-Induced Pulmonary Fibrosis," J. Pharmacol. Exp. Ther. (1987) 243(3):1185-1194.
Hartwell, "Angiogenesis in P- and E-Selectin-Deficient Mice," Microcirculation (1998) 5(2-3):173-178.
Hein et al., "Lysyl Oxidases: Expression in the Fetal Membranes and Placenta," Placenta (2001) 22(1):49-57.
Herrington et al., "Principles and Basic Methodology of DNA/RNA Detection by in Situ Hybridization," Ch. 4, pp. 69-102, Diagnostic Molecular Pathology, vol. 1, Phenotyping and Genotyping of Intact Cells, (IRL Press, Oxford University Press, 1992).
Higgins et al., "Hypoxia Promotes a Fibrogenesis In Vivo Via HIF-1 Stimulation of Epithelial-to-Mesenchymal Transition," Journal Clinical Investigation (2007) 117(12):3810-3820.
Hockel et al., "Tumor Hypoxia: Definitions and Current Clinical, Biologic and Molecular Aspects," Journal of the National Cancer Instititute (2001) 4(93):266-276.
Hohenester et al., "Crystal Structure of a Scavenger Receptor Cysteine-Rich Domain Sheds Light on an Ancient Superfamily," Nat. Struct. Biol. (1999) 6(3):228-232.
Hornstra et al., "Lysyl Oxidase is Required for Vascular and Diaphragmatic Development in Mice," J. Biol. Chem. (2003) 278(16):14387-14393.
Huang et al. "Cloning and Characterization of a Human Lysyl Oxidase-Like 3 Gene (hLOXL3)," Matrix Biol. (2001) 20(2):153-157.
Ito et al., "Molecular Cloning and Biological Activity of a Novel Lysyl Oxidase-Related Gene Expressed in Cartilage," J. Biol. Chem. (2001) 276(26):24023-24029.
Jain, "Barriers to Drug Delivery in Solid Tumors," Scientific American (1994) 271(1):58-65.
Jakobsson et al., "A Morphometric Method to Evaluate Angiogenesis Kinetics in the Rat Mesentery," Into. J. Exp. Pathol. (1994) 75(3):214-219.
Jansen et al., "Intracellular Localization of the Matrix Enzyme Lysyl Oxidase in Polarized Epithelial Cells," Matrix Biol. (2007) 26(2):136-139.
Jansen et al., "Lysyl Oxidase Regulates Kidney Epithelial Cell Phenotype," ASMB Meeting Abstract/Matrix Biology (2006) 25:S92.
Jourdan Le-Saux et al., "Central Nervous System, Uterus, Heart, and Leukocyte Expression of the LOXL3 Gene, Encoding a Novel Lysyl Oxidase-Like Protein," Genomics (2001) 74(2):211-218.
Jourdan Le-Saux et al., "Lysyl Oxidase cDNA of Myofibroblast from Mouse Fibrotic Liver," Biochem. Biophys. Res. Comm. (1994) 199(2):587-592.
Jourdan Le-Saux et al., "The LOXL2 Gene Encodes a New Lysyl Oxidase-Like Protein and is Expressed at High Levels in Reproductive Tissues," J. Biol. Chem. (1999) 274(18):12939-12944.
Jourdan-Le Saux et al., "The Human Lysyl Oxidase-Related Gene (LOXL2) Maps Between Markers D8S280 and D8S278 on Chromosome 8p21.2-p21.3," Genomics (1998) 51(2):305-307.
Jourdan-Le Saux et al., "The Mouse Lysyl Oxidase-Like 2 Gene (mLOXL2) Maps to Chromosome 14 and is Highly Expressed in Skin, Lung, and Thymus," Matrix Biol. (2000) 19(2):179-183.
Jung et al., "Purification of Enzymatically Active Human Lysyl Oxidase and Lysyl Oxidase-Like Protein from *Escherichia coli* Inclusion Bodies," Protein Expr. Purif. (2003) 31(2):240-246.
Kagan et al., "Catalytic Properties and Structural Components of Lysyl Oxidase," Novartis Foundation Symp. (1995) 192:100-115; discussion 115-121.
Kagan et al., "Expression of Lysyl Oxidase from cDNA Constructs in Mammalian Cells: The Propeptide Region is not Essential to the Folding and Secretion of the Functional Enzyme," J. Cell Biochem. (1995) 59(3):329-338.
Kagan et al., "Lysyl Oxidase: Properties, Specificity, and Biological Roles Inside and Outside the Cell," J. Cell Biochem. (2003) 88:660-672.
Kagan et al., "Lysyl Oxidase: Preparation and Role in Elastin Biosynthesis," Meth. Enzymol. (1982) 82(A):637-649.
Kagan, "Intra-and Extracellular Enzymes of Collagen Biosynthesis as Biological and Chemical Targets in the Control of Fibrosis," Acta Tropica (2000) 77(1):147-152.
Kagan, "Lysyl Oxidase: Mechanism, Regulation and Relationship to Liver Fibrosis," Pathol. Res. Pract. (1994) 190(9-10):9210-919.
Kamath et al., "Signaling from Protease-Activated Receptor-1 Inhibits Migration and Invasion of Breast Cancer Cells," Cancer Res. (2001) 61(15):5933-5940.
Kaneda et al., "Lysyl Oxidase is a Tumor Suppressor Gene Inactivated by Methylation and Loss of Heterozygosity in Hyman Gastric Cancers," Cancer Res. (2004) 64:5410-5415.
Kenyon et al., "Lysyl Oxidase and mg Messenger RNA," Science (1991) 253:802.

(56) References Cited

OTHER PUBLICATIONS

Kenyon et al., "TGF-β1 Causes Airway Fibrosis and Increased Collagen I and III mRNA in Mice," Thorax (2003) 58(9):772-777.

Khakoo et al., "Congenital Cutis Laxa and Lysyl Oxidase Deficiency," Clin. Genet. (1997) 51(2):109-114.

Kim et al., "A Highly Polymorphic (CA) Repeat Sequence in the Human Lysyl Oxidase-Like Gene," Clin. Genet. (1997) 51(2):131-132.

Kim et al., "A New Gene with Sequence and Structural Similarity to the Gene Encoding Human Lysyl Oxidase," J. Biol. Chem. (1995) 270(13):7176-7182.

Kim et al., "Coexpression of the Lysyl Oxidase-Like Gene (LOXL) and the Gene Encoding Type III Procollagen in Induced Liver Fibrosis," J. Cell Biochem. (1999) 72(2):181-188.

Kirschmann et al, "A Molecular Role for Lysyl Oxidase in Breast Cancer Invasion," Cancer Res. (2002) 62:4478-4483.

Kirschmann et al., "Differentially Expressed Genes Associated with the Metastatic Phenotype in Breast Cancer," Breast Cancer Res. Treat. (1999) 55(2):127-136.

Kragh et al., "In Vivo Chamber Angiogenesis Assay: An Optimized Matrigel Plug Assay for Fast Assessment of Anti-Angiogenic Activity," Intl. J. Oncology (2003) 22(2):305-311.

Krebs et al., "Lysyl Oxidase Copper-Talon Complex: A Model," Biochim. Biophys. Acta (1993) 1202(1):7-12.

Lazarus et al., "Induction of Human Monocyte Motility by Lysyl Oxidase," Matrix Biol. (1995) 14(9):727-731.

Le et al., "Expression and Prognostic Significance of a Panel of Tissue Hypoxia Markers in Head-and -Neck Squamous Cell Carcinoma," Int. J. Radiation Oncology Biol. Phys. (2007) 69(1):157-175.

Levene et al., "Possibilities for the Therapeutic Control of Fibrosis," Br. J. Dermatol. (1985) 112(3):363-371.

Li et al., "Localization and Activity of Lysyl Oxidase Within Nuclei of Fibrogenic Cells," Proc. Natl. Acad. Sci. (1997) 94:12817-12822.

Lichtenberg et al., "The Rat Subcutaneous Air Sac Model: A Quantitative Assay of Antiangiogenesis in Induced Vessels," Am J. Pharmacol. Toxicology (1999) 84(1):34-40.

Luo et al., "Differential Inhibition of Fluid Accumulation and Tumor Growth in Two Mouse Ascites Tumors by an Antivascular Endothelial Growth Factor/Permeability Factor Neutralizing Antibody," Cancer Res. (1998) 58(12):2594-2600.

Luo et al., "Significant Expression of Vascular Endothelial Growth Factor/Vascular Permeability Factor in Mouse Ascites Tumors," Cancer Res. (1998) 58(12):2652-2660.

Madakamutil et al., "Immunodiominance in the TCR Repertoire of a TCR Peptide-Specific CD4+ Treg Population that Controls Experimental Autoimmune Encephalomyelitis," J. Immunology (2008) (180):4577-4585.

Maki et al., "Cloning and Characterization of a Fifth Human Lysyl Oxidase Isoenzyme: the Third Member of the Lysyl Oxidase-Related Subfamily with Four Scavenger Receptor Cysteine-Rich Domains," Matrix Biol. (2001) 20(7):493-496.

Maki et al., "Cloning and Characterization of a Fourth Human Lysyl Oxidase Isoenzyme," Biochem. J. (2001) 355:381-387.

Masson et al., "Mouse Aortic Ring Assay: A New Approach of the Molecular Genetics of Angiogenesis," Biol. Proc. Online (2002) 4:24-31.

Mattioli et al., "Mimicry of the Immunodominant Conformation-Dependent Antigenic Site of Hepatitis A Virus by Motifs Selected from Synthetic Peptide Libraries," Journal of Virology (1995) 69(9):5294-5299.

Mbeunkui et al., "Identification of Differentially Secreted Biomarkers Using LC-MS/MS in Isogenic Cell Lines Representing a Progression of Breast Cancer," Journal Proteome Res. (2007) 6:2993-3002.

Molnar et al., "Structural and Functional Diversity of Lysyl Oxidase and the LOX-like Proteins," Biochimica Biophysica Acta (2003) 1547:220-224.

Murawaki et al., "Serum Lysyl Oxidase Activity in Chronic Liver Disease in Comparison with Serum Levels of Prolyl Hydrozylase and Laminin," Hepatology (1991) 14(6):1167-1173.

National Cancer Instititute, Staging: Questions and Answers (www.cancer.gov/cancertopics/factsheet/detection/staging) accessed Nov. 6, 2009.

Nehls et al., "A Novel, Microcarrier-Based In Vitro Assay for Rapid and Reliable Quantification of Three-Dimensional Cell Migration and Angiogenesis," Microvascular Res. (1995) 50(3):311-322.

Nelson et al., "Effect of β-Aminopropionitrile and Ascorbate on Fibroblast Migration," Proc. Soc. Exp. Biol. Med. (1988) 188(3):346-352.

Nguyen et al., "Quantitation of Angiogenesis and Antiangiogenesis in the Chick Embryo Chorioallantoic Membrane," Microvascular Res. (1994) 47(1):31-40.

Nicosia et al., "Growth of Microvessels in Serum-Free Matrix Culture of Rat Aorta. A Quantative Assay of Angiogenesis In Vitro," Laboratory Investig. (1990) 63(1):115-122.

Nissanov et al., "Automatic Vessel Segmentation and Quantification of the Rat Aortic Ring Assay of Angiogenesis," Laboratory Investig. (1995) 73(5):734-739.

Norby, "On the Quantitative Rat Mesenteric-Window Angiogenesis Assay," EXS (1992) 61:282-286.

Okada et al., "A Quantitative In Vivo Method of Analyzing Human Tumor-Induced Angiogenesis in Mice Using Agarose Microencapsulation and Hemoglobin Enzyme-Linked Immunosorbent Assay," Japan. J. Cancer Res. (1995) 86(12):1182-1188.

Ooshima et al., "Increased Lysyl Oxidase Activity in Blood Vessels of Hypertensive Rats and Effect of Beta-Aminopropionitrile on Arteriosclerosis," Jpn. Circ. J. (1977) 41(12):1337-1340.

Orimo et al., "Cancer-Associated Myofibroblasts Possess Various Factors to Promote Endometrial Tumor Progression," Clin. Cancer Res. (2001) 7(1):3097-3105.

Orimo et al., "Stromal Fibroblasts in Cancer: A Novel Tumor-Promoting Cell Type," Cell Cycle (2006) 5(15):1597-1601.

Palamakumbura et al., "A Fluoremetric Assay for Detection of Lysyl Oxidase Enzyme Activity in Biological Samples," Analytical Biochem. (2002) 300:245-251.

Palamakumbura et al., The Propeptide Domain of Lysyl Oxidase Induces Phenotypic Reversion of Ras-Transformed Cells, J. Biol. Chem. (2004) 279(39):40593-40600.

Panchenko et al., "Metalloproteinase Activity Secreted by Fibrogenic Cells in the Porcessing of Prolysyl Oxidase. Potential Role of Procollagen C-Proteinase," J. Biol. Chem. (1996) 271(12):7113-7119.

Parsons-Wingerter et al., "Fibroblast Growth Factor-2 Selectively Stimulates Angiogenesis of Small Vessels in Arterial Tree," Arteriosclerosis Thrombosis Vasc. Biol. (2000) 20(5):1250-1256.

Paul, Fundamental Immunology, 3rd Edition (1993) pp. 292-295.

Payne et al., "Lysyl Oxidase Regulates Breast Cancer Cell Migration and Adhesion through a Hydrogen Peroxide-Mediated Mechanism," Cancer Res. (2005) 65(24):11429-11436.

Peinado et al., "A Molecular Role for Lysyl Oxidase-Like 2 Enzyme in Snail Regulation and Tumor Progression," EMBO J. (2005) 24(19):3446-3458.

Peinado et al., "Lysyl Oxidase-Like 2 as a New Poor Prognosis Marker of Squamous Cell Carcinomas," Cancer Res. (2008) 68(12):4541-4550.

Peyroll et al., "Lysyl Oxidase Gene Expression in the Stromal Reaction to In Situ and Invasive Ductal Breast Carcinoma," Am. J. Pathol. (1997) 150(2):497-507.

Pinnell, "Molecular Defects in the Ehlers-Danlos Syndrome," J. Invest. Dermatol. (1982) 79(Supp 1):905-925.

Pires Martins et al., "Whole-Body Gene Expression by Data Mining," Genomics (2001) 72(1):34-42.

Postlethwaite et al., "Stimulation of the Chemotactic Migration of Human Fibroblasts by Transforming Growth Factor β," J. Exp. Med. (1987) 165(1):251-256.

Presta et al., "Purine Analogue 6-Methylmercaptopurine Riboside Inhibits Early and Late Phases of the Angiogenesis Process," Cancer Res. (1999) 59(10):2417-2424.

R&D Systems Ordering Information: Catalog No. MAB2639, Anti-Human Lysyl Oxidase Homolog 2 Monoclonal Antibody, dated Apr. 18, 2005.

Radisky et al., "Tumors are Unique Organs Defined by Abnormal Signaling and Context," Semin. Cancer Bio. (2001) 11(2):87-95.

(56) References Cited

OTHER PUBLICATIONS

Rakic et al., "Placental Growth Factor, a Member of the VEGF Family, Contributes to the Development of Choroidal Neovascularization," Invest. Opthalmol. Vis. Sci. (2003) 44(7):3186-3193.
Rayton et al., "Induction of Lysyl Oxidase with Copper. Properties of an In Vitro System," J. Biol. Chem. (1979) 254(3):621-626.
Reichmann et al., "Reshaping Human Antibodies for Therapy," Nature (1988) 332(6162):323-327.
Ren et al., "Reduced Lysyl Oxidase Messenger RNA Levels in Experimental and Human Prostate Cancer," Cancer Res. (1998) 58:1285-1290.
Resnick et al., "The SRCR Superfamily: A Family Reminiscent of the Ig Superfamily," Trends Biochem. Sci. (1994) 19(1):5-8.
Ribatti et al., The Chick Embryo Chorioallantoic Membrane as a Model for In Vivo Research on Angiogenesis, Intl. J. Devel. Biol. (1996) 40(6):1189-1197.
Ribatti et al., "New Model for the Study of Angiogenesis and Antiangiogenesis in the Chick Embryo Chorioallantoic Membrane: The Gelatin Sponge/Chorioallantoic Membrane Assay," J. Vascular Res. (1997) 34(6):455-463.
Ribatti et al., "The Chick Embryo Chorioallantoic Membrane as a Model for In Vivo Research on Anti-angiogenesis," Curr. Pharmacol. Biotechnol. (2000) 1(1):73-82.
Richardson et al., "Observations on the Use of the Avian Chorioallantoic Membrane (CAM) Model in Investigations into Angiogenesis," Curr. Drug Targets Cardiovasc. Hematol. Disoders (2003) 3(2):155-185.
Rodriguez et al., "Regulation of Lysyl Oxidase in Vascular Cells: Lysyl Oxidase as a New Player in Cardiovascul Diseases," Cardiovasc. Res. (2008) 79(1):7-13.
Rost et al., "Reduction of LOX- and LOX2-mRNA Expression in Head and Neck Squamous Cell Carcinomas," Anticancer Res. (2003) 23(2B):1565-1573.
Royce et al., "Reduced Lysyl Oxidase Activity in Skin Fibroblasts from Patients with Menkes' Syndrome," Biochem. J. (1980) 192(2):579-586.
Rozalski et al., "Epitope Specificities of Murine Monoclonal and Rabbit Polyclonal Antibodies Against Enterobacterial Lipopolysaccharides of the Re Chemotype," Infection and Immunity (1989) 57(9):2645-2652.
Rucker et al., "Copper, Lysyl Oxidase, and Extracellular Matrix Protein Cross-Linking," Am. J. Clin. Nutr. (1998) 67(suppl):996S-1002S.
Rudikoff et al., "Single Amino Acid Substitution Altering Antigen-Binding Specificity," Proc. Natl. Acad. Sci. USA (1982) 79(6):1979-1983.
Saito et al., "Regulation of a Novel Gene Encoding a Lysyl Oxidase-Related Protein in Cellular Adhesion and Senescence," J. Biol. Chen. (1997) 272(13):8157-8160.
Sappino et al., "Smooth-Muscle Differentiation in Stromal Cells of Malignant and Non-Malignant Breast Tissues," Int. J. Cancer (1988) 41(5):707-712 (abstract only).
Sasaki et al., "Mac-2 Binding Protein is a Cell-Adhesive Protein of the Extracellular Matrix which Self-Assembles into Ring-Like Structures and Binds β1 Integrins, Collagens and Fibronectin," EMBO J. (1998) 17(6):1606-1613.
Satoh et al., "Inhibition of Local Adhesion Kinase by Antisense Oligonucleotides Enhances the Sensitivity of Breast Cancer Cells to Camptothecins," Biocell (2003) 27(1):47-55.
Search Report for European Patent Application No. 08020752, dated May 20, 2009.
Search Report for European Patent Application No. 08020753, dated May 26, 2009.
Sevil et al., "Pharmacokinetic Analysis of Beta-Aminopropionitrile in Rabbits," Vet Res. (1996) 27(2):117-123 (Abstract).
Sheridan et al., "Increased Lysyl Oxidase Activity in Aortas of Hypertensive Rats and Effect of Beta-Aminopropionitrile," Exp. Mol. Pathol. (1979) 30(2):315-324.
Shieh et al., "Association of Expression Aberrances and Genetic Polymorphisms of Lysyl Oxidase with Areca-Associated Oral Tumorigenesis," Clinical Cancer Res. (2007) 13(15):4378-4385.
Siegel et al., "Biochemical and Immunochemical Study of Lysyl Oxidase in Experimental Hepatic Fibrosis in the Rat," Proc. Natl. Acad. Sci. USA (1978) 75(6):2945-2949.
Siegers et al., "Hepatoprotection by Malotilate Against Carbon Tetrachloride-Alcohol Induced Liver Fibrosis," Inflammation Res. (1986) 18(5-6):600-603 (abstract only).
Sivakumar et al., "Upregulation of Lysyl Oxidase and MMPs During Cardiac Remodeling in Human Dilated Cardiomyopathy," Mol. Cell Biochem. (2008) 307(1-2):159-167.
Smith-Mungo et al., "Lysyl Oxidase: Properties, Regulation and Multiple Functions in Biology," Matrix Biol. (1998) 16:387-398.
Sommer et al., "Transient Expression of Lysyl Oxidase by Liver Myofibroblasts in Murine Schistosomiasis," Laboratory Investigation (1993) 69(4):460-470.
Sorensen et al., "Hypoxia-Induced Expression of Endogenous Markers In Vitro is Highly Influenced by pH," Radiotherapy and Oncology (2007) 83:362-366.
Stapleton et al., "Neutralization Escape Mutants Define a Dominant Immunogenic Neutralization Site on Hepatitis A Virus," Journal of Virology (1987) 61(2):491-498.
Stassar et al., "Identification of Human Renal Cell Carcinoma Associated Genes by Suppression Subtractive Hybridization," Br. J. Cancer (2001) 85(9):1372-1382.
Stassen, "Properties of Highly Purified Lysyl Oxidase from Embryonic Chick Cartilage," Biophys. Acta (1976) 438(1):49-60.
Stiffey-Wilusz et al., "An Ex Vivo Angiogenesis Assay Utilizing Commercial Porcine Carotid Artery: Modification of the Rat Aortic Ring Assay," Angiogenesis (2001) 4(1):3-9.
Szabo et al., "The Human Lysyl Oxidase-Like Gene Maps Between STS Markers D15S215 and GHLC.GCT7CO9 on Chromosome 15," Hum. Genet. (1997) 101(2):198-200.
Tamura et al., "Inhibition of Cell Migration, Spreading, and Focal Adhesions by Tumor Suppressor PTEN," Science (1998) 280:1614-1617 (Abstract).
Tang et al., "β-Substituted Ethylamine Derivatives as Suicide Inhibitors of Lysyl Oxidase," J. Biol. Chem. (1984) 259(2):975-979.
Tang et al., "Reaction of Aortic Lysyl Oxidase with Beta-Aminopropionitrile," J. Biol. Chem. (1983) 258(7):4331-4338.
Tarp et al., "Identification of a Novel Cancer-Specific Immunodominat Glycopeptide Epitope in the MUC1 Tandem Repeat," Glycobiology (2007) 17(2):197-209.
"The Role of the Extracellular Matrix in Cancer," Mar. 2001, U.S. Department of Energy: http:www.science.doe.gov/Accomplishments_Awards/Decades_Discovery/85.html.
Tockman et al., "Consideration in Bringing a Cancer Biomarker to Clinical Application," Cancer Res. (1992) 52:2711s-2718s.
Topp et al., "Antibody Transport in Cultured Tumor Cell Layers," J. Control. Release (1998) 53(1-3):15-23.
Trackman et al., "Cloning of Rat Aorta Lysyl Oxidase cDNA: Complete Codons and Predicted Amino Acid Sequence," Biochem. (1990) 29(20):4863-4870 and corrected page: Biochem. (1991) 30(33):8282.
Trackman et al., "Development of a Peroxidase-Coupled Fluorometric Assay for Lysyl Oxidase," Anal Biochem. (1981) 113(2):336-342.
Trackman et al., "Nonpeptidyl Amine Inhibitors are Substrates of Lysyl Oxidase," J. Biol. Chem. (1979) 254(16):7831-7836.
Trentham et al., "Autoimmunity to Type II Collagen: An Experimental Model of Arthritis," J. Experimental Medicine (1977) 146:857-868.
Trivedy et al., "The Upregulation of Lysyl Oxidase in Oral Submucous Fibrosis and Squamous Cell Carcinoma," J. Oral Pathol. Med. (1999) 28(6):246-251.
Van Lancker et al., "Patterns of Axillary Lymph Node Metastasis in Breast Cancer," Am. J. Clin. Oncol. (1995) 18(3):267-272 (Abstract).
Van Roy et al., "Invasiveness and Metastatic Capability of Rat Fibroblast-Like Cells Before and After Transfection with Immortalizing and Transforming Genes," Cancer Res. (1986) 46:4787-4795.

(56) References Cited

OTHER PUBLICATIONS

Vautherot et al., "Bovine Coronavirus Spike Glycoprotein: Localization of an Immunodominant Region at the Amino-Terminal End of S2," Journal of General Virology (1992) 73:3289-3294.
Waldmann, "Immunotherapy: Past, Present and Future," Nat. Med. (2003) 9(3):269-277.
Walling et al., "Aggressive Basal Cell Carcinoma: Presentation, Pathogenesis and Management," Cancer and Metastasis Reviews (2004) 23:389-402 (Abstract).
Wang et al., "Lysyl Oxidase Inhibition Reduces Rat Liver Fibrosis After Bile Duct Ligation," Gastroenterology & Digestive Disease Week Meeting—108th Annual Meeting of the American-Gastroenterological-Association, Washington, DC, May 19-24, 2007 (2007) 132(4):A827.
Watters et al., "Idiopathic Pulmonary Fibrosis: Pretreatment Bronchoalveolar Lavage Cellular Constituents and Their Relationships with Lung Histopathology and Clinical Response to Therapy," Am Rev. Respir. Dis. (1987) 135(3):696-704 (abstract only).
Weiner, "An Overview of Monoclonal Antibody Therapy of Cancer," Seminars Oncology (1999) 26(4):41-50.
Zhang et al., "Hypoxia Enhances Metastatic Efficiency in HT-1060 Fibrosarcoma Cells by Increasing Cell Survival in Lungs not Cell Adhesion and Invasion," Cancer Res. (2007) 67(18):7789-7797.
Zhu et al., "The Thin Prep Rat Aortic Ring Assay: A Modified Method for the Characterization of Angiogenesis in Whole Mounts," Angiogenesis (2002) 5(1-2):81-86.
Decision to Grant for EP 10012458.5 dated Sep. 12, 2013.
Search Report and Written Opinion for SN 201201215-9 mailed Jul. 19, 2013.
First Office Action (translation) for CN 201080047970.7 mailed Jul. 26, 2013.
Kraus et al. (2006) "CSMD1 Is a Novel Multiple Domain Complement-Regulatory Protein Highly Expressed in the Central Nervous System and Epithelial Tissues" J. Immunol. 176:4419-4430.
Final Office Action for U.S. Appl. No. 13/021,555 mailed Jul. 19, 2013.
Final Office Action for U.S. Appl. No. 12/860,834, mailed Jul. 26, 2013.
Final Office Action for U.S. Appl. No. 12/652,687, mailed Aug. 1, 2013.
Notice of Allowance (translation) for JP 2010-519263, mailed Jun. 21, 2013.
Advisory Action for U.S. Appl. No. 12/185,054 mailed Aug. 20, 2013.
Office Action (translation) for Japanese Application No. 2010-519951 mailed Jul. 12, 2013.
Decision on Rejection (translation) for CN 200880101321.3 mailed Jul. 3, 2013.
First Office Action (translation) for CN 201080047979.8 mailed Jun. 28, 2013.
Non-Final Office Action for U.S. Appl. No. 13/487,109 mailed Aug. 8, 2013.
American Thoracic Society International Consensus Statement (2000) "Idiopathic Pulmonary Fibrosis: Diagnosis and Treatment" Am J Respir Grit Care Med 161:646-664.
Peng et al. (2009) "Secreted LOXL2 is a Novel Therapeutic Target that Promotes Gastric Cancer Metastasis via the Src/FAK Pathway," Carcinogenesis 30(10):1660-1669.
Schietke et al. (2010) "The Lysyl Oxidases LOX and LOXL2 are Necessary and Sufficient to Repress E-cadherin in Hypoxia: Insights into Cellular Transformation Processes Mediated by HIF-1," Journal of Biological Chemistry 285(9):6658-6669 (Published, JBC Papers in Press, Dec. 21, 2009).
U.S. Appl. No. 12/860,632, filed Aug. 2010, Marshall et al.
U.S. Appl. No. 13/021,555, filed Feb. 2011, McCauley et al.
Office Action mailed Sep. 23, 2010 in U.S. Appl. No. 12/185,054.
Office Action mailed Feb. 15, 2011 in U.S. Appl. No. 12/185,054.
Office Action mailed Jan. 28, 2013 in U.S. Appl. No. 12/185,054.
International Preliminary Report on Patentability Chapter I issued Feb. 2, 2010, in PCT/US2008/009354.
Written Opinion of the ISA mailed Apr. 29, 2009, in PCT/US2008/009354.
International Search Report mailed Apr. 29, 2009, in PCT/US2008/009354.
Invitation to Pay Additional Fees mailed Jan. 14, 2009 (including Annex "Communication Relating to the Results of Partial International Search"), in PCT/US2008/009354.
Communication pursuant to Article 94(3) EPC dated Jun. 8, 2010, in EP 08795003.6-1222.
Communication pursuant to Article 94(3) EPC dated Jul. 19, 2011, in EP 08795003.6-1222.
Communication under Rule 71(3) EPC dated Jul. 23, 2012, in EP 08795003.6-1222.
Partial European Search Report for EP 12172214.4, mailed Nov. 28, 2012, 10 pages.
Patent Examination Report No. 1 for AU 2008282739, issued Nov. 19, 2012.
Office Action mailed Jun. 29, 2007, in U.S. Appl. No. 10/536,440.
Office Action mailed Mar. 28, 2008, in U.S. Appl. No. 10/536,440.
Office Action mailed Nov. 14, 2008, in U.S. Appl. No. 10/536,440.
Office Action mailed Jun. 26, 2009, in U.S. Appl. No. 10/536,440.
Office Action mailed Dec. 30, 2009, in U.S. Appl. No. 10/536,440.
Office Action mailed Jun. 28, 2010, in U.S. Appl. No. 10/536,440.
Office Action mailed Jul. 5, 2011, in U.S. Appl. No. 10/536,440.
Office Action mailed May 14, 2010, in U.S. Appl. No. 12/571,167.
Office Action mailed Nov. 5, 2010, in U.S. Appl. No. 12/571,167.
Office Action mailed Mar. 24, 2011, in U.S. Appl. No. 12/571,167.
Office Action mailed Jul. 28, 2011, in U.S. Appl. No. 12/571,167.
International Preliminary Examination Report mailed Dec. 8, 2003, in PCT/IL01/00728.
Written Opinion mailed Jun. 6, 2003, in PCT/IL01/00728.
International Search Report mailed Dec. 17, 2002, in PCT/IL01/00728.
Invitation to Pay Additional Fees mailed May 23, 2002, in PCT/IL01/00728.
International Search Report mailed Jan. 5, 2006, in PCT/IL03/01008.
Invitation to Pay Additional Fees mailed Jun. 13, 2005, in PCT/IL03/01008.
European Search Report mailed Jul. 29, 2005, in EP 01958338.4-2406.
Communication pursuant to Article 96(2) EPC mailed Nov. 14, 2005, in EP 01958338.4-2406.
Communication pursuant to Article 96(2) EPC mailed Jun. 25, 2007, in EP 01958338.4-2406.
Communication pursuant to Article 94(3) EPC mailed Feb. 10, 2009, in EP 01958338.4-2406.
European Search Report mailed Feb. 29, 2008, in EP 03777136.7-1222.
Communication pursuant to Article 94(3) EPC mailed May 29, 2008, in EP 03777136.7-1222.
European Search Report mailed Dec. 21, 2009, in EP 08020754.1-2402.
European Search Opinion mailed Dec. 21, 2009, in EP 08020754.1-2402.
Communication pursuant to Article 94(3) EPC mailed Oct. 22, 2010, in EP 08020754.1-2402.
Communication pursuant to Article 94(3) EPC mailed Mar. 15, 2011, in EP 08020754.1-2402.
European Search Opinion mailed Jun. 3, 2009, in EP 08020752.5-1222.
Communication pursuant to Article 94(3) EPC mailed Feb. 8, 2010, in EP 08020752.5-1222.
Communication pursuant to Article 94(3) EPC mailed Dec. 27, 2011, in EP 08020752.5-1222.
European Search Opinion mailed Jun. 3, 2009, in EP 08020753.3-1222.
Communication pursuant to Article 94(3) EPC mailed Dec. 27, 2011, in EP 08020753.3-1222.
European Search Report mailed Jun. 27, 2011, in EP 10012457.7-2406.
European Search Opinion mailed Jun. 27, 2011, in EP 10012457.7-2406.
Office Action mailed Sep. 23, 2010, in U.S. Appl. No. 12/185,050.

(56) References Cited

OTHER PUBLICATIONS

Office Action mailed Feb. 15, 2011, in U.S. Appl. No. 12/185,050.
Office Action mailed Nov. 26, 2012, in U.S. Appl. No. 13/204,336.
Office Action mailed Jan. 7, 2013, in U.S. Appl. No. 13/204,336.
International Preliminary Report on Patentability Chapter I issued May 11, 2010, in PCT/US2008/072039.
Written Opinion of the ISA mailed Jan. 13, 2009, in PCT/US2008/072039.
International Search Report mailed Jan. 13, 2009, in PCT/US2008/072039.
Communication pursuant to Article 94(3) EPC mailed Jun. 8, 2010, in EP 08830207.0-1222.
Communication pursuant to Article 94(3) EPC mailed Jul. 20, 2011, in EP 08830207.0-1222.
Communication pursuant to Article 94(3) EPC mailed Jul. 4, 2012, in EP 08830207.0-1222.
Communication pursuant to Article 94(3) EPC for EP 08 830 207.0, mailed Nov. 22, 2012.
European Search Report for EP 12172222.7, mailed Nov. 28, 2012, 15 pages.
Patent Examination Report No. 1 for AU 2008299784, mailed Dec. 12, 2012.
Notice on the Second Office Action (translation) for CN 200880101321.3, mailed Nov. 23, 2012.
Office Action mailed Jun. 14, 2011, in U.S. Appl. No. 12/652,687.
Office Action mailed Dec. 13, 2011, in U.S. Appl. No. 12/652,687.
Office Action mailed Mar. 30, 2012, in U.S. Appl. No. 12/652,687.
Advisory Action mailed Feb. 23, 2012, in U.S. Appl. No. 12/652,687.
Notice of Allowance mailed Sep. 18, 2012, in U.S. Appl. No. 12/652,687.
International Preliminary Report on Patentability Chapter I issued Jul. 12, 2011, in PCT/US2010/020159.
Written Opinion of the ISA mailed Sep. 9, 2010, in PCT/US2010/020159.
International Search Report mailed Sep. 9, 2010, in PCT/US2010/020159.
Office Action mailed Jan. 17, 2012, in U.S. Appl. No. 12/701,289.
Office Action mailed Jun. 15, 2012, in U.S. Appl. No. 12/701,289.
Office Action mailed Sep. 24, 2012, in U.S. Appl. No. 12/701,289.
Advisory Action mailed Aug. 30, 2012, in U.S. Appl. No. 12/701,289.
International Preliminary Report on Patentability Chapter I issued Aug. 9, 2011, in PCT/US2010/023359.
Written Opinion of the ISA mailed Apr. 15, 2010, in PCT/US2010/023359.
International Search Report mailed Apr. 15, 2010, in PCT/US2010/023359.
Communication pursuant to Rules 70(2) and 70a(2) EPC for EP 10739181.5, mailed Nov. 5, 2012.
Notice of Allowance for U.S. Appl. No. 12/860,625, mailed Nov. 23, 2012.
International Preliminary Report on Patentability Chapter I issued Feb. 21, 2012, in PCT/US2010/046192.
Written Opinion of the ISA mailed Feb. 17, 2011, in PCT/US2010/046192.
International Search Report mailed Feb. 17, 2011, in PCT/US2010/046192.
Invitation to Pay Additional Fees mailed Nov. 18, 2010, in PCT/US2010/046192.
Supplementary European Search Report for EP 10810673.3, mailed Nov. 26, 2012.
Examination Report for NZ 598466, mailed Nov. 5, 2012.
Office Action mailed Jul. 13, 2012, in U.S. Appl. No. 12/860,838.
International Preliminary Report on Patentability Chapter I issued Feb. 21, 2012, in PCT/US2010/046248.
Written Opinion of the ISA mailed Jan. 7, 2011, in PCT/US2010/046248.
International Search Report mailed Jan. 7, 2011, in PCT/US2010/046248.
Office Action mailed Jul. 12, 2012, in U.S. Appl. No. 12/860,693.
Final Office Action for U.S. Appl. No. 12/860,693, mailed Nov. 15, 2012.
International Preliminary Report on Patentability Chapter I issued Feb. 21, 2012, in PCT/US2010/046196.
Written Opinion of the ISA mailed Oct. 1, 2010, in PCT/US2010/046196.
International Search Report mailed Oct. 1, 2010, in PCT/US2010/046196.
Supplementary European Search Report for EP 10810675.8, mailed Dec. 4, 2012.
Examination Report for NZ 598456, mailed Nov. 6, 2012.
Office Action mailed May 29, 2012, in U.S. Appl. No. 12/860,632.
Office Action mailed Sep. 11, 2012, in U.S. Appl. No. 12/860,632.
International Preliminary Report on Patentability Chapter I issued Feb. 21, 2012, in PCT/US2010/046247.
Written Opinion of the ISA mailed Sep. 24, 2010, in PCT/US2010/046247.
International Search Report mailed Sep. 24, 2010, in PCT/US2010/046247.
Office Action mailed Dec. 22, 2011, in U.S. Appl. No. 12/892,574.
Office Action mailed Jun. 18, 2012, in U.S. Appl. No. 12/892,574.
Office Action mailed Aug. 31, 2012, in U.S. Appl. No. 12/892,574.
International Preliminary Report on Patentability Chapter I issued Apr. 3, 2012, in PCT/US2010/050542.
Written Opinion of the ISA mailed Nov. 29, 2010, in PCT/US2010/050542.
International Search Report mailed Nov. 29, 2010, in PCT/US2010/050542.
International Preliminary Report on Patentability Chapter I issued Aug. 7, 2012, in PCT/US2011/023791.
Written Opinion of the ISA mailed May 17, 2011, in PCT/US2011/023791.
International Search Report mailed May 17, 2011, in PCT/US2011/023791.
Non-Final Office Action for U.S. Appl. No. 12/860,834, mailed Jan. 10, 2013.
International Preliminary Report on Patentability Chapter I issued Feb. 21, 2012, in PCT/US2010/046244.
Written Opinion of the ISA mailed Feb. 8, 2011, in PCT/US2010/046244.
International Search Report mailed Feb. 8, 2011, in PCT/US2010/046244.
Invitation to Pay Additional Fees mailed Dec. 3, 2010, in PCT/US2010/046244.
Examination Report for NZ 598464, mailed Nov. 5, 2012.
Written Opinion of the ISA mailed Jun. 14, 2012, in PCT/US2012/032600.
International Search Report mailed Jun. 14, 2012, in PCT/US2012/032600.
Written Opinion of the ISA mailed Aug. 10, 2012, in PCT/US2012/037580.
International Search Report mailed Aug. 10, 2012, in PCT/US2012/037580.
Written Opinion of the ISA mailed Sep. 10, 2012, in PCT/US2012/040585.
International Search Report mailed Sep. 10, 2012, in PCT/US2012/040585.
Akagawa et al. (2007) "Systematic screening of Lysyl Oxidase-like (LOXL) family genes demonstrates that LOXL2 is a susceptibility gene to intracranial aneurysms." Hum Genet 121(3-4): 377-87.
Albini et al. (1987) "A Rapid In Vitro Assay for Quantitating the Invasive Potential of Tumor Cells" Cancer Res. 47(12):3239-3245.
Aplin et al. (1998) "Signal transduction and signal modulation by cell adhesion receptors: the role of integrins, cadherins, immunoglobulin-cell adhesion molecules, and selectins" Pharmacol Rev. 50(2):197-263.
Armstrong et al. (1999) "Changes in Collagen Turnover in Early Acute Respiratory Distress Syndrome," Am. J. Respir. Crit. Care Med. 160:1910-1915.
Atsawasuwan et al. (2008) "Lysyl Oxidase binds transforming growth factor-β and regulates its signaling via amine oxidase activity." J Biol Chem 283(49): 34229-40.

(56) References Cited

OTHER PUBLICATIONS

Barker et al. (2011) "LOXL2-mediated matrix remodeling in metastasis and mammary gland involution" Cancer Res., 71(5):1561-1572.
Barry-Hamilton et al. (2010) "Allosteric inhibition of Lysyl Oxidase-like-2 impedes the development of a pathologic microenvironment" Nat.Med. 19(9):1009-1017.
Bedogni et al. (2004) "Topical treatment with inhibitors of the phosphatidylinositol 3'-kinase/Akt and Raf/mitogen-activated protein kinase kinase/extracellular signal-regulated kinase pathways reduces melanoma development in severe combined immunodeficient mice" Cancer Res. 64(7):2552-2560.
Beilmann et al. (2004) "Human primary co-culture angiogenesis assay reveals additive stimulation and different angiogenic properties of VEGF and HGF" Cytokine 26(4):178-185.
Berger et al. (2004) "A murine model of ex vivo angiogenesis using aortic disks grown in fibrin clot" Microvascular Res. 68(3):179-187.
Bhowmick, et al. (2004). "Stromal fibroblasts in cancer initiation and progression." Nature 432(7015): 332-7.
BLAST 2 Sequences (LOR-1 and LOR-2) results version BLASTP 2.2.14, Apr. 9, 2006.
Boneberg, et. al. (2009) "Angiogenesis and lymphangiogenesis are downregulated in primary breast cancer" Br. J. Cancer, 101(4):605-614.
Bronson et al. (2005) "LOXL Null Mice Demonstrate Selective Dentate Structural Changes but Maintain Dentate Granule Cell and CA1 Pyramidal Cell Potentiation in the Hippocampus" Neurosci. Lett. 390(2):118-122.
Brukamp et al. (2007) "Hypoxia and Podocyte-Specific Vhlh Deletion Confer Risk of Glomerular Disease" Am. J. Physiol. Renal. Physiol. 293(4):F1397-F1407.
Butcher et al. (2009) "A Tense Situation: Forcing Tumour Progression" Nat. Rev. Cancer 9(2):108-122.
Castera (2011) "Invasive and Non-Invasive Methods for the Assessment of Fibrosis and Disease Progression in Chronic Liver Disease," Best Pract. Res. Clin. Gastroent. 25:291-303.
Chan et al. (2007) "Hypoxia, Gene Expression, and Metastasis" Cancer Metastasis Rev. 26(2):333-339.
Chang et al. (2004) "Gene expression signature of fibroblast serum response predicts human cancer progression: similarities between tumors and wounds" PLoS Biol. 2(2):206-213.
Chen (2005) "Boyden chamber assay" Methods Mol. Biol. 294:15-22.
Christiansen & Rajasekaran (2006) "Reassessing Epithelial to Mesenchymal Transition as a Prerequisite for Carcinoma Invasion and Metastasis" Cancer Res., 66(17):8319-26.
Chu & Peters (2008). "Serial analysis of the vascular endothelial transcriptome under static and shear stress conditions." Physiol Genomics 34(2): 185-92.
Chu et al. (2008) "Glycogen synthase kinase-3β regulates DeltaNp63 gene transcription through the β-catenin signaling pathway." J Cell Biochem 105(2): 447-53.
Chua et al., (2005) "Pulmonary Fibrosis Searching for Model Answers," Am J. Respir. Cell. Mol. Biol. 33:9-13.
Conti et al. (2008) "The desmoplastic reaction surrounding hepatic colorectal adenocarcinoma metastases aids tumor growth and survival via alphav integrin ligation." Clin Cancer Res 14(20): 6405-13.
Database EMBL [Online] Oct. 28, 2008, "Sequence 15133 from Patent WO2004061423", retrieved from EBI accession No. EMBL:FB530075, Database accession No. FB530075.
De Eguileor et al. (2004) "Hirudo medicinalis: avascular tissues for clear-cut angiogenesis studies?" Current Pharmaceutical Design 10(16):1979-1998.
Entrez Gene data base searching result in National Library of Medicine. 2010.
Erler et al. (2004) "The role of Hypoxia-Induced Lysyl Oxidase in Cancer Progression, Tumor Response to Therapy and Patient Prognosis" Eur. J. Cancer Suppl. 2(8):190.
Erler et al. (2006) "Lysyl Oxidase is Essential for Hypoxia-Induced Metastasis" Pro. Amer. Assoc. Cancer Res. 47:Abstract 2409.

Erler et al. (2006) "12 LOX is Essential for Hypoxia-Induced Metastasis" Radiother. Oncol. 78:S5.
Erler et al. (2009) "Hypoxia-induced lysyl oxidase is a Critical mediator of bone marrow cell recruitment to form the premetastatic niche." Cancer Cell 15(1): 35-44.
Gelatt (1977) "Animal models for glaucoma" Invest. Ophthalmol. Visual Sci. 16(7):592-596.
Görögh et al. (2007) "Selective Upregulation and Amplification of the Lysyl Oxidase Like-4 (LOXL4) Gene in Head and Neck Squamous cell Carcinoma" J. Pathol. 212(1):74-82.
Görögh et al. (2008). "Functional analysis of the 5' flanking domain of the LOXL4 gene in head and neck squamous cell carcinoma cells." Int J Oncol 33(5): 1091-8.
Greenbaum et al. (2003) "Comparing protein abundance and mRNA expression levels on a genomic scale", Genome Biology 40 (9):117. 01-117.08.
Grigorescu (2006) "Noninvasive Biochemical Markers of Liver Fibrosis," J. Gastrointestin. Liver Dis. 15(2):149-159.
Gulec et al. (2004) "A new in vitro assay for human tumor angiogenesis: three-dimensional human tumor angiogenesis assay" Ann. Surgical Oncology 11(1):99-104.
Ham et al. (2008) "144. Inhibition of an Extracellular Matrix Protein Increases Survival in Orthotopic Nude Mouse Models" J. Surg. Res. 144(2):239-240.
Hayashi et al. (2004) "Comparative immunocytochemical localization of Lysyl Oxidase (LOX) and the Lysyl Oxidase-like (LOXL) proteins: changes in the expression of LOXL during development and growth of mouse tissues." J Mol Histol 35(8-9): 845-55.
Hollosi et al. (2009) "Lysyl Oxidase-like 2 promotes migration in noninvasive breast cancer cells but not in normal breast epithelial cells." Int J Cancer 125(2):318-327.
Ishak et al. (1995) "Histological Grading and Staging of Chronic Hepatitis," J. Hepatol. 22:696-699.
Julien et al. (2008) "A reproducible and quantifiable model of choroidal neovascularization induced by VEGF a after subretinal adenoviral gene transfer in the rabbit" Molecular Vision 14: 1358-1372.
Kaiser et al. (2006) "Cancer. First pass at cancer genome reveals complex landscape" Science 313(5792):1370.
Kaku et al. (2007) "Post-translational modifications of collagen upon BMP-induced osteoblast differentiation." Biochem Biophys Res Commun 359(3): 463-8.
Kang et al. (2009) "Prosaposin Inhibits Tumor Metastasis Via Paracrine and Endocrine Stimulation of Stromal p53 and Tsp-1" Proc. Natl. Acad. Sci. U.S.A. 106(29):12115-12120.
Kim et al. (2003) "Expression and Purification of Enzymatically Active Forms of the Human Lysyl Oxidase-Like Protein 4" J. Biol. Chem. 278(52):52071-52074.
Klutke et al. (2008) "Decreased endopelvic fascia elastin content in uterine prolapse." Acta Obstet Gynecol Scand 87(1): 111-5.
Knodell et al. (1981) "Formulation and Application of a Numerical Scoring System for Assessing Histological Activity in Asymptomatic Chronic Active Hepatitis," Hepatol. 1(5):431-435.
Kragh et al. (2004) "A versatile in vivo chamber angiogenesis assay for measuring anti-angiogenic activity in mice" Oncology Reports 11(2):303-307.
Kresse et al. (2008) "DNA copy number changes in high-grade malignant peripheral nerve sheath tumors by array CGH." Mol Cancer 7: 48.
Laczko et al. (2007). "Active Lysyl Oxidase (LOX) correlates with focal adhesion kinase (FAK)/paxillin activation and migration in invasive astrocytes." Neuropathol Appl Neurobiol 33(6): 631-43.
Lelievre et al. (2008) "VE-statin/egfl7 regulates vascular elastogenesis by interacting with Lysyl Oxidases." EMBO J 27(12): 1658-70.
Li et al. (1999) "Liver Fibrogenesis and the Role of Hepatic Stellate Cells: New Insights and Prospects for Therapy," J. of Gastroentero. and Hepatol. 14:618-633.
Li, et al. (2007) "Tumor microenvironment: the role of the tumor stroma in cancer." J Cell Biochem 101(4): 805-15.
Lucero & Kagan (2006) "Lysyl Oxidase: an oxidative enzyme and effector of cell function." Cell Mol Life Sci 63(19-20): 2304-16.

(56) References Cited

OTHER PUBLICATIONS

Lugassy et al. (2012) "The Enzymatic Activity of Lysyl Oxidase-like-2 (LOXL2) Is Not Required for LOXL2-induced Inhibition of Keratinocyte Differentiation", Journal of Biological Chemistry 287(5):3541-3549.
MaCartney-Coxson et al. (2008) "Metastatic susceptibility locus, an 8p hot-spot for tumour progression disrupted in colorectal liver metastases: 13 candidate genes examined at the DNA, mRNA and protein level." BMC Cancer 8: 187.
Maier et al. (2009) "Correlation of mRNA and protein in complex biological samples", FEBS Letters 583 (24):3966-3973.
Manns et al. (2011) "A Phase-2B Trial to Evaluate the Safety, Tolerability and Efficacy of a Caspase Inhibitor, GS-9450, in Adults Failing PEG/RBV Therapy for Chronic HCV Infection," J Hepatology. (2011) 54 Supplement 1: S55-S56.
McKechnie et al. (2003) "Hr44 Secreted wtih exosomes: Loss from Ciliary epithelium in response to inflammation" IOVS 44(6): 2650-2656.
Mehal et al. (2011) "Expressway to the Core of Fibrosis," Nat. Med. 17(5):552-553.
Miller et al. (2004) "A novel technique for quantifying changes in vascular density, endothelial cell proliferation and protein expression in response to modulators of angiogenesis using the chick chorioallantoic membrane (CAM) assay" J. Translational Med. 2(1):4.
Molnar et al. (2005) "*Drosophila* Lysyl oxidases Dmloxl-1 and Dmloxl-2 are differentially expressed and the active DmLOXL-1 influences gene expression and development." J Biol Chem 280(24): 22977-85.
Monticone et al. (2004) "Gene expression profile of human bone marrow stromal cells determined by restriction fragment differential display analysis." J Cell Biochem 92(4): 733-44.
Morbidelli et al. (2004) "The rabbit corneal pocket assay for the study of angiogenesis" Cancer Treatment Res. 117:147-151.
Müller et al. (2006) "Lung fibroblasts from patients with emphysema show markers of senescence in vitro." Respir Res 7: 32.
Nagaoka et al. (2008) "1,25(OH)2D3 regulates collagen quality in an osteoblastic cell culture system." Biochem Biophys Res Commun 377(2): 674-8.
Nakken et al. (2007) "Multiple inflammatory-, tissue remodelling- and fibrosis genes are differentially transcribed in the livers of Abcb4 (−/−) mice harbouring chronic cholangitis." Scand J Gastroenterol 42(10): 1245-55.
NCBI dbSNP record for LOXL2, available at http://www.ncbi.nlm.nih.gov/projects/SNP/snp_ref.cqi?locusId=4017, retrieved Apr. 19, 2012.
Noblesse et al. (2004) "Lsyl Oxidase-like and lysysl oxidase are present in the dermis and epidermis of a skin equivalent and in himan skin and are associate to elastic fibers" J. Investig. Dermatol., 122:621-630.
Norrby (2006) "In vivo models of angiogenesis" J. Cell. Mol. Med. 10(3):588-612.
Ogata et al. (1996) "Changes in alveolar capillary formation in growing rat lung by repeated injections of a lathyrogen" Growth, Development and Aging 60:153-160.
Pascal et al. (2005) "Comparison of replicative senescence and stress-induced premature senescence combining differential display and low-density DNA arrays." FEBS Lett 579(17): 3651-9.
Payne et al. (2007) "Paradoxical roles for lysyl oxidases in cancer—a prospect." J Cell Biochem 101(6): 1338-54.
Peinado et al. (2005) "Switching on-off Snail: LOXL2 versus GSK3β." Cell Cycle 4(12): 1749-52.
Polgar et al. (2007) "Lysyl Oxidase interacts with hormone placental lactogen and synergistically promotes breast epithelial cell proliferation and migration." J Biol Chem 282(5): 3262-72.
Portolano et al. (1993) "Lack of Promiscuity in Autoantigen-Specific H and L Chain Combinations as Revealed by Human H and L Chain 'Roulette'". J Immunol 150(3):880-887.
Postovit et al. (2008) "Hypoxia/reoxygenation: a dynamic regulator of Lysyl Oxidase-facilitated breast cancer migration." J Cell Biochem 103(5): 1369-78.

Pouysségur et al. (2006) "Hypoxia Signalling in Cancer and Approaches to Enforce Tumour Regression" Nature 441(7092):437-443.
Reed et al. (2007) "Culture of murine aortic explants in 3-dimensional extracellular matrix: a novel, miniaturized assay of angiogenesis in vitro" Microvascular Res. 73(3):248-252.
Ribatti (2004) "The first evidence of the tumor-induced angiogenesis in vivo by using the chorioallantoic membrane assay dated 1913" Leukemia 18(8):1350-1351.
Rodriguez et al. (2010) "Modulation of Lysyl Oxidase-like 2 enzymatic activity by an allosteric antibody inhibitor" J. Biol. Chem. 285:20964-20974.
Roskoski (2007) "Vascular endothelial growth factor (VEGF) signaling in tumor progression" Critical Reviews in Oncology/Hematology 62: 179-213.
Ruckert et al. (2009) "Functional analysis of LOXL2 in pancreatic carcinoma" International Journal of Colorectal Disease; Clinical and Molecular Gastroenterology and Surgery, Springer, Berlin, DE, 25(3):303-311.
Salnikow et al. (2008) "Regulation of hypoxia-inducible genes by ETS1 transcription factor." Carcinogenesis 29(8): 1493-9.
Schena et al. (2005) "Pathogenic Mechanisms of Diabetic Nephropathy," J. Am. Soc. Nephrol. 16:S30-S33.
Scheuer (1991) "Classification of Chronic Viral Hepatitis: A Need for Reassessment," J. Hepatol. 13:372-374.
Schlotzer-Schrehardt et al. (2008) "Genotype-correlated expression of Lysyl Oxidase-like 1 in ocular tissues of patients with pseudoexfoliation syndrome/glaucoma and normal patients." Am J Pathol 173(6): 1724-35.
Schmidt et al. (2007) "[Mapping of a deletion interval on 8p21-22 in prostate cancer by gene dosage PCR]." Verh Dtsch Ges Pathol 91: 302-7.
Sebban et al. (2009) "Lysyl Oxidase-like 4 is alternatively spliced in an anatomic site-specific manner in tumors involving the serosal cavities." Virchows Arch 454(1): 71-9.
Selman et al. (2005) "Gene Expression Profiles Distinguish Idiopathic Pulmonary Fibrosis from Hypersensitivity Pneumonitis" Am. J. Respir. Crit.Care Med. 173(2):188-198.
Sequence search result (Neufeld) 2010.
Sheppard (2006) "Transforming Growth Factor β: A Central Modulator of Pulmonary and Airway Inflammation and Fibrosis" Proc. Am. Thorac. Soc. 3(5):413-417.
Siemann et al. "Tumor Vasculature: a Target for Anticancer Therapies" in: "Vascular-Targeted Therapies in Oncology", Mar. 10, 2006, John Wiley & Sons. Ltd. Chichester, UK.
Sion et al. (2006) "Lysyl Oxidase (lox) and hypoxia-induced metastases" Cancer Biology & Therapy, 5(8):909-911.
Szauter et al. (2005) "Lysyl Oxidase in development, aging and pathologies of the skin." Pathol Biol (Paris) 53(7): 448-56.
Thiery et al. (2003) "Epithelial-Mesenchymal Transitions in Development and Pathologies" Curr. Opin. Cell. Biol. 15(6):740-6.
Thomassin et al. (2005) "The Pro-Regions of Lysyl Oxidase and Lysyl Oxidase-Like 1 Are Required for Deposition onto Elastic Fibers" J Biol. Chem. Dec. 30, 2005; 280(52):42848-55.
Tzortzaki et al. (2006) "Active Remodeling in Idiopathic Interstitial Pneumonias: Evaluation of Collagen Types XII and XIV," J. Histochem. & Cytochem. 54(6):693-700.
Understanding Cancer Series: Cancer Slide 8: Invasion and Metastasis, www.cancer.gov/cancertopics/understandingcancer/cancer/slide8, (2009).
Vadasz et al. (2005) "Abnormal deposition of collagen around hepatocytes in Wilson's disease is associated with hepatocyte specific expression of lysyl oxidase and lysyl oxidase like protein-2." J Hepatol 43(3): 499-507.
Van Bergen et al. "The role of LOXa nd LOXL2 in wound healing after glaucoma filtration surgery", European association for vision and eye research, Oct. 8, 2010, Retrieved from the Internet: URL:http://www.ever.be/view_abstract.php?abs_id=5411.
Walters & Kleeberger (2008) "Mouse Models of Bleomycin-Induced Pulmonary Fibrosis" Current Protocols Pharmacol. 40:5.46.1-5.46.17.

(56) References Cited

OTHER PUBLICATIONS

Watanabe et al. (2010) "Nucleolin as cell surface receptor for tumor necrosis factor-alpha inducing protein: a carcinogenic factor of *Helicobacter pylori*", Journal of Cancer Research and Clinical Oncology 136(6):911-921.
Weise et al. (2008) "LOXL4 is a selectively expressed candidate diagnostic antigen in head and neck cancer." Eur J Cancer 44.
Whaley-Connell et al. (2006) "Chronic Kidney Disease and the Cardiometabolic Syndrome," J. Clin. Hypert. 8(8):546-548.
Wu et al. (2007) "LOXL1 and LOXL4 are Epigenetically Silenced and Can Inhibit Ras/Extracellular Signal-Regulated Kinase Signaling Pathway in Human Bladder Cancer" Cancer Res. 67(9):4123-4129.

* cited by examiner

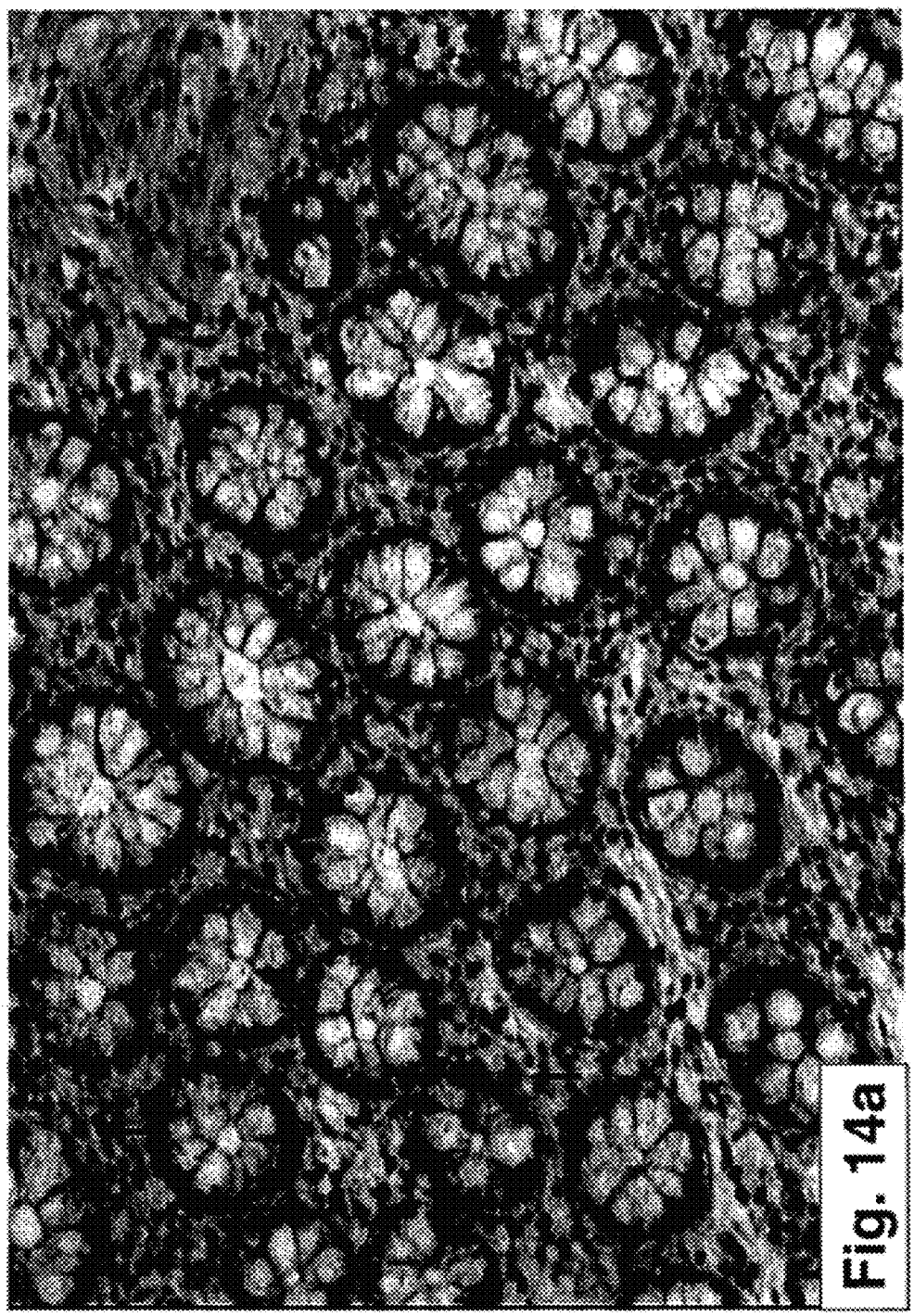

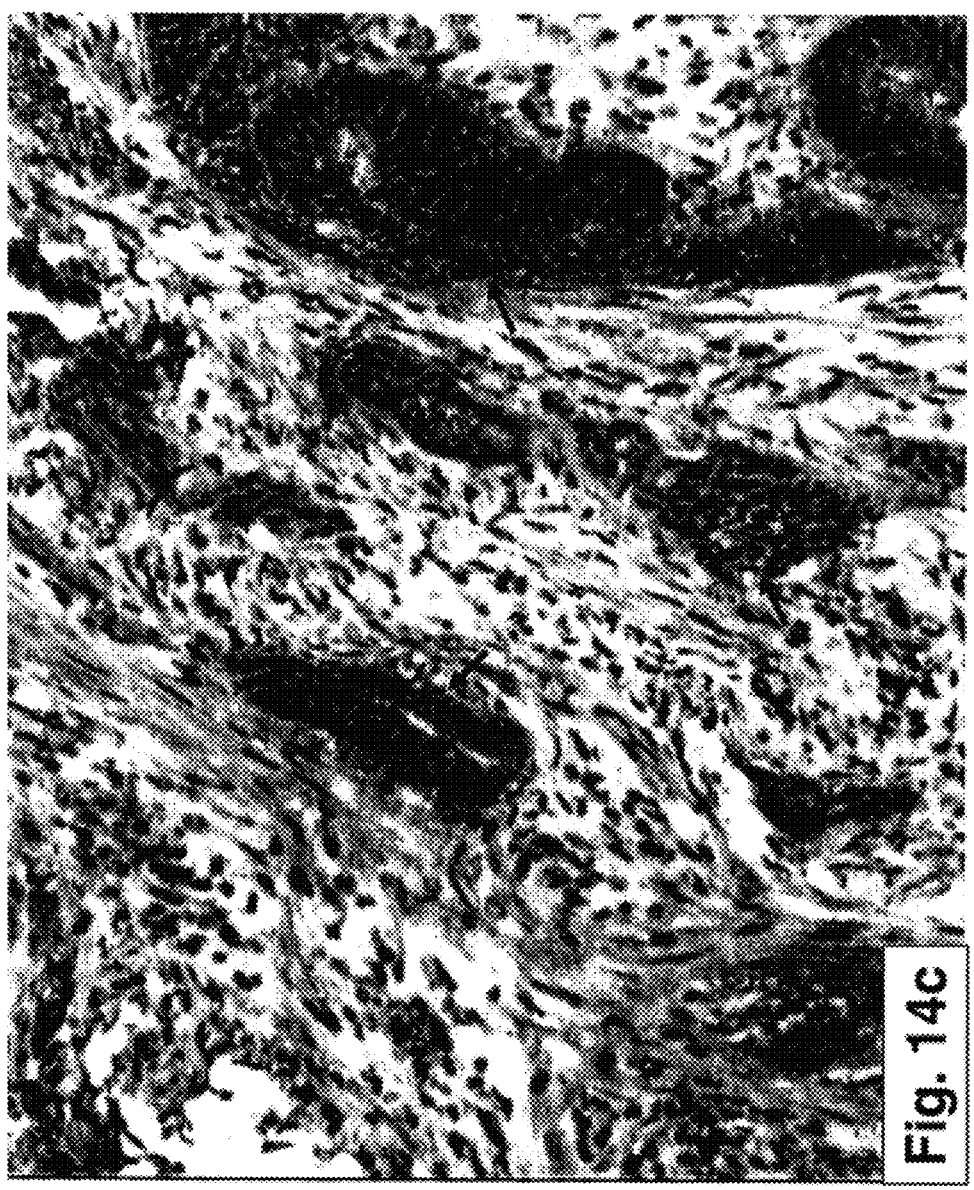

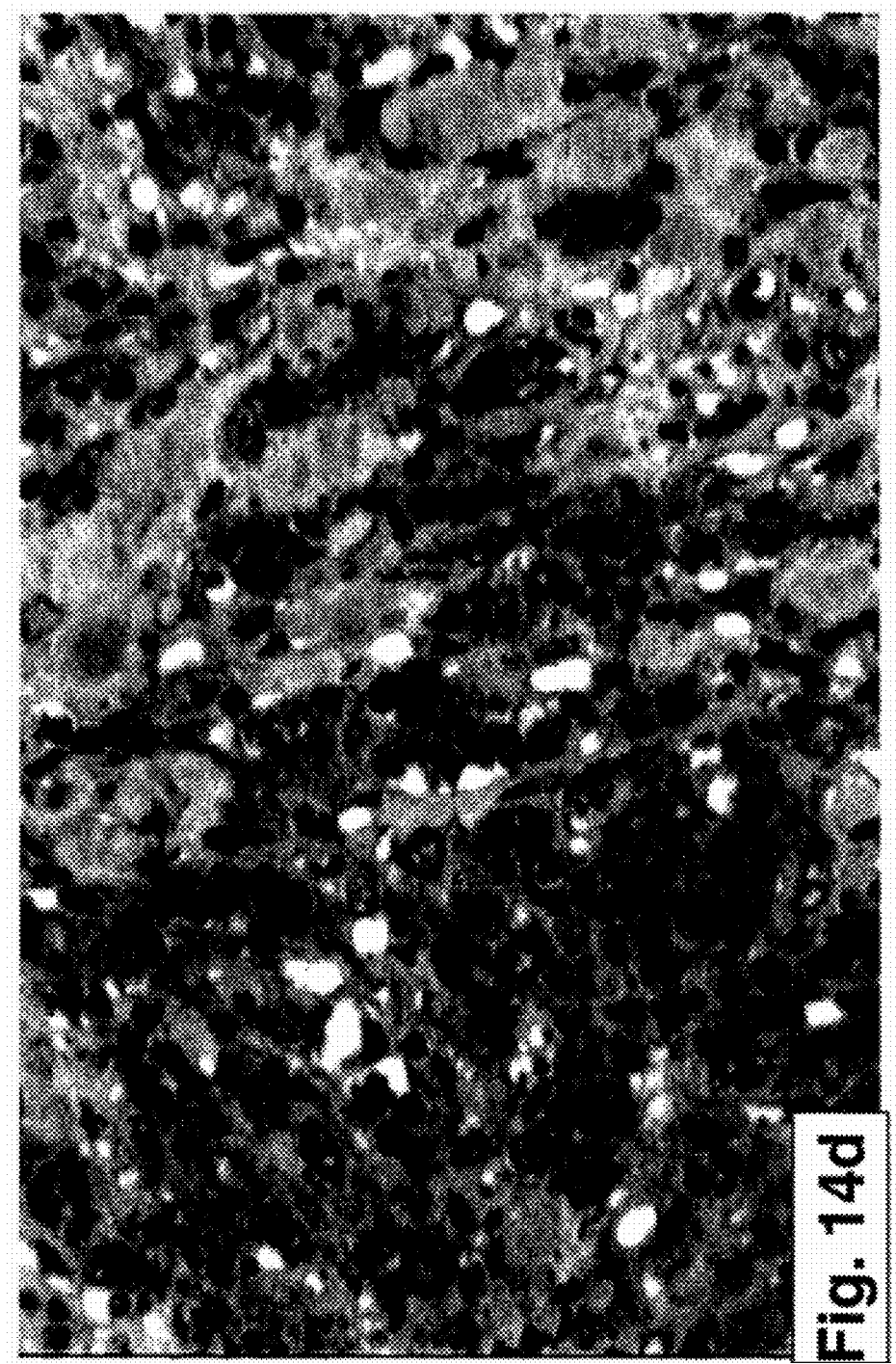

PHARMACEUTICAL COMPOSITIONS AND METHODS USEFUL FOR MODULATING ANGIOGENESIS, INHIBITING METASTASIS AND TUMOR FIBROSIS, AND ASSESSING THE MALIGNANCY OF COLON CANCER TUMORS

RELATED PATENT APPLICATIONS

This application is a divisional of U.S. patent application Ser. No. 12/571,167, filed 30 Sep. 2009, now allowed, which is a divisional of pending U.S. patent application Ser. No. 10/536,440, filed 14 Nov. 2005, now allowed, which is a national phase application of PCT/IL03/01008 having an international filing date of 27 Nov. 2003, which claims benefit of U.S. patent application Ser. No. 10/305,348, filed 27 Nov. 2002, now abandoned. The entire contents of these applications are incorporated herein by this reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 246102006712Seqlist.txt | Mar. 8, 2012 | 45,009 bytes |

FIELD AND BACKGROUND OF THE INVENTION

The present invention relates to pharmaceutical compositions and methods useful for modulating angiogenesis and for inhibiting metastasis and fibrosis in a mammalian tissue. The present invention further relates to a method of assessing the malignancy of colon tumors and predicting the prognosis of colon cancer.

Angiogenesis

In an adult, formation of new blood vessels in normal or diseased tissues is regulated by two processes, recapitulated vasculogenesis (the transformation of pre-existing arterioles into small muscular arteries) and angiogenesis, the sprouting of existing blood vessels (which occurs both in the embryo and in the adult).

The process of angiogenesis is regulated by biomechanical and biochemical stimuli. Angiogenic factors such as vascular endothelial growth factor (VEGF) and basic fibroblast growth factor (bFGF) are released by vascular cells, macrophages, and cells surrounding blood vessels. These angiogenic factors activate specific proteases that are involved in degradation of the basement membrane. As a result of this degradation, vascular cells migrate and proliferate thus leading to new blood vessel formation. Peri-endothelial cells, such as pericytes in the capillaries, smooth muscle cells in larger vessels and cardiac myocytes in the heart are recruited to provide maintenance and modulatory functions to the forming vessel.

The establishment and remodeling of blood vessels is controlled by paracrine signals, many of which are mediated by protein ligands which modulate the activity of transmembrane tyrosine kinase receptors. Among these molecules are vascular endothelial growth factor (VEGF) and its receptor families (VEGFR-1, VEGFR-2, neuropilin-1 and neuropilin-2), Angiopoietins 1-4 (Ang-1, Ang-2 etc.) and their respective receptors (Tie-1 and Tie-2), basic fibroblast growth factor (bFGF), platelet derived growth factor (PDGF), and transforming growth factor $\beta$(TGF-$\beta$).

The growth of solid tumors is limited by the availability of nutrients and oxygen. When cells within solid tumors start to produce angiogenic factors or when the levels of angiogenesis inhibitors decline, the balance between anti-angiogenic and angiogenic influences is perturbed, initiating the growth of new blood vessels from the existing vascular bed into the tumor. This event in tumor progression is known as the angiogenic switch (Folkman, 1990; Hanahan and Folkman 1996). It had been demonstrated that inhibitors of tumor angiogenesis are able to completely inhibit tumor growth in mice (Boehm et al., 1997; Bergers et al., 1999) and also inhibit tumor metastasis, a process that relies upon close contact between the vasculature and tumor cells (Zetter, 1998). It has also been demonstrated that angiogenesis plays an important role in the progression of breast cancer (Weidner, N. 1998; Degani et al., 1997; Guidi et al., 1997; Balsari et al., 1999).

Such findings have prompted the use of known anti-angiogenic factors in breast cancer therapy (Klauber et al., 1997; Harris et al., 1996; Weinstatsaslow et al., 1994) and a search for novel angiogenesis inhibitors.

During the past decade several novel inhibitors of angiogenesis have been isolated including inhibitors of VEGF signaling (Neufeld et al., 1999) and inhibitors of processes which lead to the maturation and stabilization of new blood vessels. Anti-integrin antibodies have been used as inhibitors of blood vessel maturation (Brooks et al., 1994; Brooks et al., 1998).

Although several anti-angiogenic drugs are now available commercially, the anti-angiogenic mechanisms of most of these drugs (e.g., angiostatin and endostatin) remain unclear (O'Reilly et al., 1997; Oreilly et al., 1996).

Since angiogenesis can be initiated by many (possibly compensatory) angiogenic factors it stands to reason that anti-angiogenic factors which target later processes in the angiogenic response such as vessel maturation or a combination of anti-angiogenic factors would be most effective in arresting vessel formation.

Platelet factor-4 (PF4) is an anti-angiogenic protein normally sequestered in platelets (Tanaka et al., 1997; Maione et al., 1990; Neufeld et al., 2000). PF4 inhibits angiogenesis using poorly defined mechanisms (Gengrinovitch et al., 1995; Brown, and Parish, 1994; Gupta, and Singh, 1994; Watson et al., 1994). It was previously speculated that PF4 binds to cell surface heparan-sulfate proteoglycans and in this manner inhibits the activity of angiogenic growth factors such as basic fibroblast growth factor (Watson et al., 1994).

Tumor Metastasis and Staging

The transition from a localized tumor to an invasive and metastatic tumor represents a landmark in the development of malignant disease, since it is usually associated with a markedly worse prognosis. The understanding of the processes that govern this transition is therefore of prime importance.

Breast Cancer

In breast cancer, the transition from a localized to an invasive/metastatic tumor is associated in many cases with the formation of fibrotic foci and desmoplasia, which is the presence of unusually dense collagenous stroma, within the primary tumor (Colpaert et al., 2001; Hasebe et al., 2000). A similar correlation may exist in other types of cancers such as colon and pancreatic cancers (Nishimura et al., 1998; Ellenrieder et al., 2000). These observations represent apparent paradoxes at first glance, since invasiveness has long been associated with the destruction of extracellular matrix by extracellular matrix degrading enzymes like metalo-proteases (Stamenkovic, 2000; Duffy et al., 2000) and heparanase (Vlodaysky and Friedmann, 2001). However, it is possible that deposition of excess extracellular matrix may stimulate in turn expression of matrix degrading enzymes that will contribute under certain circumstances to tumor invasion. In fact, there is some evidence that an increase in extracellular matrix deposition can indeed influence the production of extracellular matrix degrading enzymes (Schuppan et al., 2001; Swada et al., 2001).

Several prior art studies have attempted to develop agents to treat breast cancer metastases (Sauer et al., 2002) including a study by Kim et al., (2000) that described apicidin [cyclo (N—O-methyl-L-tryptophanyl-L-isoleucinyl-D-pipecolinyl-L-2-amino-8-oxodecanoyl)], a fungal metabolite that was identified as an antiprotozoal agent known to inhibit parasite histone deacetylase (HDAC), that can inhibit the H-ras-induced invasive phenotype of MCF10A human breast epithelial cells. Another agent is the polymeric form of fibronectin that was shown to reduce tumor growth and to posses antimetastatic activity when administered systemically to tumor-bearing mice (Yi and Ruoslahti, 2001).

Colon Cancer

Cancer of the gastrointestinal (GI) tract, especially colon cancer, is a highly treatable and often a curable disease when localized to the bowel. Surgery is the primary treatment and results in cure in approximately 50% of patients. Recurrence following surgery is a major problem and often is the ultimate cause of death. Nearly all cases of colorectal cancer arise from adenomatous polyps, some of which mature into large polyps, undergo abnormal growth and development, and ultimately progress into cancer. This progression would appear to take at least 10 years in most patients, rendering it a readily treatable form of cancer if diagnosed early, when the cancer is localized.

The standard procedures currently used for establishing a definitive diagnosis for a GI tract cancer include barium studies, endoscopy, biopsy and computed tomography [M. F. Brennan, et al. In: Cancer: Principles and Practice of Oncology, Fourth Edition, pp. 849-882, Philadelphia, Pa.: J. B. Lippincott Co. (1993)].

The prognosis of colon cancer is clearly related to the degree of penetration of the tumor through the bowel wall and the presence or absence of nodal involvement. These two characteristics form the basis for all staging systems developed for this disease. Staging is usually performed by a pathologist on tissue sections obtained via biopsy and/or surgery and it aims to determine the anatomic extent of the disease. Accurate staging is critical for predicting patient outcome and providing criteria for designing optimal therapy. Inaccurate staging can result in poor therapeutic decisions and is a major clinical problem in colon cancer.

Thus, to increase the accuracy of therapy and the survival rate of colon cancer patients there is a need to develop sensitive and accurate methods of staging of colon cancer.

SUMMARY OF THE INVENTION

While reducing the present invention to practice, the present inventors have uncovered a novel PF4 binding protein, a lysyl oxidase protein, LOR-1, which participates in modulating angiogenesis and breast cancer metastases and as such can be used as a target for inhibiting metastasis and reducing tumor invasiveness. Moreover, the present inventors have uncovered that the expression of LOR-1 is correlated with colon cancer progression and as such can be used for accurate staging of colon cancer.

According to one aspect of the present invention there is provided a method of modulating angiogenesis in a mammalian tissue, the method comprising administering into the mammalian tissue a molecule capable of modifying a tissue level and/or activity of at least one type of lysyl oxidase to thereby modulate angiogenesis in the mammalian tissue.

According to another aspect of the present invention there is provided a method of modulating angiogenesis in a mammalian tissue, the method comprising administering into the mammalian tissue a nucleic acid construct being capable of expressing a polypeptide having lysyl oxidase activity to thereby modulate angiogenesis within the mammalian tissue.

According to yet another aspect of the present invention there is provided a pharmaceutical composition useful for modulating angiogenesis in mammalian tissue comprising, as an active ingredient, a molecule capable of modifying a level and/or activity of at least one type of lysyl oxidase of the mammalian tissue and a pharmaceutically effective carrier.

According to another aspect of the present invention there is provided a method of modulating angiogenesis in a mammalian tissue, the method comprising administering into the mammalian tissue a molecule capable of modifying a tissue level and/or activity of a polypeptide at least 75% homologous to the polypeptide set forth in SEQ ID:2 or 9 to thereby modulate angiogenesis within the mammalian tissue.

According to further features in preferred embodiments of the invention described below, the molecule is an antibody or an antibody fragment capable of binding with, and at least partially inhibiting the activity of, the at least one polypeptide.

According to still further features in the described preferred embodiments the antibody or the antibody fragment is directed against at least a portion of the polypeptide set forth in SEQ ID NO:2, 3, 6, 8 or 9.

According to still further features in the described preferred embodiments the molecule is a polynucleotide capable of down regulating expression of the at least one type of lysyl oxidase.

According to still further features in the described preferred embodiments the polynucleotide is at least partially complementary with the polynucleotide set forth in SEQ ID NO:1, 4, 5 or 7.

According to still further features in the described preferred embodiments the molecule is a polypeptide having lysyl oxidase activity.

According to still further features in the described preferred embodiments the polypeptide is as set forth in SEQ ID NO:2, 3, 6, 8 or 9.

According to another aspect of the present invention there is provided a method of modulating angiogenesis in a mammalian tissue, the method comprising administering into the mammalian tissue a nucleic acid construct being capable of expressing a polypeptide having lysyl oxidase activity to thereby modulate angiogenesis within the mammalian tissue.

According to still further features in the described preferred embodiments the polypeptide is at least 75% homologous to the polypeptide set forth in SEQ ID NO:2, 3, 6, 8 or 9.

According to still another aspect of the present invention there is provided method of identifying molecules capable of modulating angiogenesis, the method comprising: (a) isolating molecules which exhibit specific reactivity with at least one type of lysyl oxidase; and (b) testing the molecules within mammalian tissue so as to determine the angiogenesis modulation activity thereof.

According to still further features in the described preferred embodiments step (a) is effected by binding assays and/or lysyl oxidase activity assays.

According to an additional aspect of the present invention there is provided method of determining the malignancy of cancerous tissue, the method comprising (a) determining a lysyl oxidase expression level and/or activity of the cancerous tissue; and (b) comparing the lysyl oxidase expression level and/or activity with that determined for control tissue to thereby determine the malignancy of the cancerous tissue.

According to another aspect of the present invention there is provided method of inhibiting metastasis and fibrosis in a mammalian tissue, the method comprising administering into the mammalian tissue a molecule capable of downregulating a tissue level and/or activity of at least one type of lysyl oxidase to thereby inhibit metastasis in the mammalian tissue According to still another aspect of the present invention there is provided a pharmaceutical composition useful for inhibiting metastasis and fibrosis in mammalian tissue comprising, as an active ingredient, a molecule capable of down-regulating a level and/or activity of at least one type of lysyl oxidase of the mammalian tissue and a pharmaceutically effective carrier.

According to further features in preferred embodiments of the invention described below, the molecule is an antibody or an antibody fragment capable of binding with, and at least partially inhibiting the activity of, the at least one polypeptide.

According to still further features in the described preferred embodiments the antibody or the antibody fragment is directed against at least a portion of the polypeptide set forth in SEQ ID NO:2, 3, 6, 8 or 9.

According to still further features in the described preferred embodiments the molecule is a polynucleotide capable of downregulating expression of the at least one type of lysyl oxidase.

According to still further features in the described preferred embodiments the polynucleotide is at least partially complementary with the polynucleotide set forth in SEQ ID NO:1, 4, 5 or 7.

According to still another aspect of the present invention there is provided method of identifying molecules capable of inhibiting metastasis and fibrosis, the method comprising: (a) screening and identifying molecules which exhibit specific reactivity with at least one type of lysyl oxidase; and (b) testing the metastasis and fibrosis inhibitory potential of the said molecules.

According to still further features in the described preferred embodiments step (a) is effected by binding assays and/or lysyl oxidase activity assays.

According to yet another aspect of the present invention there is provided a method for inhibiting metastasis and fibrosis in a mammalian tissue, the method comprising administering to the mammalian tissue a molecule capable of downregulating a tissue level and/or activity of a polypeptide at least 75% homologous to the polypeptide set forth in ID NO: 2 or 9, to thereby inhibit metastasis and fibrosis in a mammalian tissue.

According to yet another aspect of the present invention there is provided a method of assessing a malignancy of a colon tumor comprising determining a tissue level and/or an activity level of a polypeptide at least 75% homologous to the polypeptide set forth in SEQ ID NO:2 or 9 in a tissue of the colon tumor, thereby assessing the malignancy of the colon tumor.

According to yet another aspect of the present invention there is provided a method of predicting a prognosis of an individual diagnosed with colon cancer comprising: (a) obtaining a colon tumor tissue from the individual, and; (b) determining a tissue level and/or an activity level of a polypeptide at least 75% homologous to the polypeptide set forth in SEQ ID NO:2 or 9 in the colon tumor tissue to thereby assess the malignancy of the colon tumor tissue and predict the prognosis of the individual diagnosed with colon cancer.

According to still further features in the described preferred embodiments the tissue of the colon tumor is obtained using a colon biopsy and/or a colon surgery.

According to still further features in the described preferred embodiments determining the tissue level of the polypeptide is effected by an immunological detection method and/or an RNA detection method.

According to still further features in the described preferred embodiments determining the activity level of the polypeptide is effected by an enzymatic activity detection method.

According to still further features in the described preferred embodiments the immunological detection method is selected from the group consisting of a radio-immunoassay (RIA), an enzyme linked immunosorbent assay (ELISA), a Western blot analysis, and an immunohistochemical analysis.

According to still further features in the described preferred embodiments the RNA detection method is selected from the group consisting of a Northern blot analysis, an RNA in situ hybridization stain, an RT-PCR analysis, and an in situ RT-PCR stain.

According to still further features in the described preferred embodiments the enzymatic activity detection method is selected from the group consisting of a cytochemical stain, an in vitro activity assay, and an activity gel.

According to still further features in the described preferred embodiments the malignancy of the colon tumor is assessed by comparing the tissue level and/or the activity level of the polypeptide in the tissue of the colon tumor with a tissue level and/or activity level of the polypeptide in a normal colon tissue.

The present invention successfully addresses the shortcomings of the presently known configurations by providing pharmaceutical compositions and methods that can be used to treat metastatic cancer, formation of tumor fibrosis and other disorders characterized by excessive or insufficient blood vessel formation as well as by providing a method of assessing the malignancy of colon cancer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 10b illustrates post-translational processes of LOR-1. MCF-7/Tet-LOR1 cells grown in the presence of tetracycline were trypsinized and seeded into a 24-well dish ($5 \times 10^4$ cells/well) in a serum free medium in the absence of tetracycline. Cell aliquots collected at the noted times following tetracycline removal and were analyzed for the presence of LOR-1 by Western blot as described in FIG. 10a.

FIG. 11c illustrates human keratin-7 immunostaining of tumors generated by MCF-7 cells transfected with expression vector containing clone 12. Counter staining was performed with Hematoxylin-eosin (blue). Arrow points to nuclei of host cells concentrated in the fibrotic foci. No necrosis can be seen; magnification ×40. FIGS. 11d-f illustrate collagen deposits in tumor cells as viewed by Masson's Trichrome stain. A few collagen deposits are seen in tumors generated from MCF-7 cells transfected with the expression vector alone (FIG. 11d, arrows, magnification ×200). Thick collagen bundles are seen between tumor cells generated from MCF-7 cells transfected with expression vector containing clone 12 (FIG. 11e, magnification ×200). The fibrotic area is full with collagen fibers and interspaced with host derived cells in tumors generated from MCF-7 cells transfected with expression vector containing clone 24 (FIG. 11f, magnification ×200). FIGS. 11g-h illustrate blood vessels stained with Masson's Trichrome in tumors generated from MCF-7 cells transfected with the expression vector alone (FIG. 11g) or expression vector containing clone 12 (FIG. 11h); magnification ×400.

FIGS. 14a-d illustrate the expression pattern of LOR-1 in normal human colon (FIG. 14a), in a colon tumor including hyperplasia (FIG. 14b, diamond arrows) and adenoma (FIG. 14b, circled arrows), in a low-grade colon adenocarcinoma (FIG. 14c, arrows, brown stain) and in a high-grade colon adenocarcinoma (FIG. 14d, brown stain). A polyclonal affinity purified rabbit antibody directed against the C-terminal of LOR-1 was used to detect the expression of LOR-1 by immunohistochemistry in tissue sections obtained from various colon cancer tumors. Note the faint LOR-1 staining in a few cells of the normal colon (FIG. 14a, arrows, magnification ×10), the moderate LOR-1 staining in hyperplasia tumor (FIG. 14b, diamond circles) and the high LOR-1 staining in cells of the colon adenoma (FIG. 14b, circle arrows, magnification ×4). Also note the significant LOR-1 staining in low-grade adenocarcinoma (FIG. 14c, arrows, magnification ×10) and in high-grade carcinoma (FIG. 14d, magnification ×20).

DESCRIPTION OF THE PREFERRED EMBODIMENTS

Figure 1:
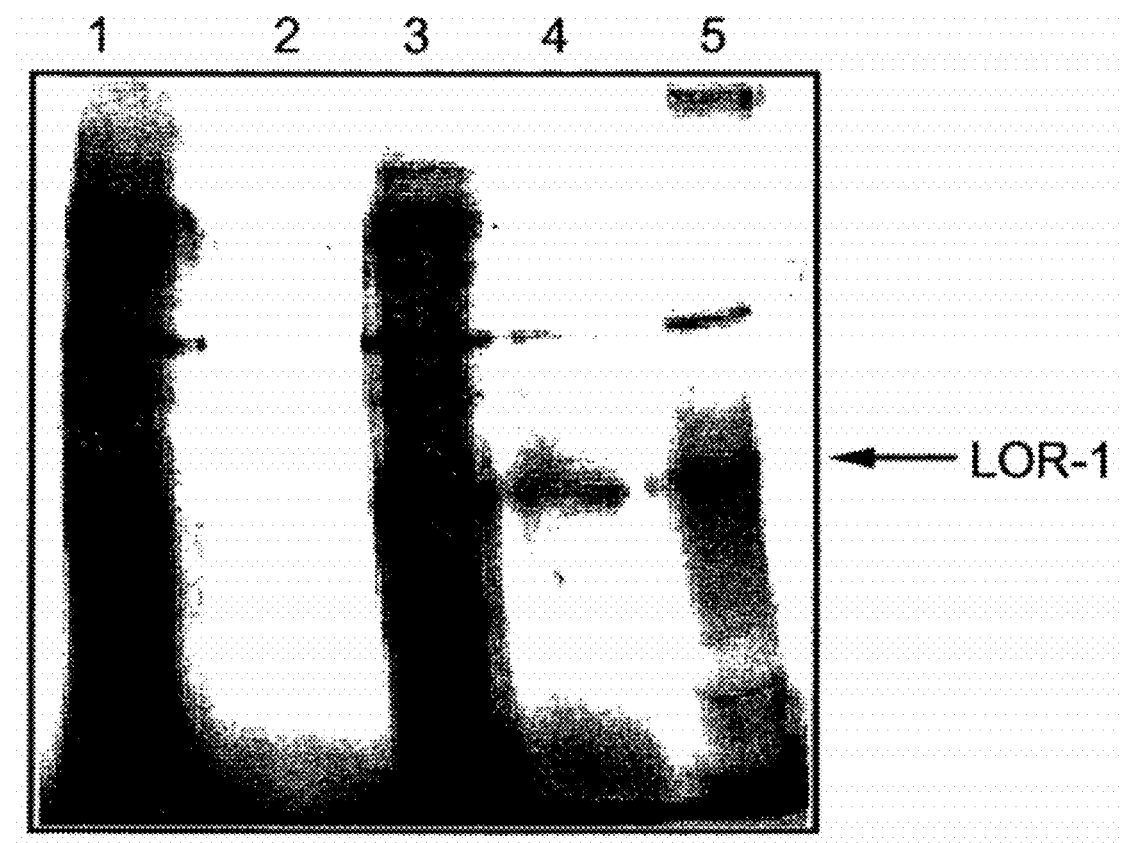
FIG. 1 illustrates SDS-PAGE analysis of extracts of Porcine aortic endothelial cells (PAE Cells) which were transfected with vector along (lane 1) or with vector containing the LOR-1 cDNA (lane 3) and metabolically labeled with $^{35}$S-methionine. Extracts from the vector transfected cells (lane 2), from vector containing LOR-1 cDNA transfected cells (lane 4) or from $^{35}$S-methionine labeled human umbilical vein endothelial cells (HUVEC) (lane 5) were purified on a PF4 affinity column. A Band corresponding in size to the original band observed in the HUVEC is evident (compare lanes 4 and 5); this band is absent in extracts of vector transfected cells.

The present invention is of pharmaceutical compositions and methods that can be used to modulate angiogenesis and to inhibit tumor invasiveness and tumor fibrosis. Specifically, the present invention can be used to suppress tumor growth and metastasis as well as to treat disorders such as, for example, arthritis, diabetic retinopathy, psoriasis and vasculitis. Moreover, the present invention is of a method of determining the malignancy of colon cancer tumors which can be used for colon cancer staging. Specifically, the present invention can be used to predict the prognosis of colon cancer patients based on the tissue level and/or activity level of LOR-1 in the colon tumors.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings described in the Examples section. The invention is capable of other embodiments or of being practiced or carried out in various ways. Also, it is to be understood that the phraseology and terminology employed herein is for the purpose of description and should not be regarded as limiting.

As described in the Examples section which follows, the present inventors have uncovered a novel protein constituent of the angiogenic process.

Figure 8:
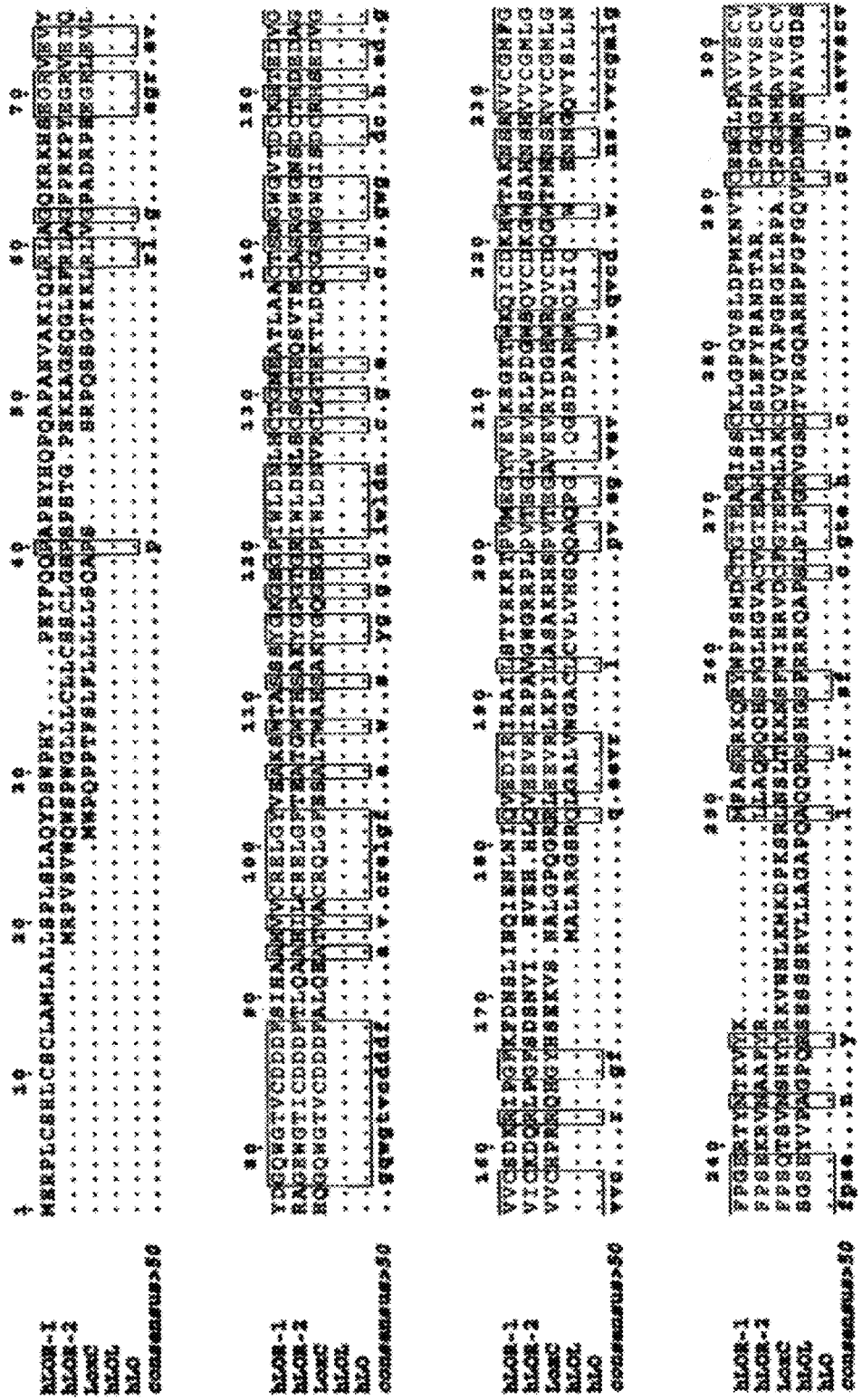
FIG. 8 illustrates sequence alignment of several lysyl oxidases including LOR-1. The polypeptide sequences shown, from top to bottom, are set forth in SEQ ID NOs:2, 9, 3, 6, and 8, respectively.
Figure 8:
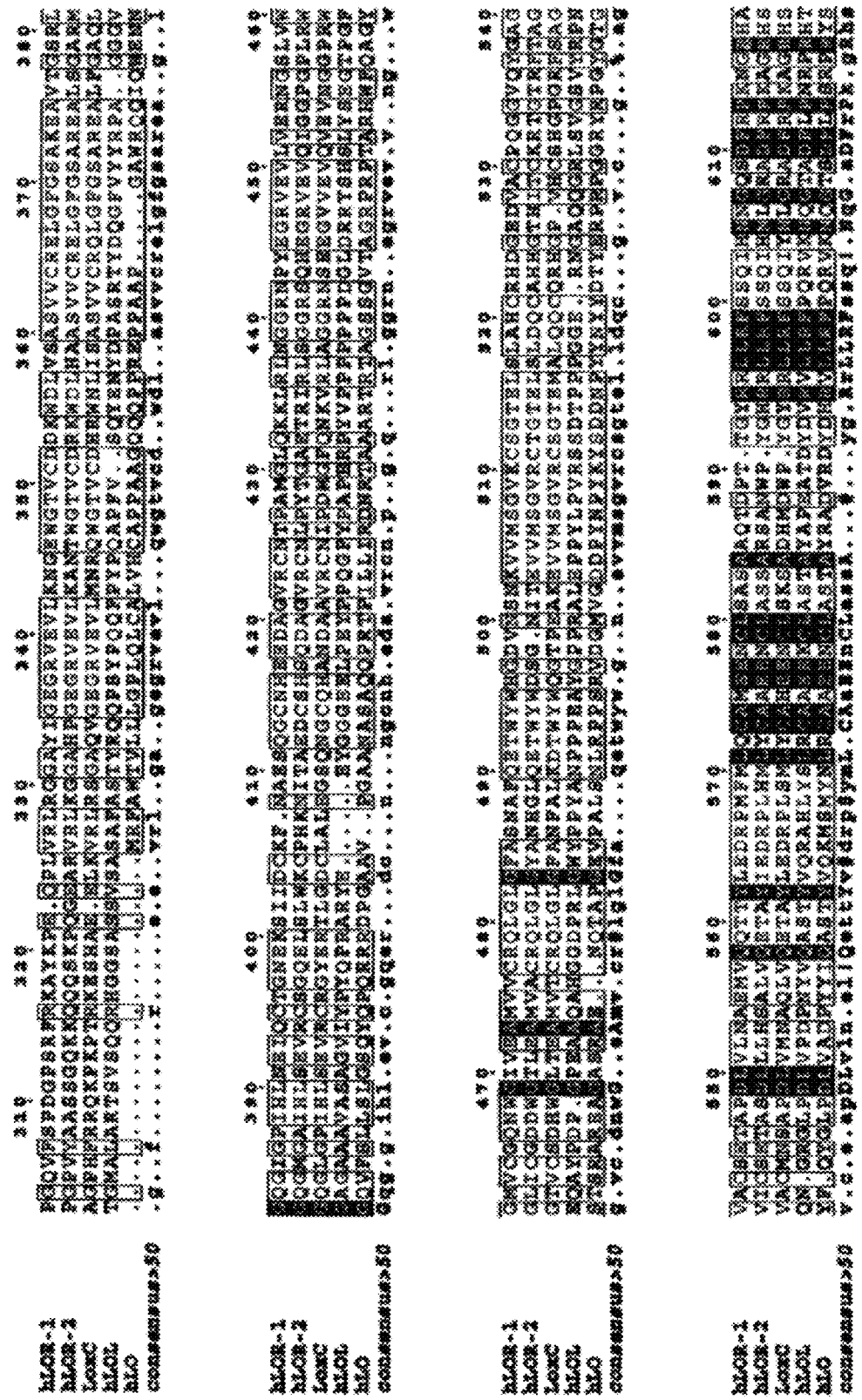
Figure 8:
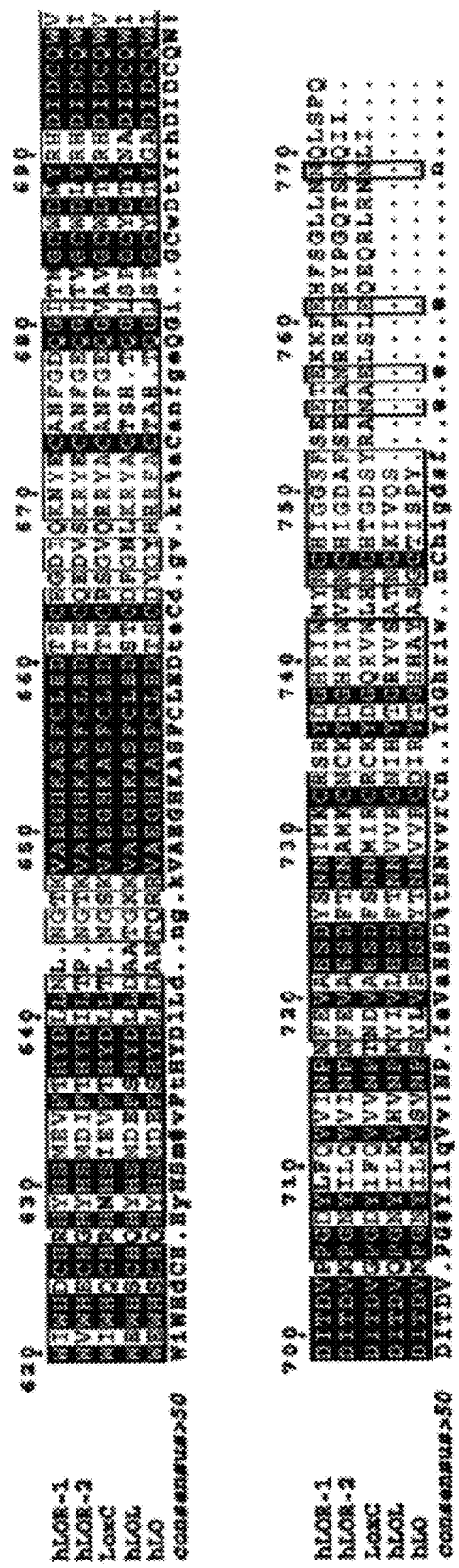

This protein, which is termed LOR-1 herein (SEQ ID NO:2) belongs to the lysyl oxidase family of enzymes which catalyze the formation of covalent crosslinks between lysine residues on adjacent collagen or elastin fibrils. The lysyl oxidase family includes four genes (Saito et al., 1997; Kim et al., 1995; Reiser et al., 1992; Jang et al., 1999), the protein sequences of which are presented in SEQ ID NOs:3, 6, 8 and 9. A homology comparison between several lysyl oxidase family members is presented in FIG. 8 which is further described in the Examples section which follows.

Each member of the lysyl oxidase family of enzymes includes a highly conserved lysyl oxidase domain, the activity of which is highly dependent on the presence of copper.

It should be noted that prior art studies have shown that removal of copper from tumor tissues leads to inhibition of angiogenesis (Rabinovitz, 1999; Yoshida et al., 1995). This further substantiates the role of the lysyl oxidase family of enzymes in angiogenesis since presumably, removal of copper leads to inhibition of lysyl oxidases.

Further support to the angiogenic activity of lysyl oxidases is provided by the PF4-LOR-1 binding assays presented herein. As mentioned hereinabove, PF4 is an inhibitor of angiogenesis. As such, the anti-angiogenic activity exhibited by PF4 may be effected through LOR-1 inhibition, which, as demonstrated in the Examples section which follows, is highly expressed in the endothelial cells lining blood vessels.

Thus according to one aspect of the present invention there is provided a method of modulating angiogenesis The method is effected by administering into the mammalian tissue a molecule capable of modifying a tissue level and/or activity of at least one type of lysyl oxidase to thereby modulate angiogenesis in the mammalian tissue.

As used herein, the phrase "tissue level" refers to the level of lysyl oxidase protein present in active form in the tissue at a given time point. Protein levels are determined by factors such as, transcription and/or translation rates, RNA or protein turnover and/or protein localization within the cell. As such any molecule which effects any of these factors can modify the tissue level of the lysyl oxidase.

As used herein the term "activity" refers to an enzymatic activity of the lysyl oxidase. A molecule which can modify the enzymatic activity may directly or indirectly alter substrate specificity of the enzyme or activity of the catalytic site thereof.

There are numerous examples of molecules which can specifically modify the tissue level and/or activity of a lysyl oxidase. Such molecules can be categorized into lysyl oxidase "downregulators" or "upregulators".

Downregulators

One example of an agent capable of downregulating a lysyl oxidase protein is an antibody or antibody fragment capable of specifically binding lysyl oxidase or at least part of the lysyl oxidase protein (e.g., region spanning the catalytic site) and inhibiting its activity when introduced into the mammalian tissue. As such, an antibody or an antibody fragment directed at a lysyl oxidase can be used to suppress or arrest the formation of blood vessels, and to inhibit tumor fibrosis and metastasis.

Numerous examples of antibody inhibitors are known in the art, including inhibitors of angiogenesis which target angiogenic factors (Brooks et al., 1994; Brooks et al., 1998).

Preferably, the antibody specifically binds to at least one epitope of a lysyl oxidase. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three-dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference). Antibody fragments according to the present invention can be prepared by proteolytic hydrolysis of the antibody or by expression in E. Coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat. Acad. Sci. USA 69: 2659-62 (1972)]. Alternatively, the variable chains can be linked by an intermolecular disulfide bond or cross-linked by chemicals such as gluteraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. Coli. The recombinant host cells synthesize a single polypeptide chain with a linker peptide bridging the two V domains. Methods for producing sFvs are described, for example, by Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321: 522-525 (1986); Riechmann et al., Nature 332: 323-327 (1988); Verhoeyen et al., Science, 239: 1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227: 381 (1991); Marks et al., J. Mol. Biol., 222: 581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1): 86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368: 812-13 (1994); Fishwild et al., Nature Biotechnology 14: 845-51 (1996); Neuberger, Nature Biotechnology 14: 826 (1996); and Lonberg and Huszar, Intern. Rev. Immunol. 13: 65-93 (1995).

As is described below, various approaches can be used to reduce or abolish transcription or translation of a lysyl oxidase. These include antisense oligonucleotides, Ribozyme, DNAzyme, siRNA and triple helix forming oligonucleotide approaches.

Antisense Polynucleotide

Downregulation of a lysyl oxidase can be effected using an antisense polynucleotide capable of specifically hybridizing with an mRNA transcript encoding the lysyl oxidase protein.

Design of antisense molecules which can be used to efficiently downregulate lysyl oxidase must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

Several considerations must be taken into account when designing antisense oligonucleotides. For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity. Algorithms for identifying those sequences with the highest predicted binding affinity for their target mRNA based on a thermodynamic cycle that accounts for the energy of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

An antisense molecule which can be used with the present invention includes a polynucleotide or a polynucleotide analog of at least 10 bases, preferably between 10 and 15, more preferably between 15 and 20 bases, most preferably at least 17, at least 18, at least 19, at least 20, at least 22, at least 25, at least 30 or at least 40 bases which is hybridizable in vivo, under physiological conditions, with a portion of a polynucleotide strand encoding a polypeptide at least 50% homologous to SEQ ID NO:1, 4, 5 or 7 or at least 75% homologous to an N-terminal portion thereof as determined using the BestFit software of the Wisconsin sequence analysis package, utilizing the Smith and Waterman algorithm, where gap creation penalty equals 8 and gap extension penalty equals 2.

The antisense oligonucleotides used by the present invention can be expressed from a nucleic acid construct administered into the tissue, in which case inducible promoters are preferably used such that antisense expression can be switched on and off, or alternatively such oligonucleotides can be chemically synthesized and administered directly into the tissue, as part of, for example, a pharmaceutical composition.

The ability of chemically synthesizing oligonucleotides and analogs thereof having a selected predetermined sequence offers means for downmodulating gene expression. Four types of gene expression modulation strategies may be considered.

At the transcription level, antisense or sense oligonucleotides or analogs that bind to the genomic DNA by strand displacement or the formation of a triple helix, may prevent transcription. At the transcript level, antisense oligonucleotides or analogs that bind target mRNA molecules lead to the enzymatic cleavage of the hybrid by intracellular RNase H. In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing. As a result, in both cases, the number of the target mRNA intact transcripts ready for translation is reduced or eliminated.

At the translation level, antisense oligonucleotides or analogs that bind target mRNA molecules prevent, by steric hindrance, binding of essential translation factors (ribosomes), to the target mRNA, a phenomenon known in the art as hybridization arrest, disabling the translation of such mRNAs.

Unmodified oligonucleotides are typically impractical for use as antisense sequences since they have short in vivo half-lives, during which they are degraded rapidly by nucleases. Furthermore, they are difficult to prepare in more than milligram quantities. In addition, such oligonucleotides are poor cell membrane penetrants.

Thus it is apparent that in order to meet all the above listed requirements, oligonucleotide analogs need to be devised in a suitable manner.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases, thereby improving binding conditions with regard to ionic strength and pH.

In addition, in order to improve half-life as well as membrane penetration, a large number of variations in polynucleotide backbones have been done, nevertheless with little success.

Oligonucleotides can be modified either in the base, the sugar or the phosphate moiety. These modifications include, for example, the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester bridges, carbonate bridges, carboxymethyl ester bridges, acetamide bridges, carbamate bridges, thioether bridges, sulfoxy bridges, sulfono bridges, various "plastic" DNAs, anomeric bridges and borane derivatives [Cook (1991) Medicinal chemistry of antisense oligonucleotides-future opportunities. Anti-Cancer Drug Design 6: 585].

International patent application WO 89/12060 discloses various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—SO2-).

International patent application WO 92/20702 describe an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other. PNA oligomers can be synthesized from the four protected monomers containing thymine, cytosine, adenine and guanine by Merrifield solid-phase peptide synthesis. In order to increase solubility in water and to prevent aggregation, a lysine amide group is placed at the C-terminal region.

RNA oligonucleotides may also be used for antisense inhibition as they form a stable RNA-RNA duplex with the target, suggesting efficient inhibition. However, due to their low stability RNA oligonucleotides are typically expressed inside the cells using vectors designed for this purpose. This approach is favored when attempting to target an mRNA that encodes an abundant and long-lived protein.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

Antisense therapeutics has the potential to treat many life-threatening diseases with a number of advantages over traditional drugs. Traditional drugs intervene after a disease-causing protein is formed. Antisense therapeutics, however, block mRNA transcription/translation and intervene before a protein is formed, and since antisense therapeutics target only one specific mRNA, they should be more effective with fewer side effects than current protein-inhibiting therapy.

Several clinical trials have demonstrated safety, feasibility and activity of antisense oligonucleotides. For example, antisense oligonucleotides suitable for the treatment of cancer have been successfully used [Holmund et al., Curr Opin Mol Ther 1: 372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1: 297-306 (1999)].

More recently, antisense-mediated suppression of human heparanase gene expression has been reported to inhibit pleural dissemination of human cancer cells in a mouse model [Uno et al., Cancer Res 61: 7855-60 (2001)].

The first antisense drug was recently approved by the FDA. The drug, Fomivirsen, was developed by Isis, and is indicated for local treatment of cytomegalovirus in patients with AIDS who are intolerant of or have a contraindication to other treatments for CMV retinitis or who were insufficiently responsive to previous treatments for CMV retinitis (Pharmacotherapy News Network).

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Ribozyme

Another agent capable of downregulating a lysyl oxidase is a ribozyme molecule capable of specifically cleaving an mRNA transcript encoding a lysyl oxidase. Ribozymes are being increasingly used for the sequence-specific inhibition of gene expression by the cleavage of mRNAs encoding proteins of interest [Welch et al., Curr Opin Biotechnol. 9: 486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10: 163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

DNAzyme

Another agent capable of downregulating a lysyl oxidase is a DNAzyme molecule capable of specifically cleaving an mRNA transcript or DNA sequence of the lysyl oxidase. DNAzymes are single-stranded polynucleotides which are capable of cleaving both single and double stranded target sequences (Breaker, R. R. and Joyce, G. Chemistry and Biology 1995; 2: 655; Santoro, S. W. & Joyce, G. F. Proc. Natl, Acad. Sci. USA 1997; 943: 4262). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine: pyrimidine junctions (Santoro, S. W. & Joyce, G. F. Proc. Natl, Acad. Sci. USA 1997; 943: 4262; for rev of DNAzymes see Khachigian, L M [Curr Opin Mol Ther 4: 119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 2002, Abstract 409, Ann Meeting Am. Soc. Gen. Ther., located on the World Wide Web at asgt.org). In another application, DNAzymes complementary to bcr-abl oncogenes were successful in inhibiting the oncogenes expression in leukemia cells, and lessening relapse rates in autologous bone marrow transplant in cases of CML and ALL.

siRNA

Another mechanism of down regulating a lysyl oxidase at the transcript level is RNA interference (RNAi), an approach which utilizes small interfering dsRNA (siRNA) molecules that are homologous to the target mRNA and lead to its degradation [Carthew RW. Gene silencing by double-stranded RNA. Curr Opin Cell Biol 2001 April; 13(2):244-8].

RNA interference is a two-step process. In the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 by duplexes (siRNA), each with 2-nucleotide 3' overhangs [Hutvagner and Zamore Curr. Opin. Genetics and Development 12: 225-232 (2002); and Bernstein Nature 409: 363-366 (2001)].

In the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12: 225-232 (2002); Hammond et al. (2001) Nat. Rev. Gen. 2: 110-119 (2001); and Sharp Genes. Dev. 15: 485-90 (2001)]. Although the mechanism of cleavage is still to be elucidated, research indicates that each RISC contains a single siRNA and an RNase [Hutvagner and Zamore Curr. Opin. Genetics and Development 12: 225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2: 110-119 (2001), Sharp Genes. Dev. 15: 485-90 (2001); Hutvagner and Zamore Curr. Opin. Genetics and Development 12: 225-232 (2002)]. For more information on RNAi see the following reviews Tuschl Chem Biochem. 2: 239-245 (2001); Cullen Nat. Immunol. 3: 597-599 (2002); and Brantl Biochem. Biophys. Act. 1575: 15-25 (2002).

Synthesis of RNAi molecules suitable for use with the present invention can be effected as follows. First, the lysyl oxidase mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl Chem Biochem. 2: 239-245, 2001]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (located on the World Wide Web at ambion.com/techlib/tn/91/912.html).

Second, potential target sites are compared to an appropriate genomic database (e.g., human, mouse, rat etc.) using any sequence alignment software, such as the BLAST software available from the NCBI server (located on the World Wide Web at ncbi.nlm.nih gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

The siRNA molecules of the present invention are preferably transcribed from expression vectors which can facilitate stable expression of the siRNA transcripts once introduced into a host cell. These vectors are engineered to express small hairpin RNAs (shRNAs), which are processed in vivo into siRNA molecules capable of carrying out gene-specific silencing [Brummelkamp, T. R., et al., (2002) A system for stable expression of short interfering RNAs in mammalian cells. Science 296: 550-53; Paddison, P. J., et al. (2002) Short hairpin RNAs (shRNAs) induce sequence-specific silencing in mammalian cells. Genes Dev. 16:948-58; Paul et al. (2002) Nature Biotech. 20: 505-08; Yu, J. Y., et al. (2002) RNA interference by expression of short-interfering RNAs and hairpin RNAs in mammalian cells. Proc. Natl. Acad. Sci. USA 99: 6047-52]

An example of a suitable expression vector is the pSUPER™, which includes the polymerase-III H1-RNA gene promoter with a well defined start of transcription and a termination signal consisting of five thymidines in a row (T5) [Brummelkamp, T. R. et al. (2002), Science 296: 550-53]. Most importantly, the cleavage of the transcript at the termination site is at a site following the second uridine, thus yielding a transcript which resembles the ends of synthetic siRNAs, which also contain nucleotide overhangs. siRNA is cloned such that it includes the sequence of interest, i.e., lysyl oxidase separated by a short spacer from the reverse complement of the same sequence. The resulting transcript folds back on itself to form a stem-loop structure, which mediates lysyl oxidase RNAi.

Another suitable siRNA expression vector encodes the sense and antisense siRNA under the regulation of separate polIII promoters [Miyagishi and Taira (2002) Nature Biotech. 20: 497-500]. The siRNA, generated by this vector also includes a five thymidine (T5) termination signal.

Since approaches for introducing synthetic siRNA into cells by lipofection can result in low transfection efficiencies in some cell types and/or short-term persistence of silencing effects, vector mediated methods have been developed.

Thus, siRNA molecules utilized by the present invention are preferably delivered into cell using retroviruses. Delivery of siRNA using retroviruses provides several advantages over methods, such as lipofection, since retroviral delivery is more efficient, uniform and immediately selects for stable "knockdown" cells [Devroe, E. and Silver, P. A. (2002). Retrovirus-delivered siRNA. BMC Biotechnol. 2: 15]

Recent scientific publications have validated the efficacy of such short double stranded RNA molecules in inhibiting target mRNA expression and thus have clearly demonstrated the therapeutic potential of such molecules. For example, RNAi has been utilized to inhibit expression of hepatitis C (McCaffrey, A. P., et al., 2002, Gene expression: RNA interference in adult mice. Nature 418, 38-39), HIV-1 (Jacque, J-M., et al. 2002, Modulation of HIV-1 replication by RNA interference. Nature 418, 435-438), cervical cancer cells (Jiang, M., and Milner, J. 2002, Selective silencing of viral gene expression in HPV-positive human cervical carcinoma cells treated with siRNA, a primer of RNA interference. Oncogene 21, 6041-8) and leukemic cells [Wilda, M., et al., 2002, Killing of leukemic cells with a BCR/ABL fusion gene by RNA interference (RNAi). Oncogene 21, 5716-24].

Triple Helix Forming Oligonucleotide (TFO)

An additional method of regulating the expression of a lysyl oxidase in cells is via triplex forming oligonucleotides (TFOs). Recent studies have shown that TFOs can be designed which can recognize and bind to polypurine/polypyrimidine regions in double-stranded helical DNA in a sequence-specific manner. These recognition rules are outlined by Maher III, L. J., et al., Science (1989), 245: 725-730; Moser, H. E., et al., Science (1987), 238: 645-630; Beal, P. A., et al, Science (1992), 251: 1360-1363; Cooney, M., et al., Science (1988), 241: 456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences [for a recent review see Seidman and Glazer, J. Clin. Invest. (2003), 112: 487-94].

In general, the triplex-forming oligonucleotide has the sequence correspondence:

```
oligo       3'--A G G T
duplex      5'--A G C T
duplex      3'--T C G A
```

However, it has been shown that the A-AT and G-GC triplets have the greatest triple helical stability (Reither and Jeltsch, BMC Biochem, 2002, September 12, Epub). The same authors have demonstrated that TFOs designed according to the A-AT and G-GC rule do not form non-specific triplexes, indicating that the triplex formation is indeed sequence specific.

Thus for any given sequence in the lysyl oxidase regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27: 1176-81, and Puri, et al, J Biol Chem, 2001; 276: 28991-98), and the sequence- and target specific downregulation of expression of the Ets2 transcription factor, important in prostate cancer etiology (Carbone, et al, Nucl Acid Res. 2003; 31: 833-43), and the pro-inflammatory ICAM-1 gene (Besch et al, J Biol Chem, 2002; 277: 32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28: 2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112: 487-94). Detailed description of the design, synthesis and administration of effective TFOs can be found in U.S. Pat. Appl. Nos. 2003 017068 and 2003 0096980 to Froehler et al, and 2002 0128218 and 2002 0123476 to Emanuele et al, and U.S. Pat. No. 5,721,138 to Lawn.

The downregulators described hereinabove would be particularly useful for inhibiting angiogenesis in tumor tissue. It has been shown that PF4, a lysyl oxidase binding protein which inhibits angiogenesis in tumor tissue specifically accumulates in newly formed blood vessels of tumors (angiogenic vessels) but not in established blood vessels (Hansell, P., et al., 1995, Selective binding of platelet factor 4 to regions of active angiogenesis in vivo. Amer. J. Physiol-Heart. Circ. Phy. 38, H829-H836; Reiser, K., et al., 1992, Enzymatic and nonenzymatic cross-linking of collagen and elastin. FASEB J. 6, 2439-2449).

Newly formed angiogenic blood vessels are more permeable to proteins than established blood vessels because the major inducer of angiogenesis in many angiogenic diseases is VEGF, a growth factor which also functions as a potent blood vessel permeabilizing factor (VPF) [Neufeld et al., 1999, Vascular endothelial growth factor (VEGF) and its receptors. FASEB J. 13(1): 9-22]. Tumor associated blood vessels are therefore in a permanent state of hyperpermeability due to deregulated over-expression of VEGF (Shweiki et al., 1995; Rak et al., 1995) and as such, a downregulator molecule used by the method of the present invention would be able to extravasate efficiently from tumor blood vessels but much less efficiently from normal stabilized blood vessels.

Upregulators

Several approaches can be utilized to increase the levels of lysyl oxidase and as such to enhance the formation of blood vessels.

For example, a nucleic acid construct including a constitutive, inducible or tissue specific promoter positioned upstream of a polynucleotide encoding a polypeptide having lysyl oxidase activity, such as the polypeptide set forth in SEQ ID NO:2, 3, 6, 8 or 9 can be administered into a mammalian tissue. The lysyl oxidase expressed from this construct would substantially increase the levels of lysyl oxidase within the cells of the tissue and as such enhance angiogenesis.

The polynucleotide segments encoding the lysyl oxidase can be ligated into a commercially available expression vector. Such an expression vector includes a promoter sequence for directing transcription of the polynucleotide sequence in the cell in a constitutive or inducible manner. A suitable promoter can be, for example, a Tie-2 promoter which is capable of directing lysyl oxidase specific gene expression in endothelial cells (see Schlaeger, T. M., Bartunkova, S., Lawitts, J. A., Teichmann, G., Risau, W., Deutsch, U., and Sato, T. N. (1997). Uniform vascular-endothelial-cell-specific gene expression in both embryonic and adult transgenic mice. Proc. Natl. Acad. Sci. U.S.A 94, 3058-3063). The expression vector of the present invention can further include additional polynucleotide sequences such as for example, sequences encoding selection markers or reporter polypeptides, sequences encoding origin of replication in bacteria, sequences that allow for translation of several proteins from a single mRNA such as an internal ribosome entry site (IRES), sequences for genomic integration of the promoter-chimeric polypeptide encoding region and/or sequences generally included in mammalian expression vector such as pcDNA3, pcDNA3.1(+/−), pZeoSV2(+/−), pSecTag2, pDisplay, pEF/ myc/cyto, pCMV/myc/cyto, pCR3.1, which are available from Invitrogen, pCI which is available from Promega, pBK-RSV and pBK-CMV which are available from Strategene, pTRES which is available from Clontech, and their derivatives.

It will be appreciated that such commercially available vector systems can easily be modified via commonly used recombinant techniques in order to replace, duplicate or mutate existing promoter or enhancer sequences and/or introduce any additional polynucleotide sequences.

An agent capable of upregulating a lysyl oxidase may also be any compound which is capable of increasing the transcription and/or translation of an endogenous DNA or mRNA encoding a lysyl oxidase using for example gene "knock in" techniques.

Enhancer elements can be "knocked-in" adjacent to endogenous lysyl oxidase coding sequences to thereby increase transcription therefrom.

Further details relating to the construction and use of knock-out and knock-in constructs is provided elsewhere [Fukushige S. and Ikeda, J. E. Trapping of mammalian promoters by Cre-lox site-specific recombination. DNA Res 3 (1996) 73-80; Bedell, M. A., et al. Mouse models of human disease. Part I: Techniques and resources for genetic analysis in mice. Genes and Development 11 (1997) 1-11; Bermingham, J. J., et al. Tst-1/Oct-6/SCIP regulates a unique step in peripheral myelination and is required for normal respiration. Genes Dev 10 (1996) 1751-62].

It will be appreciated that direct administration of a polypeptide exhibiting a lysyl oxidase activity can also be utilized for enhancing angiogenesis.

Thus, affinity binding assays and/or activity assays, the principles of which are well known in the art, can be used to screen for novel compounds (e.g., substrate analogs) which can specifically regulate the activity of a lysyl oxidase and as such can be used with the present invention.

An assay suitable for use with this aspect of the present invention has been previously described in a study conducted by Bedell-Hogan et al., 1993.

As is clearly illustrated in the Examples section which follows, the present study also correlated expression levels of LOR-1 to the metastatic properties of breast cancer derived cell lines, indicating that LOR-1 may play additional roles in tumor invasiveness in addition to its role in angiogenesis.

Thus, the present invention also provides a method of inhibiting metastasis and/or fibrosis in a mammalian tissue. The method is effected by administering to the mammalian tissue a molecule capable of downregulating a tissue level and/or an activity of at least one type of a lysyl oxidase.

The method of the present invention can be used to treat human patients that have been diagnosed with cancerous tumors, by administering any of the downregulating molecules described herein above, in order to reduce the tissue level and/or activity of at least one type of a lysyl oxidase.

As used herein, the phrase "cancerous tumor" refers to any malignant tumor within a human body including, but not limiting to, tumors with metastases. In addition, and without being bound to any particular type of cancerous tumor, the present invention is useful to treat breast cancer tumors, with or without metastases.

As used herein, the phrase "administering" refers to all modes of administration described hereinbelow with respect to the pharmaceutical compositions of the present invention.

These include, but not limit to, local administration at the tumor tissue, an organ where the cancerous tumor was diagnosed and/or related tissues that typically form metastases [Hortobagyi, 2002, Semin Oncol 29 (3 Suppl 11): 134-44; Morrow and Gradishar, 2002, 324: 410-4]. Examples of related tissue include lymph nodes adjacent to, for example, breast tissue and bones.

Administration can also be effected in a systemic manner in order to treat the affected tissue, i.e., the tissue where the cancerous tumor was formed and where metastases are present or likely to be formed with tumor progression.

Since any molecule capable of downregulating a lysyl oxidase activity can be utilized by the methods described hereinabove, the present invention also provides a method of identifying molecules capable of inhibiting metastasis and/or fibrosis.

This method is effected by screening and identifying molecules which exhibit specific reactivity with at least one type of lysyl oxidase and testing a metastasis and/or fibrosis inhibitory potential of these molecules.

Numerous types of molecules can be screened for reactivity with at least one type of lysyl oxidase, examples include, but are not limited to, molecules such as antisense oligonucleotides, siRNA, DNAzymes, ribozymes and triple helix forming oligonucleotides (TFOs) that interact with a polynucleotide expressing a lysyl oxidase activity or molecules such as antibodies that interact with polypeptides having a lysyl oxidase activity. In addition, short peptides and other small molecules can also be screened by this method of the present invention.

Screening for cross reactivity can be effected by lysyl oxidase enzymatic activity assays, by binding assays and the like. Examples of suitable assays are provided in Rodriguez et al., 2002, Arterioscler Thromb Vasc Biol 22: 1409-14; Wilson and Nock, 2002, Curr Opin Chem Biol 6: 81-5; Uetz, 2002, Curr Opin Chem Biol 6: 57-62; Stoll et al., 2002, Front Biosci 2002 7: c13-32).

Testing a metastatic phenotype of transformed tumor cells can be performed in vitro since nearly all steps of the metastatic process, including attachment, matrix degradation and migration, can be modeled experimentally in vitro by measuring invasion of a reconstituted basement membrane (RBM). Metastatic invasiveness of tumor cell can be modeled by migration of tumor cells into reconstituted basement membrane (RBM) in the presence and absence of a chemoattractant, such as fibroblast conditioned medium (FCM). The assay determines cells that have attached to the RBM, degraded the RBM enzymatically and, finally, cells that have penetrated the FCM side of the membrane.

Since in vitro metastasis events correspond to steps observed in the metastatic spread of tumor cells through the basement membrane in vivo, in vitro invasiveness of cells can be assayed by the methods described in Albini et al., 1987 Cancer Research 47: 3239-3245, which is incorporated herein by reference in its entirety. Invasiveness assays and other methods for assessing metastatic affects, are described in Leyton et al., 1994 Cancer Research 54: 3696-3699, which is incorporated by reference herein in its entirety. Reconstituted basement membrane preparations for use in accordance with the hereinabove described assays are readily available from numerous commercial suppliers. One suitable example membrane in this regard is "MATRIGEL" available from Collaborative Biomedical Products of Bedford, Mass.

In vitro evaluation of tumor cell metastatic phenotype can also be effected by determining level and pattern of expression of one or more metastasis associated markers such protease markers, which are considered to be an integral part of tumor metastasis (see U.S. Pat. No. 6,303,318). One example is the arachidonic acid, the release of which in cells can serve to indicate metastatic potential of a tumor (U.S. Pat. No. 6,316,416). In this regard, determining phospholipase A-2 ($PLA_2$) activity, and the activity or abundance of factors that affect the activity of $PLA_2$, such as uteroglobin protein (U.S. Pat. No. 6,316,416) can serve as an indication of metastatic potential.

Determining pattern and level of expression of metastasis-associated markers can be effected by one of several methods known in the art.

The presence or level of proteins indicative of metastatic potential of tumors can be determined in cells by conventional methods well known to those of skill in the art. For instance, the techniques for making and using antibody and other immunological reagents and for detecting particular proteins in samples using such reagents are described in current protocols in immunology, Coligan et al., Eds., John Wiley & Sons, New York (1995), which is incorporated by reference herein in parts pertinent to making and using reagents useful for determining specific proteins in samples. As another example, immunohistochemical methods for determining proteins in cells in tissues are described in Volume 2, Chapter 14 of current protocols in molecular biology, Ausubel et al., Eds., John Wiley & Sons, Inc. (1994), which is incorporated by reference herein in part pertinent to carrying out such determinations. Finally, Linnoila et al., A. J. C. P. 97(2): 235-243 (1992) and Peri et al., J. Clin. Invest. 92: 2099-2109 (1992), incorporated herein as referred to above, describe techniques that may need, in part, in this aspect of the present invention.

Metastatic potential can also be determined in vivo at the mRNA level. The presence and/or level of mRNA transcripts can be determined by a variety of methods known to those of skill in the art. A given mRNA may be detected in cells by hybridization to a specific probe. Such probes may be cloned DNAs or fragments thereof, RNA, typically made by in vitro transcription, or oligonucleotide probes, usually generated by solid phase synthesis. Methods for generating and using probes suitable for specific hybridization are well known and used in the art.

A variety of controls may be usefully employed to improve accuracy in mRNA detection assays. For instance, samples may be hybridized to an irrelevant probe and treated with RNAse A prior to hybridization, to assess false hybridization.

In order to modulate angiogenesis or inhibit metastasis or tumor fibrosis, the molecules used by the present invention can be administered to the individual per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration/targeting of a compound to a mammal.

As used herein the term "active ingredients", refers to the preparation accountable for the biological effect, i.e. the upregulator/downregulator molecules used by the present invention to modulate angiogenesis and the downregulators molecules used by the present invention to inhibit metastasis and tumor fibrosis.

Hereinafter, the phrases "physiologically acceptable carrier" and "pharmaceutically acceptable carrier" are interchangeably used to refer to a carrier, such as, for example, a liposome, a virus, a micelle, or a protein, or a diluent which do not cause significant irritation to the mammal and do not abrogate the biological activity and properties of the active ingredient. An adjuvant is included under these phrases.

Herein the term "excipient" refers to an inert substance added to a pharmaceutical composition to further facilitate administration of an active ingredient. Examples, without limitation, of excipients, include calcium carbonate, calcium phosphate, various sugars and types of starch, cellulose derivatives, gelatin, vegetable oils and polyethylene glycols.

Techniques for formulation and administration of compositions may be found in "Remington's Pharmaceutical Sciences" Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, inrtaperitoneal, intranasal, or intraocular injections.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active ingredient with pharmaceutically acceptable carriers well known in the art. Such carriers enable the active ingredient of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose.

The pharmaceutical composition may form a part of an article of manufacturing which also includes a packaging material for containing the pharmaceutical composition and a leaflet which provides indications of use for the pharmaceutical composition.

Thus, the present invention provides a method and pharmaceutical compositions useful modulating angiogenesis.

Such modulation activity can be used to treat arthritis (Koch, 1998; Paleolog and Fava, 1998), diabetic retinopathy (Miller et al., 1997), psoriasis (Detmar et al., 1994; Creamer et al., 1997) and vasculitis (Lie, 1992; Klipple and Riordan, 1989).

In addition, the present invention can also be used to treat disease characterized by fragile blood vessels, including Marfans syndrome, Kawasaki, Ehlers-Danlos, cutis-laxa, and takysu (Lie, 1992; Klipple and Riordan, 1989; Brahn et al., 1999; Cid et al., 1993; Hoffman et al., 1991).

It is possible that some of these diseases result from reduced or abolished lysyl oxidase activity which leads to the synthesis of a fragile extracellular matrix, and consequently, fragile blood vessels.

As such, administration of lysyl oxidase encoding sequences or polypeptides can be used to correct some of the manifestations of these diseases.

The present invention can also be used to treat diseases which are characterized by changes in the wall of blood vessels. For example, restenosis which is a common complication following balloon therapy, Fibromuscular dysplasia (Begelman and Olin, 2000) and aortic stenosis (Palta et al., 2000) are all potentially treatable by the method of the present invention.

Figure 3:
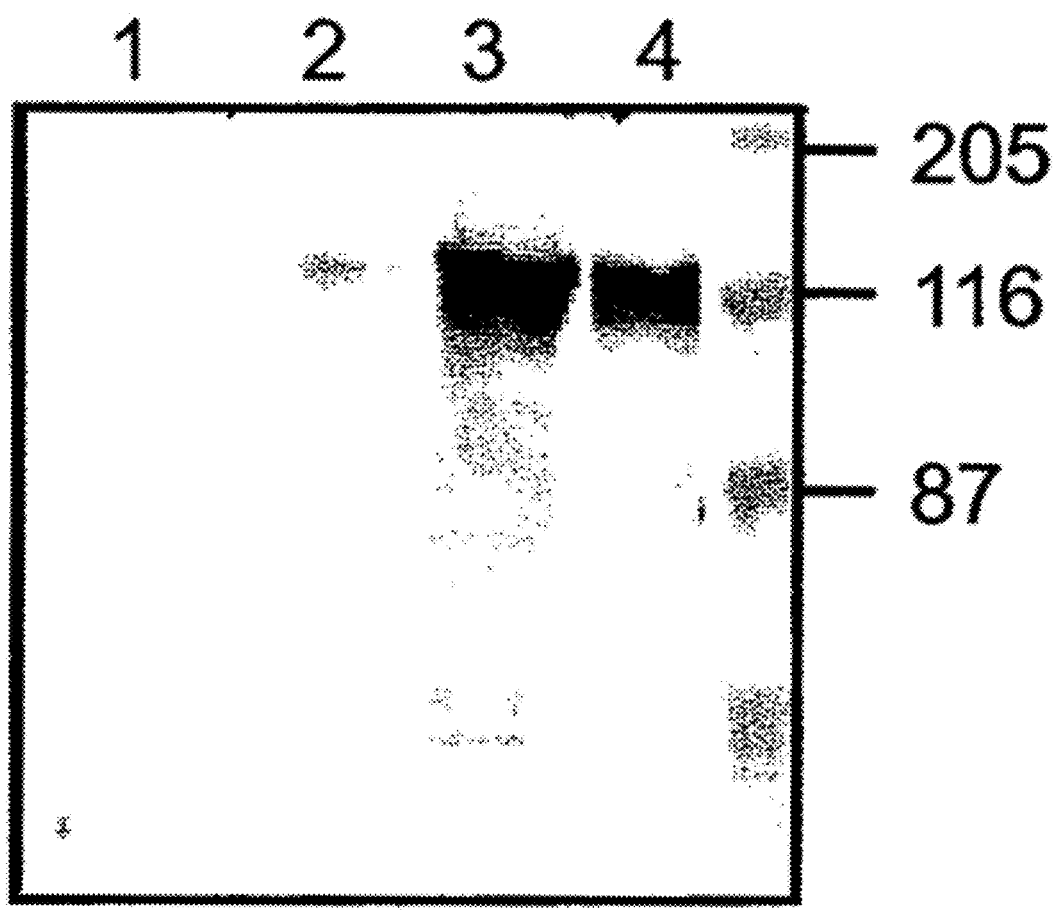
FIG. 3 illustrates expression of recombinant LOR-1 in MCF-7 breast cancer cells (lane 1). Vector transfected MCF-7 cells (lane 2) and two clones of MCF-7 expressing recombinant LOR-1 (lane 3, clone 12, lane 4, clone 22) were grown for two days in serum free medium. The medium from an equal number of cells was collected, concentrated 30 fold using Centricon™, and 10 µl aliquots were electrophoresed using an SDS/PAGE gel. Proteins were blotted onto nitrocellulose, and LOR-1 protein was identified using an antibody directed against the C-terminal of LOR-1. A secondary alkaline-phosphatase coupled antibody and NBT-BICP staining were used to detect the primary bound antibody.

In addition, as is illustrated in the Examples section which follows, LOR-1 is more highly expressed in metastatic tumors and cell lines than in non-metastatic tumors and cell lines (FIGS. 3, 9, and 13). This suggests that levels of LOR-1 expression can be used as a diagnostic tool to determine the malignancy of cancer cells, as well as, to determine and implement suitable treatment regimens.

Colon cancer is a highly treatable and often a curable disease when localized to the bowel. However, in many cases, due to mis-diagnosis, a pre-malignant colon hyperplasia progress into colon adenoma which further develop into more malignant forms of low-grade and high-grade colon adenocarcinoma. Once an individual is diagnosed with colon cancer the malignancy of the tumor needs to be assessed in order to select for suitable treatment regimens. The current practice for assessing the malignancy of a colon tumor is based on the tumor-node-metastases (TNM) staging system developed by the American Joint Committee on Cancer (AJCC). According to this method staging is based on scoring for the presence or absence of cancerous cells in the tumor itself, in the submucosa of the bowel wall, in the muscular layer of the bowel wall (muscularis propria), and/or in the subserosa, pericolic or perirectal tissues, as well as in regional lymph nodes and distance metastases. Thus, staging of colon tumors involves multiple tissue biopsies and complex pathological evaluations which are time consuming and can result in misdiagnosis.

While reducing the present invention to practice, the present inventors have also uncovered that LOR-1 expression in epithelial and/or connective tissue cells in a colon tissue is indicative of a malignant colon cancer thus providing a new method of assessing a malignancy of colon cancer tumors devoid of the above limitations.

As described in Example 3 of the Examples section which follows, the expression of LOR-1 is correlated with the formation of benign colon tumors (FIG. 14b) and is increased in more malignant forms of colon cancer tumors (FIGS. 14c and 14d) thus suggesting the use of LOR-1 in determining the stage of colon cancer tumors.

Thus according to another aspect of the present invention there is provided a method of assessing a malignancy of a colon tumor. The method is effected by determining a tissue level and/or an activity level of a polypeptide at least 75% homologous to the polypeptide set forth in SEQ ID NO:2 or 9 in the colon tumor tissue, thereby assessing the malignancy of the colon tumor.

As is used herein, the phrase "assessing a malignancy of a colon tumor" refers to determining the stage of the colon tumor, i.e., the progress of the colon tumor from a benign colon tumor to a highly malignant colon cancer which invades the surrounding tissue.

The polypeptide detected by the present invention is at least 75%, at least 80%, at least 85%, at least 90%, at least 95% homologous to SEQ ID NO:2 or 9, as determined using the BestFit software of the Wisconsin sequence analysis package, utilizing the Smith and Waterman algorithm, where gap creation penalty equals 8 and gap extension penalty equals 2.

Preferably, the polypeptide of the present invention is LOR-1 (SEQ ID NO:2), a member of the lysyl oxidase family which are fully described herein above.

According to the method of the present invention, a colon tumor tissue is obtained using a colon biopsy and/or a colon surgery using methods know in the art. Once obtained, the tissue level and/or activity level of the polypeptide of the present invention is determined in the colon tumor tissue.

Determination of the tissue level of the polypeptide of the present invention may be accomplished directly using immunological methods.

The immunological detection methods used in context of the present invention are fully explained in, for example, "Using Antibodies: A Laboratory Manual" (Ed Harlow, David Lane eds., Cold Spring Harbor Laboratory Press (1999)) and those familiar with the art will be capable of implementing the various techniques summarized hereinbelow as part of the present invention. All of the immunological techniques require antibodies specific to at least one epitope of the polypeptide of the present invention Immunological detection methods suited for use as part of the present invention include, but are not limited to, radio-immunoassay (RIA), enzyme linked immunosorbent assay (ELISA), western blot, immunohistochemical analysis.

Radio-immunoassay (RIA): In one version, this method involves precipitation of the desired substrate, e.g., LOR-1, with a specific antibody and radiolabelled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme linked immunosorbent assay (ELISA): This method involves fixation of a sample (e.g., fixed cells or a proteinaceous solution) containing a protein substrate (e.g., LOR-1) to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot analysis: This method involves separation of a substrate (e.g., LOR-1 protein) from other proteins by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabelled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Immunohistochemical Analysis:

This method involves detection of a substrate in situ in fixed tissue by substrate specific antibodies. The substrate specific antibodies may be enzyme linked or linked to fluorophores. Detection is by microscopy and subjective evaluation. If enzyme linked antibodies are employed, a colorimetric reaction may be required.

Since tissue levels of a polypeptide can be inferred from the levels of mRNA encoding such a polypeptide, the method according to this aspect of the present invention can also employ various polynucleotide detection approaches for determining the tissue level of the polypeptide of the present invention.

RNA molecules can be detected using methods known in the art including for example, Northern blot analysis, RT-PCR analyses, RNA in situ hybridization stain and in situ RT-PCR stain.

Northern Blot Analysis:

This method involves the detection of a particular RNA (e.g., the RNA molecule encoding LOR-1) in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence as described hereinabove. This method allows both quantitation of an amount of particular RNA molecules and determination of its identity by a relative position on the membrane which is indicative of a migration distance in the gel during electrophoresis.

RT-PCR Analysis:

This method uses PCR amplification of relatively rare RNAs molecules. First, RNA molecules from a particular tissue (e.g., a colon tumor tissue) are purified and converted into complementary DNA (cDNA) using a reverse transcriptase enzyme (such as an MMLV-RT) and primers such as, oligo dT, random hexamers or gene specific primers, all of which are available from Invitrogen Life Technologies, Frederick, Md., USA. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules.

RNA In Situ Hybridization Stain:

In this method DNA or RNA probes are attached to the RNA molecules present in the tissue. Generally, a tissue sample (e.g., a colon tissue) is fixed to preserve its structure and to prevent the RNA from being degraded and then sectioned for microscopy and placed on a slide. Alternatively, frozen tissue samples can be first sectioned and put on a slide and then subject to fixation prior to hybridization. Hybridization conditions include reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a colorimetric reaction which reveals signals generated using enzyme-linked labeled probes as described hereinabove.

In Situ RT-PCR Stain:

This method is described in Nuovo G J, et al. (Intracellular localization of polymerase chain reaction (PCR)-amplified hepatitis C cDNA. Am J Surg Pathol. 1993, 17: 683-90) and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed tissue sections by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Determination of an activity level of the polypeptide of the present invention (e.g., LOR-1) in a colon tumor tissue may be effected using suitable substrates in a cytochemical stain and/or in vitro activity assays.

Cytochemical Stain:

According to this method, a chromogenic substrate is applied on the colon tumor tissue containing an active enzyme (e.g., LOR-1). The enzyme catalyzes a reaction in which the substrate is decomposed to produce a chromogenic product visible by a light or a fluorescent microscope.

In Vitro Activity Assays:

In these methods the activity of a particular enzyme is measured in a protein mixture extracted from the tissue of interest (e.g., a colon tumor tissue). The activity can be measured in a spectrophotometer well using colorimetric methods (see for example, Wande Li, et al. Localization and activity of lysyl oxidase within nuclei of fibrogenic cells. Proc. Natl. Acad. Sci. USA. 1997, 94: 12817-12822) or can be measured in a non-denaturing acrylamide gel (i.e., activity gel). Following electrophoresis the gel is soaked in a solution containing a substrate and colorimetric reagents. The resulting stained band corresponds to the enzymatic activity of the polypeptide of interest (e.g., LOR-1). If well calibrated and within the linear range of response, the amount of enzyme present in the sample is proportional to the amount of color produced. An enzyme standard is generally employed to improve quantitative accuracy.

Once the tissue level and/or the activity level of the polypeptide (or mRNA) of the present invention (e.g., LOR-1) is determined in the colon tumor tissue the malignancy of the tumor is assessed by comparing the expression level and/or activity in the colon tumor tissue to that of a normal colon tissue.

It will be appreciated that the normal colon tissue may be obtained from a biopsy and/or a surgery of a colon tissue obtained form a healthy individual. Alternatively, the normal colon tissue can be obtained from an unaffected segment of the colon of the same individual. Methods of determining the status of a normal colon tissue are known to skilled in the art and include for example, a morphological evaluation of tissue sections.

Once malignancy of colon cancer is determined as described above, tissue level and/or activity level of the polypeptide (or mRNA thereof) of the present invention can also be utilized to stage the colon tumor and to thereby predict the prognosis of an individual diagnosed with colon cancer.

Such staging can be effected by assessing the tissue level and/or activity level of the polypeptide and correlating it to results obtained from colon cancer tissue at various stages (obtainable through pathological evaluation of colon tumors). It will be appreciated that such accurate and rapid staging will enable accurate and rapid prognosis of an individual afflicted with colon cancer and timely administration of suitable treatment regimen.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (Eds), "Basic and Clinical Immunology" (8th Edition), Appleton & Lange, Norwalk, Conn. (1994); Mishell and Shiigi (Eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

The Role of LOR1 in Angiogenesis

A study was conducted in efforts to further substantiate and characterize the role of LOR-1 in angiogenesis.
Materials and Methods Human recombinant platelet factor-4 (PF4, GenBank Accession number M20901) which was produced in bacteria and subsequently refolded was supplied by Dr. Maione of Repligen Corp. (Boston, USA). Estrogen slow release pellets were obtained from Innovative Research of America, Sarasota, Fla., USA.

Construction of LOR-1 Expression Vector, Transfection into MCF-7 Cells, and Expression:

The LOR-1 cDNA (SEQ ID NO:1) was cloned into a pCDNA3.1-hygro expression vector (Invitrogen Inc., USA) under the control of a CMV promoter. Clones of cells expressing LOR-1 were selected using hygromycine and assayed for LOR-1 expression using the polyclonal antisera described below.

Construction of Platelet Factor-4 Affinity Columns and Purification of LOR-1 on Such Columns:

PF4 was coupled to sepharose using a modification of the method of Miron and Wilchek (Wilchek and Miron, 1982) as previously described for vascular endothelial growth factor (Soker et al., 1998). Serum free conditioned medium was collected from $^{35}$S-methionine labeled MCF-7 cells which over-expressed LOR-1. The conditioned medium was passed through the column twice. The column was washed with phosphate buffered saline (300 mM NaCl, pH-7.2) and eluted with PBS (containing 2M NaCl).

Experiments with Nude Mice:

Modified or parental MCF-7 cells ($10^7$ cells per animal) were implanted under the skin of nude mice. A pellet of slow release estrogen was implanted 1 cm away as previously described (Zhang et al., 1995). Tumors were measured periodically, following which, tumors at least 1 cm in size were removed and immuno-histologically analyzed using a commercial antibody directed against a factor 8 like antigen which served as a specific marker for endothelial cells.

In-Situ Hybridization:

Fragments encompassing nucleotides 922-1564 of LOR-1, nucleotides 976-1391 of LOL, nucleotides 400-950 of LO and nucleotides 1061-1590 of LOR-2 (as numbered from the ATG codon of these sequences) where each independently subcloned into the Bluescript SK and KS (Strategene) vectors. A DIG cRNA labeling kit of Boehringer-Mannheim was used to transcribe sense (s) and antisense (as) digoxigenin-labeled cRNA probes from the T7 promoter of the Bluescript constructs. Hybridization and subsequent detection of hybridized probes was carried out essentially as previously described (Cohen et al., 2001).

Anti-LOR-1 Polyclonal Antisera:

Antisera was generated by injecting a recombinant peptide containing the C-terminal 200 amino-acids of LOR-1 (amino acids 540-744 of SEQ ID NO:2) into female rabbits. Serum was collected 10 days following each injection and an immunoglobulin fraction was purified using a protein A Sepharose affinity column (Pharmacia).
Results LOR-1 Purification:

A PF4 affinity column was used to detect endothelial cell proteins which specifically interact with PF4.

Two PF4 binding proteins were detected in conditioned medium of human umbilical vein endothelial cells (HUVEC), whereas PF4 binding proteins were not detected in detergent extracts of endothelial cells.

Two liters of conditioned medium enabled a partial purification of one such binding protein which eluted from the column at a relatively high salt concentrations (0.4-0.5 M NaCl).

Further purification of this protein was performed using reverse phase high pressure liquid chromatography and SDS/PAGE chromatography. The PF4 binding protein did not bind to heparin nor was it a heparan-sulfate proteoglycan since heparinase digestion failed to change its mobility in SDS/PAGE experiments.

Partial sequencing and database comparison revealed that the PF4 binding protein of the present invention (LOR-1) belongs to a family of proteins containing a lysyl oxidase like domain (Kim et al., 1995; Kim et al., 1999). Lysyl oxidases are copper dependent enzymes that participate in the synthesis of the extracellular matrix by catalyzing the formation of covalent bonds between lysines of adjacent collagen or elastin fibers.

The full length amino acid sequence of LOR-1 (as deduced from the isolated cDNA sequence) displayed a high degree of identity to WS9-14, a protein over expressed in senescent fibroblasts, in several types of adherent cells (but not in non-adherent cells) and in fibroblasts, in which it was correlated to pro-collagen I-al expression levels, as well as being induced by TGF-β and inhibited by phorbol esters and retinoic acid (Saito et al., 1997).

The Role of LOR-1 in Tumor Development:

Recombinant LOR-1 expressed in PAE cells specifically bound with the PF4 affinity column (FIG. 1). Since LOR-1 is a member of the LO family it was hypothesized that it participates in ECM formation during angiogenesis. Furthermore it was also hypothesized that PF4 suppresses or inhibits the pro-angiogenic activity of LOR-1 thus inhibiting the later stages of blood vessel formation and as a result limiting tumor growth.

LOR-1 Expression:

In-situ hybridization demonstrated that LOR-1 is expressed in a wide variety of tissues and cell types including fibroblasts, adipocytes, nerve cells, endothelial cells and a variety of epithelial cells. Several cell types, such as liver hepatocytes, did not express LOR-1; of the 4 LO family members examined (all except for LoxC) LOR-1 was the only one expressed in endothelial cells of blood vessels.

Figure 2:
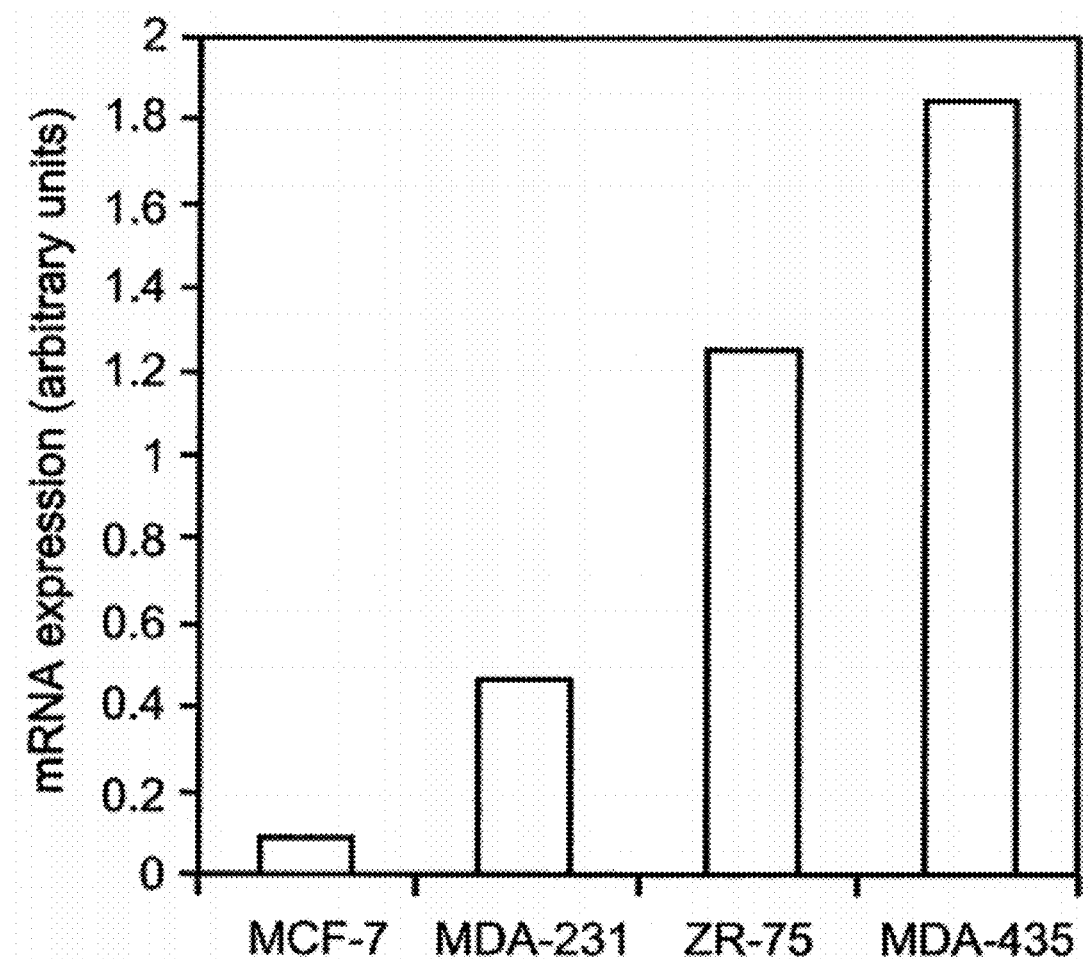
FIG. 2 illustrates differential expression of LOR-1 in breast cancer derived cells of different metastatic potential. The metastatic potential of the cells increases from left to right, and is correlated to increased LOR-1 mRNA expression. The results correspond to northern blot analysis of LOR-1 mRNA expression. Data regarding the relative metastatic potential of the cell lines was derived from the literature.

LOR-1 and Cancer:

as shown in FIG. 2, a direct correlation between the expression levels of LOR-1 and the metastatic properties of breast cancer derived cell lines was demonstrated herein.

Since the epithelial cells which line the milk ducts of normal breast tissue (from which most breast tumors arise) express large amounts of LOR-1 it is possible that the less metastatic lines lost LOR-1 expression rather than gained it.

To substantiate its role in metastasis, LOR-1 cDNA was expressed in non-metastatic breast cancer derived MCF-7 cell lines which do not normally express LOR-1. The expression of LOR-1 was examined using rabbit polyclonal antibodies generated as described above (FIG. 3).

A control cell line which was transfected with an empty expression vector, and an MCF-7 cell line expressing LOR-1 were implanted under the skin of immune deficient mice along with an estrogen slow release pellet as described above. Estrogen was added since the development of tumors from this non-metastatic cell line is estrogen dependent (Mcleskey et al., 1993).

Figure 4:
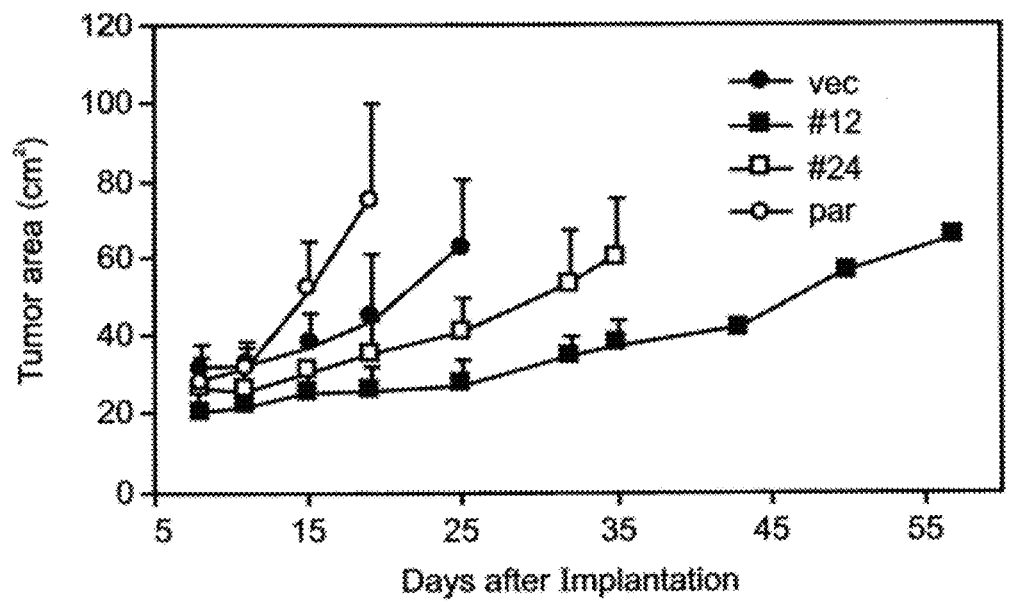
FIG. 4 illustrates tumor size as correlated to LOR-1 expression. Parental MCF-7 cells (par), MCF-7 cells transfected with pCDNA3 vector alone (vec) and two recombinant LOR-1 expressing MCF-7 cells (clones 12 and 24) were deposited under the skin of immune deficient mice ($10^7$/injection site) along with an estrogen slow release pellet. Six animals were used for each cell type implanted. The area of the tumors was measured every few days. Bars represent standard deviation from the mean.

The rate of tumor development in the mice was continuously monitored (FIG. 4); tumors 1 cm in size were excised and subjected to histological analysis as described above. Interestingly, the rate of tumor development varied between the two cell lines, with some tumors exhibiting slower growth in the LOR-1 expressing MCF-7 and yet other exhibiting slower growth in the control cells.

In order to overcome expression level problems, LOR-1 cDNA was placed under the control of a tetracycline induced promoter (The TET-off system). Such a construct will enable to determine conclusively whether the reduced rate of tumor growth observed in LOR-1 expressing cells is indeed caused by LOR-1.

Figure 5A:
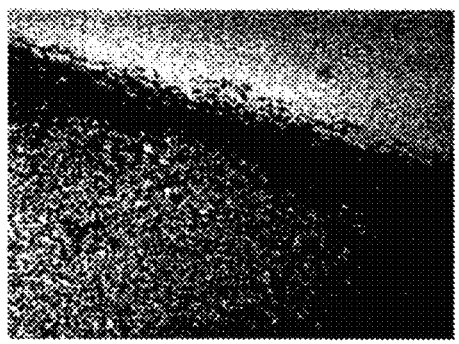
FIGS. 5a-b illustrate anti-factor-8 immunostaining of tumors generated by MCF-7 cells transfected with the expression vector alone (FIG. 5a) or with an expression vector containing the LOR-1 cDNA (FIG. 5b). Counter staining was performed with Hematoxylin-eosin (blue). Invasion of blood vessels into the tumor mass is more abundant in LOR-1 expressing tumors (FIG. 5b) as compared to tumors generated by control cells which do not express LOR-1 (FIG. 5a).
Figure 5B:
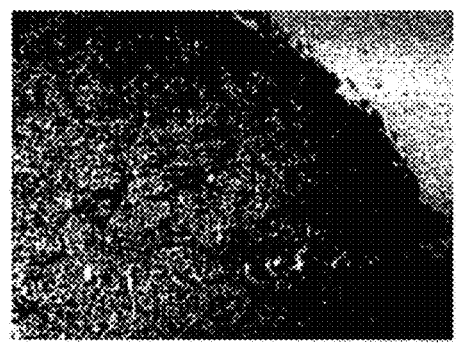

Tumors expressing large amounts of LOR-1 were sectioned and stained with an antibody directed against factor 8 like antigen, a specific marker of endothelial cells. Control tumor tissue predominantly stained at the capsule around the tumor while in the LOR-1 expressing tumors pronounced staining was observed in inner regions of the tumor tissue (FIG. 5a and FIG. 5b respectively).

Figure 6A:
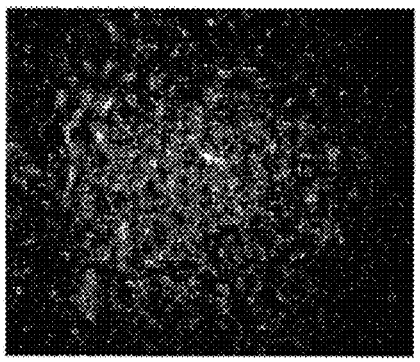
FIGS. 6a-d illustrate liver sections of Wilson's disease patients (FIGS. 6c-d) and normal patients (FIGS. 6a-b) probed with a LOR-1 sense probe (FIGS. 6a, 6c) and antisense probe (FIGS. 6b, 6d).
Figure 6B:
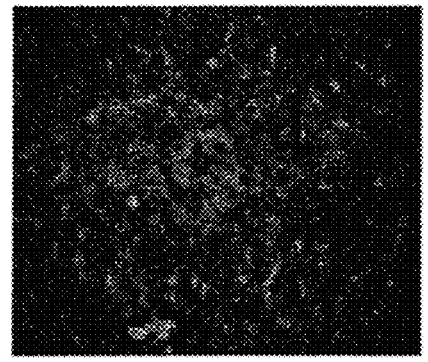
Figure 6C:
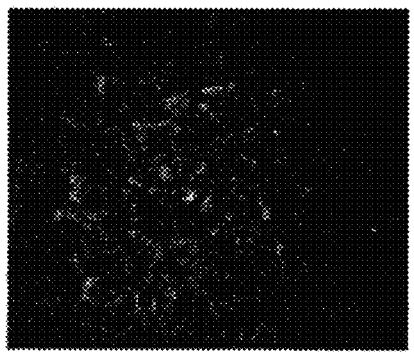
Figure 6D:
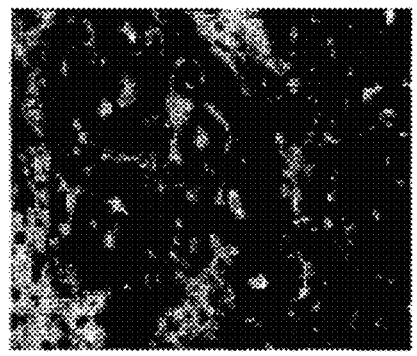

The Role of LOR-1 in Wilson's Disease and in Other Chronic Liver Diseases:

Normal and diseased liver tissue were probed with LOR-1 sense (FIGS. 6a and 6c) and antisense probes (FIGS. 6b and 6d). Normal liver tissues expresses very low levels of LOR-1 (FIG. 6b). However, fibrotic liver tissues such as those observed in Wilson's disease, exhibit a strong increase in hepatocyte expression of LOR-1 (FIG. 6d).

Figure 7:
FIG. 7 illustrates results of a whole mount in-situ hybridization using a LOR-1 cDNA probe and a 4 day old chick embryo. Strong expression of LOR-1 mRNA is observed in amniotic blood vessels (arrow).

Expression of LOR-1 in Chick Embryos:

FIG. 7 illustrates LOR-1 expression of LOR-1 mRNA in blood vessels of a developing chick embryo. Whole-mount in-situ hybridization of 4 day old chick embryos revealed LOR-1 mRNA expression in blood vessels located in the amnion (arrow).

The Lysyl Oxidase Family:

A homology comparison between five members of the lysyl oxidase family which includes the LO and LOL subfamily and the LOR-1 and LOR-2 subfamily revealed a strong homology at the C-terminal portion which includes the conserved lysyl oxidase motif. LOR-1 and LOR-2 are characterized by long N-terminal stretches which are not found in LO and LOL.

Example 2

MCF-7 Breast Cancer Cells Expressing Recombinant Lysyl Oxidase Related Protein-1 (LOR-1) Form Invasive Tumors Characterized by Extensive Fibrosis A study was conducted in efforts to further substantiate and characterize the role of LOR-1 in inhibiting metastasis and tumor fibrosis.

Materials and Methods

Estrogen pellets (17β-estradiol, 0.72 mg/pellet, 60-days release) were from Innovative Research of America, Fla., USA. Masson Trichrome stain kit was purchased from Bio-Optica (Milano, Italy), Reverse Transcriptase, G418 were from GIBCO BRL (U.K.), Hygromycin B, Tetracycline hydrochloride, Reticulum stain kit fast green and Sirius red (direct red 80) were from Sigma (USA), Restriction enzymes, T4 ligase were from New England Biolabs (USA). The bacterial expression vector pQE-30 and the nickel affinity column were obtained from Qiagen (Germany), $^{32}$p-dATP was purchased from NEN (USA). Monoclonal anti cytokeratin-7 (CAM 5.2) coupled to FITC was acquired from Becton Dickinson (USA), and monoclonal mouse anti vimentin (clone V9) was purchased from DAKO Denmark). Anti FITC alkaline phosphates-conjugated was purchased from ROCHE (USA), CAS block, citrate and EDTA antigen retrieval buffers were from Zymed (USA).

Cell Culture:

MCF-7 breast cancer cells were kindly provided by Dr. Hadasa Degani (Weizmann Institute, Israel). The MDA-MB-435 breast cancer cell line was kindly provided by Dr. Israel Vlodaysky (Technion, Israel). The MDA-MB-231 cells were kindly provided by Dr. Michael Klagsbrun (Harvard University, USA). These cell lines were routinely cultured in Dulbecco's modified eagle medium supplemented with gentamicin, amphotericin, glutamine and 10% Fetal Calf Serum (FCS). Human umbilical vein derived endothelial cells were isolated and cultured as described (Neufeld and Gospodarowics, 1988). Tissue culture media, sera, and cell culture supplements were from Beth-Haemek Biological Industries, Israel, or from Gibco-BRL. MCF-7 TetOff cells (Clontech, USA) containing the tetracycline trans-activator (tTA) were grown in DMEM medium containing 10% Tet system approved fetal calf serum (Clontech), in the presence of 100 µg/ml G418, 150 µg/ml Hygromycin B and 1 µg/ml Tetracyclin.

Cloning of the LOR1 and LOR2 cDNA:

Total RNA (4 µg) from HUVEC cells (for LOR1) or melanoma cells (for LOR2) was reversed transcribed using MMLV reverse transcriptase (GIBCO BRL) as described (Chomczynski and Sacchi, 1987). The LOR-1 and LOR-2 cDNAs were amplified using the Expand Long High Fidelity PCR system (ROCHE) and the following pairs of amplification primers: For LOR-1 SEQ ID NOs:10 and 11, and for LOR-2 SEQ ID NOs:12 and 13. The 2.3 kb cDNA of LOR-1 (SEQ ID NO:1) and the 2.26 KB of LOR-2 (SEQ ID NO:4) were subcloned into the pGEM-T Easy vector (Promega) by T-A cloning.

Generation of Polyclonal Antibodies Against Human LOR1:

A cDNA fragment containing nucleotides 1641-2253 of LOR1 (SEQ ID NO:14) was amplified using the Expand High Fidelity PCR kit and a pair of amplification primers (SEQ ID NOs:15 and 16). The PCR product was subcloned into the pGEM-T Easy vector (Promega) by T-A cloning.

A 613 by LOR1 cDNA fragment (SEQ ID NO:14) was digested with the Sph-I and Hind III restriction enzymes and ligated into the bacterial expression vector pQE-30, which added an in-frame sequence encoding a six histidine (6×His) tag to the 5' end of the insert. The resulting plasmid was used to produce a recombinant, 6×His tagged 23 kDa peptide (SEQ ID NO:17). The peptide was purified from bacterial cell extracts using nickel affinity chromatography, and further purified using SDS-PAGE. The gel was electroblotted onto nitrocellulose and the band containing the peptide was cut out from the blot, solubilized in DMSO, and used to immunize rabbits. Antiserum was affinity purified on protein-A sepharose followed by affinity purification on a column to which the recombinant peptide was coupled using a previously described method (Wilchek and Miron, 1982). The antibody was eluted from the column using 0.1 M glycine at pH 3.

Figure 10A:
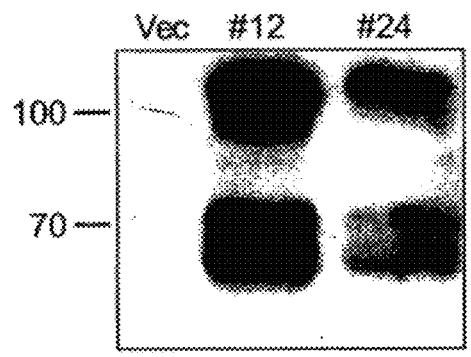
FIG. 10a illustrates the expression of recombinant LOR-1 in MCF-7 cells transfected with the expression vector alone (vec) or with an expression vector containing the LOR-1 cDNA clone 12 or 24 (#12 or #24, respectively). LOR-1 proteins were detected by Western blot with an antibody directed against the C-terminal of human LOR-1.

Transfections:

To constitutively express LOR1, the full length LOR1 cDNA (SEQ ID NO:1), was digested out of the pGEM-T easy vector (Promega) with Hind III and XbaI (which were incorporated into the primers used for the cloning of the LOR1 cDNA) and ligated into the mammalian expression vector pcDNA3.1 Hygro (Invitrogen, USA) to generate the expression vector pcDNA-LOR1. Empty pCDNA3.1 Hygro plasmid or pcDNA-LOR1 plasmid (10-20 µg) were stably transfected into MCF-7 cells using electroporation with a BioRad gene pulser (960 µF, 0.28 V). Stable transfectants were selected using 300 µg/ml hygromycin B. Clones expressing recombinant LOR1 were obtained in two consecutive stable transfections and screened for LOR1 expression using our anti-LOR-1 polyclonal antibodies. Conditioned medium was collected after 48 hours from transfected cells and LOR-1 expression was monitored using western blot analysis (FIG. 10A).

To inducively express LOR1, full length LOR1 cDNA (SEQ ID NO:1) was cloned into the pTET-Splice vector (Clontech), which enables an inducible expression under the control of tetracycline (Tet off system). The pTET-Splice plasmid DNA was digested with Hind III and SpeI and ligated to the 2.3 kb hLOR1 cDNA fragment which was rescued out of the pCDNA-LOR1 plasmid using Hind III and XbaI. The resultant plasmid, which was designated as pTET-LOR1, was co-transfected into MCF-7 TetOff cells along with pTK-Hygro at a ratio of 20:1 respectively. LOR-1 expressing cells were selected in medium containing 100 µg/ml G418, 150 µg/ml hygromycin B and 1 µg/ml tetracycline. Stable transfectants were screened for inducible expression of LOR1 using western blot analysis 48 hours following removal of the tetracycline from the growth media. The clone having the highest induction levels in the absence of tetracycline and lowest basal expression levels in the presence of tetracycline was selected and designated MCF-7/Tet-LOR1.

C6 glioma cells were transfected and screened for LOR1 expression as described above.

Northern Blot Analysis:

Total RNA was extracted from cultured cells using Tri-Reagent (MRC, Cincinnati) according to the manufacture's instructions. Total RNA (15 µg) was loaded on a 1.2% agarose gel and Northern blot analysis was carried out as previously described (Cohen et al., 2001). LOR-1 and LOR-2 $^{32}$P labeled cDNA fragments; nucleotides 1-660 of SEQ ID NO:18 and 1061-1590 of SEQ ID NO:19 (respectively) were used as probes.

Protein Blot Analysis:

Serum free conditioned media (40 µl) was separated on a 8% SDS-PAGE gel and the proteins were electroblotted onto a nitrocellulose filter using semi-dry electroblotting. The filter was blocked for 1 hour at room temperature with TBST buffer containing 10 mM Tris-HCl (pH-7.0), 0.15 M NaCl, and 0.3% Tween-20 supplemented with 10% low fat milk. The filter was incubated over night at 4° C. with affinity purified rabbit anti-LOR1 polyclonal antibody in TBST (1:2500). The blot was subsequently washed 3 times in TBST and incubated with goat anti-rabbit IgG peroxidase-conjugated secondary antibodies for 1 hour at room temperature. Bound antibody was visualized using the ECL detection system (Biological Industries, Israel).

Nude Mice Experiments:

Slow release pellets containing 17β-estradiol (0.72 mg/pellet, 60 day release, Innovative Research) were pre-implanted subcutaneously in 6-8 weeks old female athymic nude mice (CD1). MCF-7 cells ($10^7$ cells/mouse) were injected into the mammary fat pads. Tumor size was measured with a caliper once or twice a week, and tumor volume was determined using the following formula: volume=width$^2$×length×0.52 (O'Reilly et al., 1999). Mice were sacrificed 4 weeks following injection of the MCF-7 cells. In other experiments, the tumors were excised when reaching a diameter of 0.8 cm. The primary tumor, the liver and the lungs were removed, weighted, fixed in 10% buffered formalin and embedded in paraffin.

The development of tumors from C6 glioma cells expressing recombinant LOR-1 was also studied. Cells ($2×10^5$ cells/animal) transfected with a control expression vector or with an expression vector containing LOR1 cDNA were injected subcutaneously in the hind limb. Mice were sacrificed 3 weeks after the injection of the cells. The primary tumors were removed, fixed in 10% buffered formalin, and embedded in paraffin for analysis.

Histology and Immunohistochemistry:

Formalin-fixed, paraffin-embedded tissues were cut into serial sections of 5 µm each and used for immunohistochemistry. Sections were deparaffinized by heating to 60° C. for 1 hour, washed twice with xylen for 5 min and rehydrated by consecutive washes in 100%, 95%, and 70% ethanol followed by a wash in water. Endogenous peroxidase activity was inhibited by a 15 minute incubation with 3% hydrogen peroxide in methanol, followed by washes with water and PBS. The sections were then antigen retrieved by heating twice for 10 minutes in a microwave oven to 90° C. in citrate buffer at pH-6.2 (for cytokeratin and vimentin antibodies) or in 1 mM EDTA buffer (for LOR1 antibody); blocking was performed using CAS block (Zymed). Following blocking, the sections were incubated for 1.5 hr at room temperature with the following antibodies, all diluted with in antibody diluent reagent solution (Zymed): affinity purified anti-LOR1 antibody (1:30-1:50), monoclonal anti human cytokeratin-7 antibodies-FITC conjugated (1:50), or with monoclonal antibodies directed against vimentin (1:50). The sections were then washed 3 times with TBST, and secondary detection was applied using anti FITC alkaline phosphates-conjugate (Roche) at a 1:200 dilution (for anti cytokeratin) or DAKO Envision detection system (anti rabbit or anti mouse—HRP). Sections were developed in 3-amino-9-ethylcarbazole (AEC, DAKO) solution, counterstained by Hematoxylin, and photographed under a microscope. In control experiments the primary antibodies were omitted. Masson Trichrome and reticulum stains were according to manufacturer's protocol. For Sirius red stain sections were incubated for 5 min. with 0.03% (w/v) fast green solution, rinsed twice with 1% acetic acid, incubated for 15 min in 0.1% Sirius red solution, rinsed as above, dehydrated and examined under polarizing light microscope.

Experimental Results

Figure 9A:
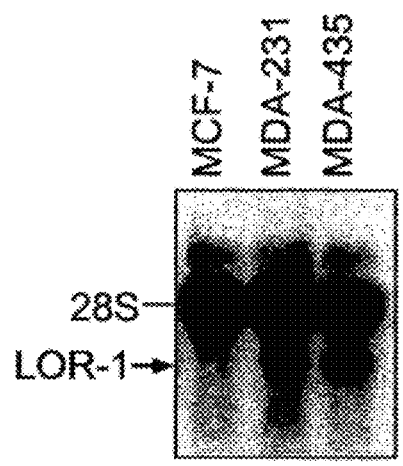
FIGS. 9a-b. illustrate the expression of LOR-1 and LOR-2 in human breast cancer derived cells: Total RNA was prepared from confluent MCF-7 cells (MCF-7), MDA-MB-231 cells (MDA-231) and MDA-MB-435 cells (MDA-435) and was subjected to Northern blot analysis using a LOR-1 (FIG. 9a) and LOR-2 (FIG. 9b) specific cDNA probes. LOR-1 specific hybridization signal is seen in tumors derived from both MDA-231 and MDA-435 cells but not in tumors derived from MCF-7 cells. LOR-2 specific hybridization signal is seen only in tumors derived from MDA-435 cells. LOR-1 and LOR-2 non-specific hybridization signals are seen in all tumors' RNA in a band that corresponds to the 28S rRNA.
Figure 9B:
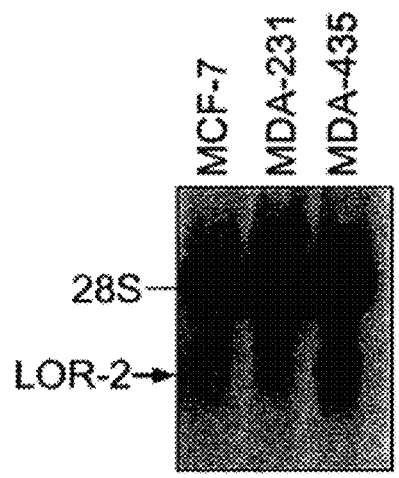
Figure 9C:
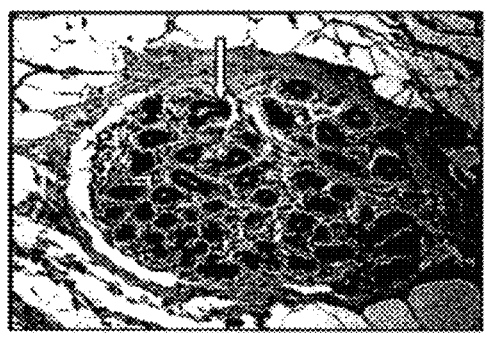
FIGS. 9c-f illustrate the expression pattern of LOR-1 in normal human breast (FIG. 9c), in in-situ non-invasive breast carcinoma (FIG. 9d), in grade-1 invasive ductal carcinoma (FIG. 9e) and in grade-3 invasive ductal carcinoma (FIG. 9f). A polyclonal affinity purified rabbit antibody directed against the C-terminal of LOR-1 was used to detect the expression of LOR-1. High level expression of LOR-1 protein is seen in the epithelium of the normal duct (FIG. 9c, open arrow); magnification ×100. In in-situ non-invasive breast carcinoma (FIG. 9d) the cancer cells have filled the duct but are still confined to it. Many of the cells located at periphery of the tumor have lost their ability to express LOR-1, while at the center, the cells still express high levels of LOR-1 (FIG. 9d, empty arrow); magnification ×200. In grade-1 invasive breast carcinoma the tumorigenic cells have formed pseudo-ducts (FIG. 9e, black arrows) but they do not express LOR-1 anymore. However, cells found in a nearby carcinoma in-situ express LOR-1 (FIG. 9e, empty arrow); magnification ×200. In grade-3 invasive breast carcinoma the tumorigenic cells express large amounts of LOR-1 and the morphology is completely disorderly (FIG. 9O; magnification ×200.

LOR-1 is Expressed in Highly Metastatic Breast Cancer Derived Cell Types but not in Non-Metastatic MCF-7 Cells:

Desmoplasia and formation of fibrotic foci in breast cancer tumors is associated with the transition from a localized, relatively benign tumor to an invasive/metastatic tumor (Colpaert et al., 2001; Hasebe et al., 2000). Lysyl oxidases contribute to the deposition of collagen by covalently cross-linking collagen monomers (Smith-Mungo and Kagan, 1998). To find out whether expression of lysyl oxidases is associated with the invasive/metastatic phenotype several human breast cancer derived cell types have been screened for the expression of lysyl oxidases. Northern blot analysis revealed that the LOR-1 gene is expressed in the highly malignant, hormone independent MDA-MB-231 and MDA-MB-435 cells (Price et al., 1990) but not in hormone dependent non-metastatic MCF-7 cells (FIG. 9a). LOR-2 on the other hand was expressed only in MDA-MB-435 cells but not in the MDA-MB-231 or in MCF-7 cells (FIG. 9b).

Figure 9D:
Figure 9E:
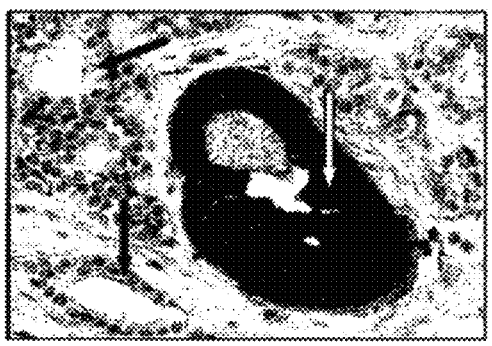
Figure 9F:
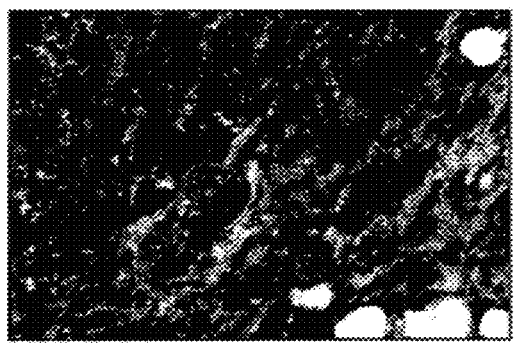

Highly malignant grade 1 breast carcinoma cells do not express LOR-1 while highly malignant cells of grade 3 carcinomas express LOR-1: LOR-1 expression was confined to the milk ducts in both normal breast (FIG. 9c) and in in-situ ductal carcinoma (FIG. 9d). However, in grade 1 well-differentiated ductal breast carcinoma, wherein the tumor cells migrate out of the ducts to form pseudo ducts, the cells do not express LOR-1 (FIG. 9e, black arrows). On the other hand, the cells of grade 3 ductal breast carcinoma tumors, a highly malignant tumor characterized by desmoplasia, express high levels of LOR-1 (FIG. 9f).

Tumors Generated in Mice from LOR-1 MCF-7 Transfected Cells have a Slower Growth Rate:

In order to determine whether LOR-1 expression contributes to the progression of breast tumors and to the invasive/metastatic phenotype, non-invasive MCF-7 cells have been transfected with an expression plasmid containing LOR-1 cDNA (SEQ ID NO:1). Several transfectant clones have been isolated and selected for their LOR-1 expression. The conditioned medium of two LOR-1 expressing clones (clone 12 and 24) and of a clone transfected with an expression vector alone (vec) was assayed with LOR-1 antibodies directed against the C-terminal portion of LOR-1 (SEQ ID NO:17). Western blot analysis revealed higher levels of LOR-1 expression in clone 12 cells as compared with clone 24 cells, and no expression in cells transfected with the expression vector alone (FIG. 10a).

Figure 10B:
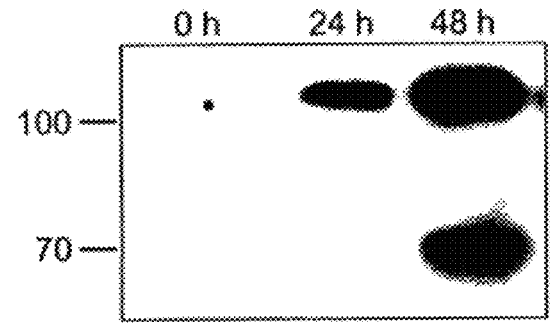

In addition, both LOR-1 expressing cells displayed extra protein bands of about 70 kDa (FIGS. 10a, b) suggesting that LOR-1 may undergo proteolytic processing like other members of the lysyl oxidase family (Borel et al., 2001; Panchenko et al., 1996). To verify that the low molecular weight forms are produced as a result of post-translational processing, LOR-1 cDNA has been expressed in MCF-7 cells under the control of a Tetracycline inducible promoter (Shockett and Schatz, 1996). It can be seen that once the tetracycline inhibition is removed, the cells start to produce full length LOR-1 which is then converted into a shorter, 70 kDa C-terminal containing form (FIG. 10b). It is not yet clear whether all of these forms are enzymatically active.

Figure 10C:
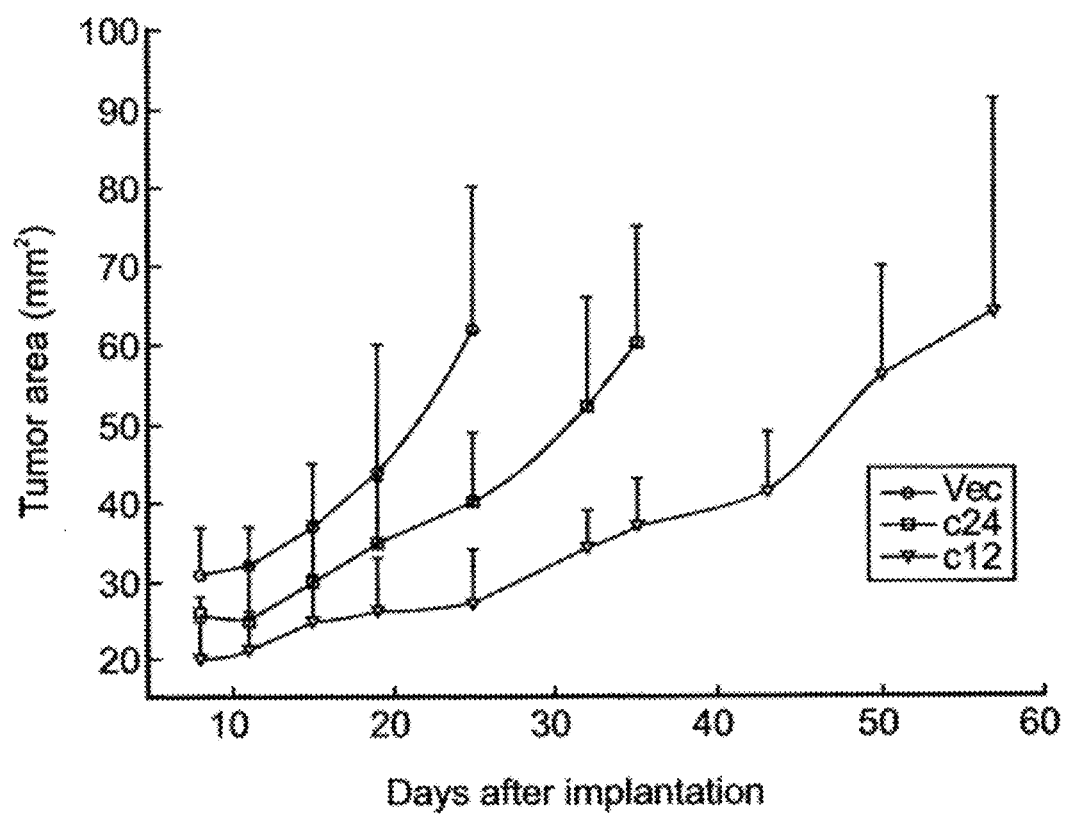
FIG. 10c illustrates the growth rate of tumors derived from control or LOR-1 expressing MCF-7 cells. MCF-7 cells transfected with the expression vector alone (vec) or with an expression vector containing the LOR-1 cDNA clone 12 or 24 were injected into the mammary fat pads of female athymic nude mice. Each cell type was implanted in 8 animals. Tumor area was measured at the indicated times. Error bars represent the standard error of the mean. The experiment was terminated and the mice sacrificed when the tumor reached a diameter of about 1 cm.
Figure 10D:
FIG. 10d illustrates the relative size of tumor in mice 25 days following injection of MCF-7 cells. Shown are mice harboring tumors that developed from cells transfected with the expression vector alone (left) or with the expression vector containing LOR-1 cDNA clone 24 (center) or 12 (right).

To substantiate its role in tumor growth and metastasis LOR-1 producing cells and cells transfected with expression vector alone were pre-implanted subcutaneously in nude mice (described above). Interestingly, the growth rate of tumors containing LOR-1 expressing cells was retarded as compared with that of tumors developed from parental cells or cells transfected with the expression vector alone (FIGS. 10c, d).

To determine if the decreased tumor growth rate was a result of slower proliferation, the proliferation rate of empty vector transfected MCF-7 with that of clone 12 and clone 24 cells were also compared; significant differences in their rates of proliferation was not detected.

Figure 11A:
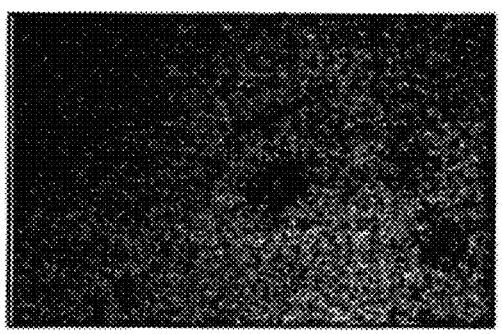
FIGS. 11a-h illustrate fibrotic foci and collagen deposits in tumors derived from MCF-7 cells expressing recombinant LOR-1. Hematoxylin-eosin staining demonstrate a few necrotic foci in a tumor derived from MCF-7 cells transfected with expression vector alone (FIG. 11a, arrow, magnification ×20) and numerous necrotic foci in a tumor derived from MCF-7 cells transfected with expression vector containing LOR-1 cDNA clone 12 (FIG. 11b, arrows, magnification ×20).
Figure 11B:
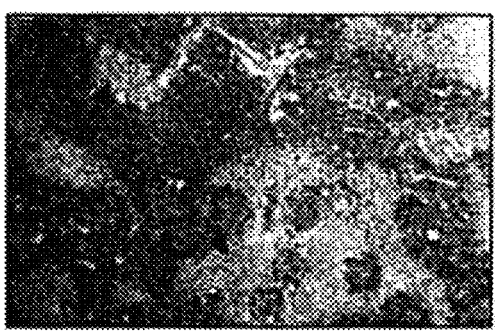

Tumors that Develop from LOR-1 Producing MCF-7 Cells Contain Many Necrotic and Fibrotic Foci Rich in Collagen Deposits:

Hematoxylin-eosin staining of tumor sections revealed major necrosis in tumors generated from LOR-1 expressing MCF-7 cells (FIG. 11b) and only a few necrotic areas in tumors generated from parental or MCF-7 cells transfected with expression vector alone (FIG. 11a).

Figure 11C:
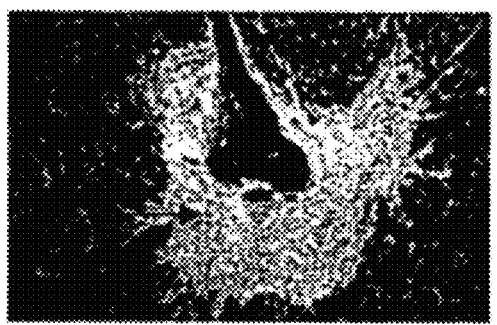

LOR-1 expressing tumors also contained extensive fibrotic areas mainly composed of host derived cells such as mouse fibroblasts rather than MCF-7 cells. These cells are easily distinguishable from the host cells since they do not react with an antibody against human keratin 7 (FIG. 11c).

Figure 11D:
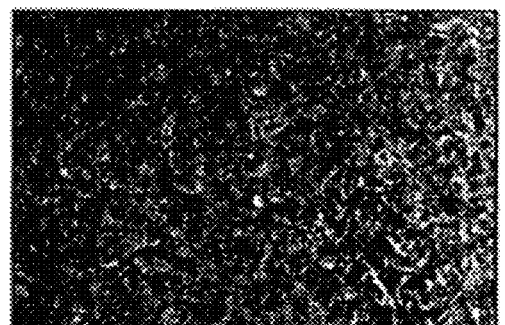
Figure 11E:
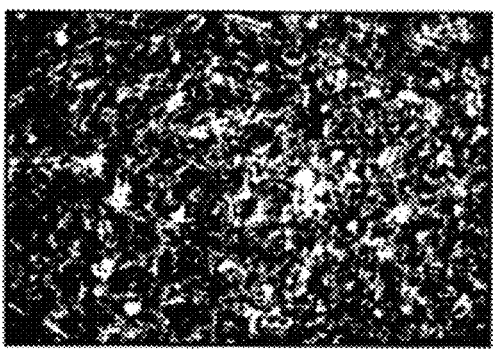
Figure 11F:
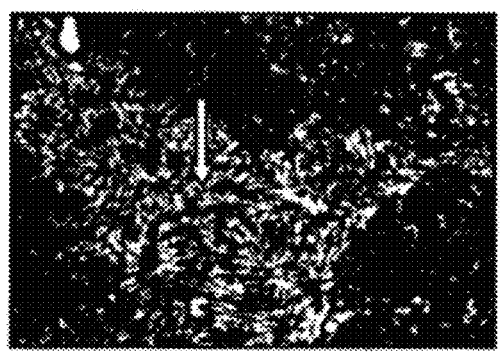
Figure 11G:
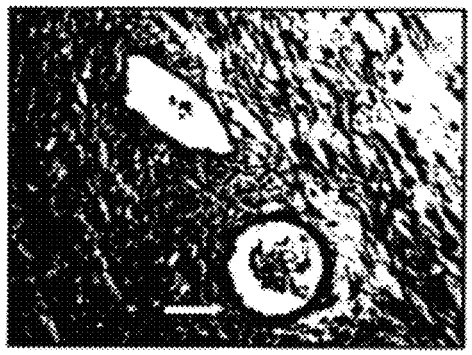
Figure 11H:

Since LOR-1 was shown to oxidize lysine residues on collagen-I (Vadasz et al., 2002) it was anticipated that it may induce collagen cross-linking and deposition. However, this activity is probably depended on the existence of collagen since LOR-1 expressing MCF-7 cells grown in culture do not produce more collagen than parental MCF-7 cells. To further understand the involvement of LOR-1 in tumor progression tumors derived from LOR-1 expressing MCF-7 cells have been stained with Mason's Trichrome, a reagent that reacts primarily with collagen-I and produces an azure color (Pinder et al., 1994). (1) Tumors that developed from parental or MCF-7 cells transfected by an expression vector alone contained limited amounts of collagen that was scattered between the tumor cells (FIG. 11d, arrows). In-contrast, tumors that developed from clone 12 or clone 24 LOR-1 expressing MCF-7 cells contained denser deposits of collagen between the tumor cells (FIG. 11e). Furthermore, the fibrotic and necrotic areas in these tumors appeared choke full with collagen fibers (FIG. 11f). In addition, while the blood vessels within tumors that developed from vector-transfected MCF-7 cells remained almost unstained (FIG. 11g, arrows), the blood vessels in tumors derived from LOR-1 expressing MCF-7 cells were sheathed by a thick layer of collagen (FIG. 11h, arrows).

Figure 12A:
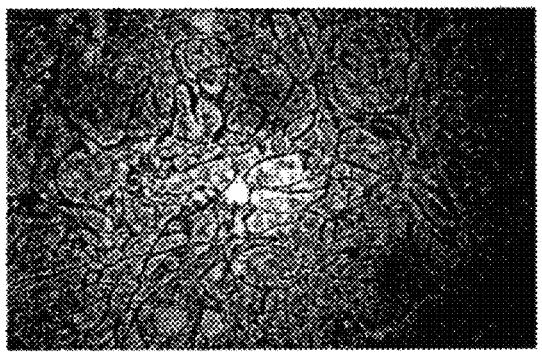
FIGS. 12a-d illustrate the deposition of collagen type-3 by reticulum stain in tumors generated from MCF-7 and C6 glioma cells transfected with expression vector alone (FIG. 12a, c) or vector expressing LOR-1 cDNA clone 12 (FIG. 12b,d); magnification ×200.
Figure 12B:
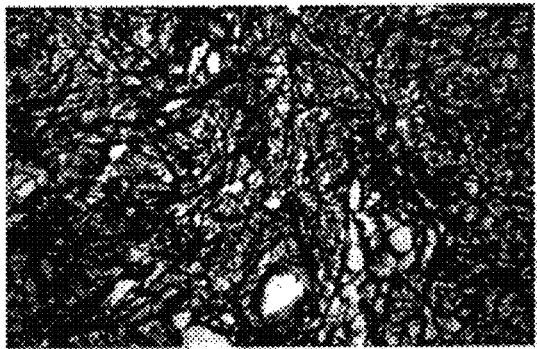
Figure 12C:
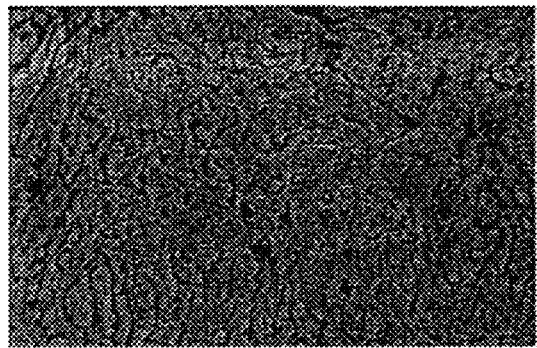
Figure 12D:
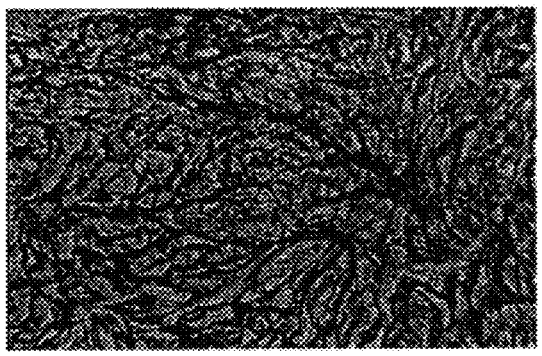

These experiments indicate that LOR-1 affects both collagen-I production and deposition in MCF-7 derived breast cancer tumors. To substantiate the involvement of LOR-1 in collagen deposition C6 glioma cells were also subcutaneously injected into mice. While tumors generated from C6-glioma cells did not contain large amounts of collagen, tumors generated from LOR-1 expressing C6-glioma cells were rich with collagen. These results indicate a more general effect for LOR-1 on collagen-I deposits in tumors. In addition, Reticulum staining of collagen-III revealed that tumors generated from LOR-1 expressing MCF-7 or C6-glioma cells contained thicker and higher concentrations of collagen-III fibers (FIG. 12b, 12d) as compared with tumors generated from cells transfected with the expression vector alone (FIGS. 12a, c).

Figure 13A:
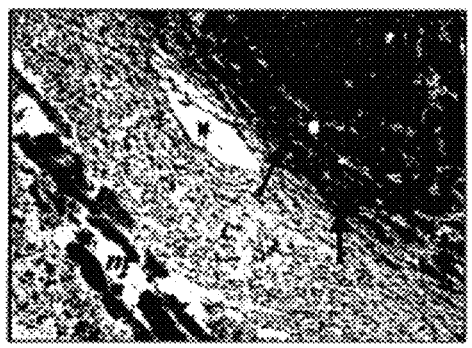
FIGS. 13a-h illustrate the invasiveness of tumors derived from MCF-7 cells expressing recombinant LOR-1. Shown are histological sections of tumors generated from MCF-7 cells transfected with an expression vector alone (FIGS. 13a, b) or a vector expressing LOR-1 (FIGS. 13c-h). Sections were labeled with either a monoclonal antibody specific to human keratin-7 (FIGS. 13a-d and f-h, blue purple stain) or with an antibody directed against LOR-1 (FIG. 13e, red stain). Counterstain was with Hematoxylin (light blue) in all sections. Black arrows designate cytokeratin-7 positive tumor cells invading the tumor pseudo-capsule (FIG. 13c), infiltrating between adjacent muscle bundles (FIG. 13d), or invading the vasculature (FIGS. 13f, g) and peri-neural space of nerves (FIG. 13h). White arrows designate LOR-1 positive tumor cells infiltrating muscles located next to the tumor (FIG. 13g). Blood vessels v; nerves n; muscle fibers m; magnification ×100 for FIGS. 13a-c, f, h and ×200 for FIGS. 13d, e, g.
Figure 13B:
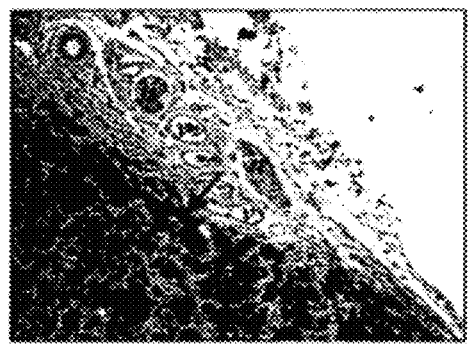
Figure 13C:
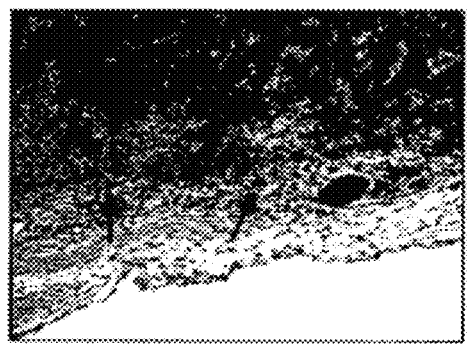
Figure 13D:
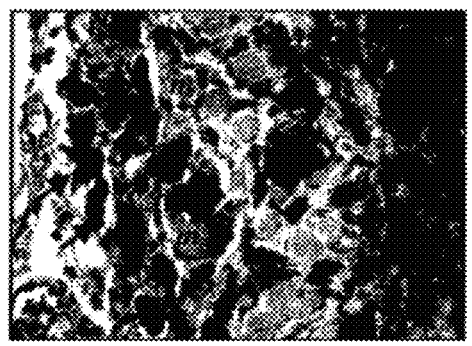
Figure 13E:
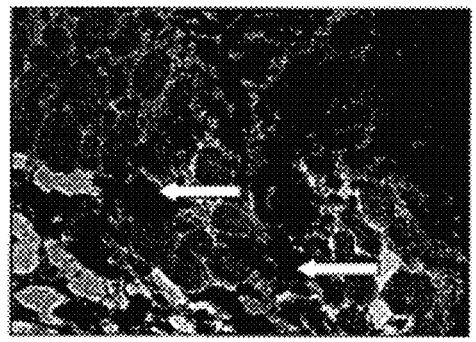
Figure 13F:
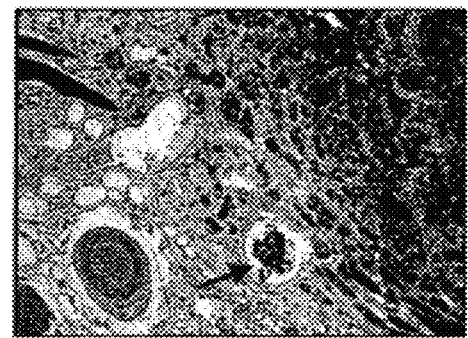
Figure 13G:
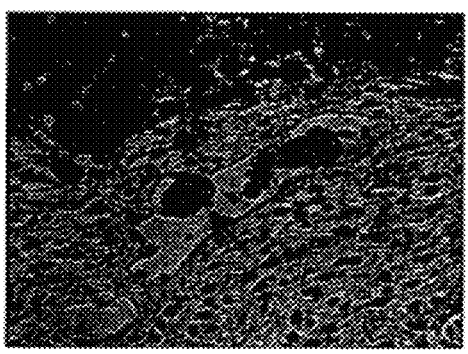
Figure 13H:
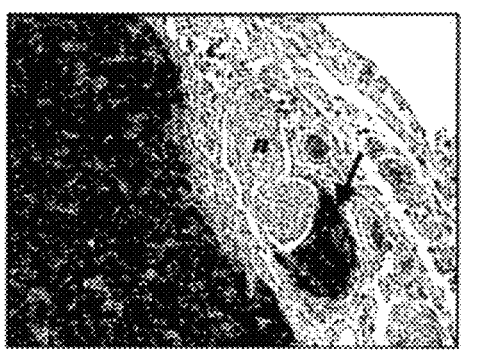

Expression of LOR-1 in MCF-7 Cells Transforms the Cells into Invasive Cells In-Vivo:

It was reported that the appearance of fibrotic foci in breast cancer tumors correlates with their degree of invasiveness (Hasebe et al., 2000). To substantiate the involvement of LOR-1 in tumor invasiveness human keratin-7 staining was employed. Tumors generated from MCF-7 cells transfected by the expression vector alone were surrounded by thick capsules with sharp borders. No staining of human keratin-7 was observed within the capsule (FIG. 13a) or in between blood vessels, nerves and muscles located adjacent to the capsules (FIG. 13b, arrows). In contrast, in tumors generated from LOR-1 expressing MCF-7 cells, human keratin-7 positive cells were observed within the capsule (FIG. 13c). Furthermore, in many areas the tumor cells migrated on-mass through the capsule and invaded muscles (FIG. 13d), nerves (FIG. 13e) and blood vessels (FIG. 13f). The invading cells were identified as the transfected LOR-1 expressing MCF-7 cells using an anti-LOR-1 antibody (FIG. 13g). These observations provide a strong evidence that the production of LOR-1 by breast cancer tumor cells contribute to the transition from localized non-invasive tumors to invasive tumors. Furthermore, aggregates of tumor cells were also detected inside lymph vessels adjacent to the tumors indicating that the LOR-1 expressing MCF-7 cells are metastatic (Luna, 1968).

Example 3

LOR-1 Expression is Correlated with the Malignancy of Colon Tumors

To study the correlation between LOR-1 expression and the malignancy of colon tumors various colon tumor sections were subjected to immunohistochemistry staining using an antibody directed against LOR-1.

Experimental Results

Figure 14B:

LOR-1 is Moderately Expressed in Benign Colon Tumors:

Normal colon tissues and benign colon tumors including hyperplasia and adenoma tissues were subjected to immunohistochemistry using an antibody directed against the C-terminal of human LOR-1. As is shown in FIGS. 14a-b, while low level of LOR-1 expression was seen in a few cells of the normal colon tissue (FIG. 14a), a moderate level of expression was detected in the hyperplasia tissue and a substantial level of expression was detected in cells comprising the adenoma tissue of the benign colon tumors (FIG. 14b). Thus, these results demonstrate that the expression of LOR-1 correlates with the formation of benign colon tumors.

Highly Malignant Colon Tumors Express High Levels of LOR-1:

To further substantiate the correlation between LOR-1 and the progression of colon tumors, low- and high-grade colon adenocarcinoma tissues were subjected to LOR-1 immunohistochemistry. As is shown in FIGS. 14c-d, a high level of LOR-1 expression was detected in both low-grade and high-grade adenocarcinoma tissues. However, while in low-grade adenocarcinoma the expression of LOR-1 was mainly confined to the carcinoma structures, (FIG. 14c, arrows), in the more malignant, high-grade colon adenocarcinoma high levels of LOR-1 expression was detected throughout the disorganized tumor tissue. These results demonstrate that a high level of LOR-1 expression is correlated with more malignant colon tumors.

Altogether these results demonstrate that LOR-1 expression is correlated with the progression of colon cancer and suggest the use of LOR-1 in determining the staging of colon cancer tumors.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. Folkman, J. (1990) What is the evidence that tumors are angiogenesis dependent. J. Nat. Cancer Inst. 82, 4-7.
2. Hanahan, D. and Folkman, J. (1996) Patterns and emerging mechanisms of the angiogenic switch during tumorigenesis. Cell 86, 353-364.
3. Boehm, T., Folkman, J., Browder, T., and Oreilly, M. S. (1997) Antiangiogenic therapy of experimental cancer does not induce acquired drug resistance. Nature 390, 404-407.
4. Bergers, G., Javaherian, K., Lo, K. M., Folkman, J., and Hanahan, D. (1999) Effects of angiogenesis inhibitors on multistage carcinogenesis in mice. Science 284, 808-812.
5. Zetter, B. R. (1998) Angiogenesis and tumor metastasis. Annu. Rev. Med. 49:407-424.
6. Weidner, N. (1998) Tumoural vascularity as a prognostic factor in cancer patients: The evidence continues to grow. J. Pathol. 184, 119-122.
7. Degani, H., Gusis, V., Weinstein, D., Fields, S., and Strano, S. (1997) Mapping pathophysiological features of breast tumors by MRI at high spatial resolution. Nature Med. 3, 780-782.
8. Guidi, A. J., Schnitt, S. J., Fischer, L., Tognazzi, K., Harris, J. R., Dvorak, H. F., and Brown, L. F. (1997) Vascular permeability factor (vascular endothelial growth factor) expression and angiogenesis in patients with ductal carcinoma in situ of the breast. Cancer 80, 1945-1953.
9. Balsari, A., Maier, J. A. M., Colnaghi, M. I., and Menard, S. (1999) Correlation between tumor vascularity, vascular endothelial growth factor production by tumor cells, serum vascular endothelial growth factor levels, and serum angiogenic activity in patients with breast carcinoma. Lab. Invest. 79, 897-902.
10. Klauber, N., Parangi, S., Flynn, E., Hamel, E., and D'Amato, R. J. (1997) Inhibition of angiogenesis and breast cancer in mice by the microtubule inhibitors 2-methoxyestradiol and taxol. Cancer Res. 57, 81-86.
11. Harris, A. L., Zhang, H. T., Moghaddam, A., Fox, S., Scott, P., Pattison, A., Gatter, K., Stratford, I., and Bicknell, R. (1996) Breast cancer angiogenesis—New approaches to 12. Weinstatsaslow, D. L., Zabrenetzky, V. S., Vanhoutte, K., Frazier, W. A., Roberts, D. D., and Steeg, P. S. (1994) Transfection of thrombospondin 1 complementary DNA into a human breast carcinoma cell line reduces primary tumor growth, metastatic potential, and angiogenesis. Cancer Res. 54, 6504-6511.
13. Neufeld, G., Cohen, T., Gengrinovitch, S., and Poltorak, Z. (1999) Vascular endothelial growth factor (VEGF) and its receptors. FASEB J. 13, 9-22.
14. Brooks, P. C., Montgomery, A. M. P., Rosenfeld, M., Reisfeld, R. A., Hu, T. H., Klier, G., and Cheresh, D. A. (1994) Integrin alpha(v)beta(3) antagonists promote tumor regression by inducing apoptosis of angiogenic blood vessels. Cell 79, 1157-1164.
15. Brooks, P. C., Silletti, S., Von Schalscha, T. L., Friedlander, M., and Cheresh, D. A. (1998) Disruption of angiogenesis by PEX, a noncatalytic metalloproteinase fragment with integrin binding activity. Cell 92, 391-400.
16. O'Reilly, M. S., Boehm, T., Shing, Y., Fukai, N., Vasios, G., Lane, W. S., Flynn, E., Birkhead, J. R., Olsen, B. R., and Folkman, J. (1997) Endostatin: an endogenous inhibitor of angiogenesis and tumor growth. Cell 88, 277-285.
17. Oreilly, M. S., Holmgren, L., Chen, C., and Folkman, J. (1996) Angiostatin induces and sustains dormancy of human primary tumors in mice. Nature Med. 2, 689-692.
18. Tanaka, T., Manome, Y., Wen, P., Kufe, D. W., and Fine, H. A. (1997) Viral vector-mediated transduction of a modified platelet factor 4 cDNA inhibits angiogenesis and tumor growth. Nature Med. 3, 437-442.
19. Maione, T. E., Gray, G. S., Petro, J., Hunt, A. J., Donner, A. L., Bauer, S. I., Carson, H. F., and Sharpe, R. J. (1990) Inhibition of angiogenesis by recombinant human platelet factor-4 and related peptides. Science 247, 77-79.
20. Neufeld, G., Akiri, G., and Vadasz, Z. (2000) in Platelet Factor 4 (PF4). The Cytokine Reference: A compendium of cytokines and other mediators of host defence (Oppenheim, J. J. and Feldmann, M. eds) Academic Press.
21. Gengrinovitch, S., Greenberg, S. M., Cohen, T., Gitay-Goren, H., Rockwell, P., Maione, T. E., Levi, B., and Neufeld, G. (1995) Platelet factor-4 inhibits the mitogenic activity of VEGF-121 and VEGF-165 using several concurrent mechanisms. J. Biol. Chem. 270, 15059-15065.
22. Brown, K. J. and Parish, C. R. (1994) Histidine-rich glycoprotein and platelet factor 4 mask heparan sulfate proteoglycans recognized by acidic and basic fibroblast growth factor. Biochemistry 33, 13918-13927.
23. Gupta, S. K. and Singh, J. P. (1994) Inhibition of endothelial cell. Proliferation by platelet factor-4 involves a unique action on S phase progression. J. Cell Biol. 127, 1121-1127.
24. Watson, J. B., Getzler, S. B., and Mosher, D. F. (1994) Platelet factor 4 modulates the mitogenic activity of basic fibroblast growth factor. J. Clin. Invest. 94, 261-268.
25. Maione, T. E., Gray, G. S., Hunt, A. J., and Sharpe, R. J. (1991) Inhibition of tumor growth in mice by an analogue of platelet factor 4 that lacks affinity for heparin and retains potent angiostatic activity. Cancer Res. 51, 2077-2083.
26. Sharpe, R. J., Byers, H. R., Scott, C. F., Bauer, S. I., and Maione, T. E. (1990) Growth inhibition of murine melanoma and human colon carcinoma by recombinant human platelet factor 4. J. Natl. Cancer Inst. 82, 848-853.
27. Saito, H., Papaconstantinou, J., Sato, H., and Goldstein, S. (1997) Regulation of a novel gene encoding a lysyl oxidase-related protein in cellular adhesion and senescence. J. Biol. Chem. 272, 8157-8160.
28. Kim, Y., Boyd, C. D., and Csiszar, K. (1995) A new gene with sequence and structural similarity to the gene encoding human lysyl oxidase. J. Biol. Chem. 270, 7176-7182.
29. Kim, Y. H., Peyrol, S., So, C. K., Boyd, C. D., and Csiszar, K. (1999) Coexpression of the lysyl oxidase-like gene (LOXL) and the gene encoding type III procollagen in induced liver fibrosis. J. Cell Biochem. 72, 181-188.
30. Rabinovitz, M. (1999) Angiogenesis and its inhibition: the copper connection. J. Natl. Cancer Inst. 91, 1689-1690.
31. Jang, W., Hua, A., Spilson, S. V., Miller, W., Roe, B. A., and Meister, M. H. (1999) Comparative sequence of human and mouse BAC clones from the mnd2 region of chromosome 2p13. Genome Res. 9, 53-61.
32. Yoshida, D., Ikeda, Y., and Nakazawa, S. (1995) Copper chelation inhibits tumor angiogenesis in the experimental 9L gliosarcoma model. Neurosurgery 37, 287-292.
33. Borgstroem, P., Discipio, R., and Maione, T. E. (1998) Recombinant platelet factor 4, an angiogenic marker for human breast carcinoma. Anticancer Res. 18, 4035-4041.
34. Shweiki, D., Neeman, M., Itin, A., and Keshet, E. (1995) Induction of vascular endothelial growth factor expression by hypoxia and by glucose deficiency in multicell spheroids: Implications for tumor angiogenesis. Proc. Natl. Acad. Sci. USA 92, 768-772.
35. Rak, J., Mitsuhashi, Y., Bayko, L., Filmus, J., Shirasawa, S., Sasazuki, T., and Kerbel, R. S. (1995) Mutant ras oncogenes upregulate VEGF/VPF expression: Implications for induction and inhibition of tumor angiogenesis. Cancer Res. 55, 4575-4580.
36. Koch, A. E. (1998) Angiogenesis—Implications for rheumatoid arthritis. Arthritis Rheum. 41, 951-962.
37. Paleolog, E. M. and Fava, R. A. (1998) Angiogenesis in rheumatoid arthritis: implications for future therapeutic strategies. Springer Semin. Immunopathol. 20, 73-94.
38. Miller, J. W., Adamis, A. P., and Aiello, L. P. (1997) Vascular endothelial growth factor in ocular neovascularization and proliferative diabetic retinopathy. Diabetes Metab. Rev. 13, 37-50.
39. Detmar, M., Brown, L. F., Claffey, K. P., Yee, K. T., Kocher, O., Jackman, R. W., Berse, B., and Dvorak, H. F. (1994) Overexpression of vascular permeability factor/vascular endothelial growth factor and its receptors in psoriasis. J. Exp. Med. 180, 1141-1146.
40. Creamer, D., Allen, M. H., Sousa, A., Poston, R., and Barker, J. N. W. N. (1997) Localization of endothelial proliferation and microvascular expansion in active plaque psoriasis. Br. J. Dermatol. 136, 859-865.
41. Lie, J. T. (1992) Vasculitis simulators and vasculitis look-alikes. Curr. Opin. Rheumatol. 4, 47-55.
42. Klipple, G. L. and Riordan, K. K. (1989) Rare inflammatory and hereditary connective tissue diseases. Rheum. Dis. Clin. North Am. 15, 383-398.
43. Brahn, E., Lehman, T. J. A., Peacock, D. J., Tang, C., and Banquerigo, M. L. (1999) Suppression of coronary vasculitis in a murine model of Kawasaki disease using an angiogenesis inhibitor. Clin. Immunol. Immunopathol. 90, 147-151.
44. Cid, M. C., Grant, D. S., Hoffman, G. S., Auerbach, R., Fauci, A. S., and Kleinman, H. K. (1993) Identification of Haptoglobin as an Angiogenic Factor in Sera from Patients with Systemic Vasculitis. J. Clin. Invest. 91, 977-985.
45. Hoffman, G. S., Filie, J. D., Schumacher, H. R., Jr., Ortiz-Bravo, E., Tsokos, M. G., Marini, J. C., Kerr, G. S., Ling, Q. H., and Trentham, D. E. (1991) Intractable vasculitis, resorptive osteolysis, and immunity to type I collagen in type VIII Ehlers-Danlos syndrome. Arthritis Rheum. 34, 1466-1475.

46. Bauters, C. and Isner, J. M. (1997) The biology of restenosis. Prog. Cardiovasc. Dis. 40, 107-116.
47. Begelman, S. M. and Olin, J. W. (2000) Fibromuscular dysplasia. Curr. Opin. Rheumatol. 12, 41-47.
48. Palta, S., Pai, A. M., Gill, K. S., and Pai, R. G. (2000) New insights into the progression of aortic stenosis: implications for secondary prevention. Circulation 101, 2497-2502.
49. Wilchek, M. Miron, T., 1982 Immobilization of enzymes and affinity ligands onto agarose via stable and uncharged carbamate linkages. Biochem. Int. 4, 629-635.
50. Soker, S., Takashima, S., Miao, H. Q., Neufeld, G., Klagsbrun, M., 1998. Neuropilin-1 is expressed by endothelial and tumor cells as an isoform specific receptor for vascular endothelial growth factor. Cell 92, 735-745.
51. Zhang, H. T., Craft, P., Scott, P. A. E., Ziche, M., Weich, H. A., Harris, A. L., Bicknell, R., 1995. Enhancement of tumor growth and vascular density by transfection of vascular endothelial cell growth factor into MCF-7 human breast carcinoma cells. J. Nat. Cancer Inst. 87, 213-219.
52. Cohen, T., Gluzman-Poltorak, Z., Brodzky, A., Meytal, V., Sabo, E., Misselevich, I., Hassoun, M., Boss, J. H., Resnick, M., Shneyvas, D., Eldar, S., Neufeld, G., 2001. Neuroendocrine Cells along the Digestive Tract Express Neuropilin-2. Biochem. Biophys. Res. Commun. 284, 395-403.
53. Mcleskey, S. W., Kurebayashi, J., Honig, S. F., Zwiebel, J., Lippman, M. E., Dickson, R. B., Kern, F. G., 1993. Fibroblast Growth Factor-4 Transfection of MCF-7 Cells Produces Cell Lines That Are Tumorigenic and Metastatic in Ovariectomized or Tamoxifen-Treated Athymic Nude Mice. Cancer Res. 53, 2168-2177.
54. Nakamura et al. Cancer Res 60(3), 760-5, 2000.
55. Szczylik et al (1991) Selective inhibition of leukemia cell proliferation by BCR-ABL antisense oligodeoxynucleotides. Science 253:562.
56. Calabretta et al. (1991) Normal and leukemic hematopoietic cell manifest differential sensitivity to inhibitory effects of c-myc antisense oligodeoxynucleotides: an in vitro study relevant to bone marrow purging. Proc. Natl. Acad. Sci. USA 88:2351.
57. Heikhila et al. (1987) A c-myc antisense oligodeoxynucleotide inhibits entry into S phase but not progress from G(0) to G(1). Nature, 328:445.
58. Burch and Mahan (1991) Oligodeoxynucleotides antisense to the interleukin I receptor m RNA block the effects of interleukin I in cultured murine and human fibroblasts and in mice. J. Clin. Invest. 88:1190.
59. Welch P. J., Barber J. R., and Wong-Staal F. (1998) Expression of ribozymes in gene transfer systems to modulate target RNA levels. Curr. Opin. Biotechnol., 9(5):486-496.
60. Bedell-Hogan, D., Trackman, P., Abrams, W., Rosenbloom, J., and Kagan, H. (1993) Oxidation, cross-linking, and insolubilization of recombinant tropoelastin by purified lysyl oxidase. J. Biol. Chem. 268, 10345-10350).
61. Colpaert, C., Vermeulen, P., Van Marck, E., and Dirix, L. (2001) The presence of a fibrotic focus is an independent predictor of early metastasis in lymph node-negative breast cancer patients. Am. J. Surg. Pathol. 25, 1557 Hasebe, T., Mukai, K., Tsuda, H., and Ochiai, A. (2000) New prognostic histological parameter of invasive ductal carcinoma of the breast: Clinicopathological significance of fibrotic focus. Pathology International 50, 263-272
62. Nishimura, R., Hasebe, T., Tsubono, Y., Ono, M., Sugitoh, M., Arai, T., and Mukai, K. (1998) The fibrotic focus in advanced colorectal carcinoma: a hitherto unrecognized histological predictor for liver metastasis. Virchows Arch. 433, 517-522
63. Ellenrieder, V., Alber, B., Lacher, U., Hendler, S. F., Menke, A., Boeck, W., Wagner, M., Wilda, M., Friess, H., Buchler, M., Adler, G., and Gress, T. M. (2000) Role of MT-MMPs and MMP-2 in pancreatic cancer progression. Int. J. Cancer 85, 14-20
64. Stamenkovic, I. (2000) Matrix metalloproteinases in tumor invasion and metastasis. Semin. Cancer Biol. 10, 415-433
65. Duffy, M. J., Maguire, T. M., Hill, A., McDermott, E., and O'Higgins, N. (2000) Metalloproteinases: role in breast carcinogenesis, invasion and metastasis. Breast Cancer Res. 2, 252-257
66. Vlodaysky, I. and Friedmann, Y. (2001) Molecular properties and involvement of heparanase in cancer metastasis and angiogenesis. J. Clin. Invest 108, 341-347
67. Schuppan, D., Ruehl, M., Somasundaram, R., and Hahn, E. G. (2001) Matrix as a modulator of hepatic fibrogenesis. Semin Liver Dis. 21, 351-372
68. Sawada, S., Murakami, K., Murata, J., Tsukada, K., and Saiki, I. (2001) Accumulation of extracellular matrix in the liver induces high metastatic potential of hepatocellular carcinoma to the lung. Int. J. Oncol. 19, 65-70
69. Fire, A., Xu, S., Montgomery, M. K., Kostas, S. A., Driver, S. E., and Mello, C. C. (1998) Potent and specific genetic interference by double-stranded RNA in *Caenorhabditis elegans*. Nature 391, 806-811.
70. Zamore, P. D., Tuschl, T., Sharp, P. A., and Bartel, D. P. (2000) RNAi: double-stranded RNA directs the ATP-dependent cleavage of mRNA at 21 to 23 nucleotide intervals. Cell 101, 25-33.
71. Elbashir, S. M., Lendeckel, W. and Tuschl, T. (2001) RNA interference is mediated by 21- and 22-nucleotide RNAs. Genes Dev. 15, 188-200.
72. Hammond, S. M., Bernstein, E., Beach, D. and Hannon, G. J. (2000) An RNA-directed nuclease mediates post-transcriptional gene silencing in Drosophila cells. Nature 404, 293-296.
73. Bernstein, E., Caudy, A. A., Hammond, S. M. and Hannon, G. J. (2001) Role for a bidentate ribonuclease in the initiation step of RNA interference. Nature 409, 363-366.
74. Nykanen, A., Haley, B. and Zamore, P. D. (2001) ATP requirements and small interfering RNA structure in the RNA interference pathway. Cell 107, 309-321
75. Caplen, N. J., Fleenor, J., Fire, A. and Morgan, R. A. (2000). dsRNA-mediated gene silencing in cultured Drosophila cells: a tissue culture model for the analysis of RNA interference. Gene 252, 95-105.
76. Ui-Tei, K., Zenno, S., Miyata, Y. and Saigo, K. (2000) Sensitive assay of RNA interference in Drosophila and Chinese hamster cultured cells using firefly luciferase gene as target. FEBS Lett. 479, 79-82.
77. Hohjoh, H. (2002) RNA interference (RNA(i)) induction with various types of synthetic oligonucleotide duplexes in cultured human cells. FEBS Lett. 521, 195-9.
78. Leirdal, M., and Sioud, M. (2002) Gene silencing in mammalian cells by preformed small RNA duplexes. Biochem Biophys Res Commun 295, 744-8.
79. Yang, D., Buchholz, F., Huang, Z., Goga, A., Chen, C. Y., Brodsky, F. M., and Bishop, J. M. (2002) Short RNA duplexes produced by hydrolysis with Escherichia coli RNase III mediate effective RNA interference in mammalian cells. Proc. Natl. Acad. Sci. U.S.A. 99, 9942-7.
80. Pinder, S. E., Ellis, I. O., Galea, M., O'Rouke, S., Blamey, R. W., and Elston, C. W. (1994) Pathological prognostic factors in breast cancer. III. Vascular invasion: relationship with recurrence and survival in a large study with long-term follow-up. Histopathology 24, 41-47

81. Luna, L. G. (1968) Manual of histologic staining methods of the armed forces institute of pathology, McGraw-Hill, New-York.

What is claimed:

1. A method of inhibiting angiogenesis in a subject, comprising:
    administering to the subject a polynucleotide of at least 15 bases that specifically hybridizes under physiological conditions to a nucleic acid having the nucleotide sequence of SEQ ID NO:1,
    thereby inhibiting angiogenesis in the subject.

2. The method of claim 1, wherein the angiogenesis in the subject is involved in tumor growth, invasiveness, or metastasis.

3. The method of claim 1, wherein the polynucleotide is administered locally.

4. The method of claim 1, wherein the polynucleotide is administered systemically.

5. The method of claim 1, wherein the subject has a breast tumor.

6. The method of claim 1, wherein the subject has a metastasis of a breast tumor.

7. The method of claim 1, wherein the subject has a colon tumor.

8. The method of claim 1, wherein the subject has a metastasis of a colon tumor.

9. The method of claim 1, wherein the polynucleotide comprises between 15 and 20 bases.

10. The method of claim 1, wherein the polynucleotide comprises between 15 and 40 bases.

11. A method of inhibiting angiogenesis in a subject, comprising:
    administering to the subject an antisense polynucleotide of at least 15 bases capable of hybridizing under physiological conditions to an mRNA encoding a polypeptide comprising the amino acid sequence set forth in SEQ ID NO: 2, thereby inhibiting angiogenesis in the subject.

12. The method of claim 11, wherein the polynucleotide is complementary to a nucleic acid having the nucleotide sequence of SEQ ID NO: 1.

13. The method of claim 11, wherein the subject has a breast tumor.

14. The method of claim 11, wherein the subject has a colon tumor.

15. A method of inhibiting angiogenesis in a subject, comprising:
    administering to the subject a polynucleotide of at least 15 bases that is complementary to a nucleic acid having the nucleotide sequence of SEQ ID NO: 1,
    thereby inhibiting angiogenesis in the subject.

16. The method of claim 15, wherein the subject has a breast tumor.

17. The method of claim 15, wherein the subject has a colon tumor.

18. The method of claim 15, wherein the polynucleotide comprises between 15 and 20 bases.

19. The method of claim 15, wherein the polynucleotide comprises between 15 and 40 bases.

* * * * *

UNITED STATES PATENT AND TRADEMARK OFFICE
CERTIFICATE OF CORRECTION

PATENT NO. : 8,815,823 B2  
APPLICATION NO. : 13/416976  
DATED : August 26, 2014  
INVENTOR(S) : Gera Neufeld Page 1 of 1

It is certified that error appears in the above-identified patent and that said Letters Patent is hereby corrected as shown below:

On the Title Page, item (62) add --, which is a CIP of application No. 10/305,348, filed on Nov. 27, 2002, now abandoned-- after Pat. No. 8,163,494.

Signed and Sealed this  
Third Day of March, 2015

Michelle K. Lee  
*Deputy Director of the United States Patent and Trademark Office*

SEQUENCE LISTING

<160> NUMBER OF SEQ ID NOS: 19

<210> SEQ ID NO 1
<211> LENGTH: 2325
<212> TYPE: DNA
<213> ORGANISM: Homo sapiens

<400> SEQUENCE: 1

```
atggagaggc ctctgtgctc ccacctctgc agctgcctgg ctatgctggc cctcctgtcc      60
cccctgagcc tggcacagta tgacagctgg ccccattacc ccgagtactt ccagcaaccg     120
gctcctgagt atcaccagcc ccaggccccc gccaacgtgg ccaagattca gctgcgcctg     180
gctgggcaga agaggaagca cagcgagggc cgggtggagg tgtactatga tggccagtgg     240
ggcaccgtgt gcgatgacga cttctccatc cacgctgccc acgtcgtctg ccgggagctg     300
ggctatgtgg aggccaagtc ctggactgcc agctcctcct acggcaaggg agaagggccc     360
atctggttag acaatctcca ctgtactggc aacgaggcga cccttgcagc atgcacctcc     420
aatggctggg gcgtcactga ctgcaagcac acggaggatg tcggtgtggt gtgcagcgac     480
aaaaggattc ctgggttcaa atttgacaat tcgttgatca accagataga gaacctgaat     540
atccaggtgg aggacattcg gattcgagcc atcctctcaa cctaccgcaa gcgcaccca      600
gtgatggagg gctacgtgga ggtgaaggag gcaagacct ggaagcagat ctgtgacaag      660
cactggacgg ccaagaattc ccgcgtggtc tgcggcatgt ttggcttccc tggggagagg     720
acatacaata ccaaagtgta caaatgtttt gcctcacgga ggaagcagcg ctactggcca     780
ttctccatgg actgcaccgg cacagaggcc cacatctcca gctgcaagct gggcccccag     840
gtgtcactgg accccatgaa gaatgtcacc tgcgagaatg gctaccggc cgtggtgggt      900
tgtgtgcctg ggcaggtctt cagccctgac ggaccctcaa gattccggaa agcgtacaag     960
ccagagcaac ccctggtgcg actgagaggc ggtgcctaca tcggggaggg ccgcgtggag    1020
gtgctcaaaa atggagaatg ggggaccgtc tgcgacgaca gtgggacct ggtgtcggcc     1080
agtgtggtct gcagagagct gggctttggg agtgccaaag aggcagtcac tggctcccga    1140
ctggggcaag ggatcggacc catccacctc aacgagatcc agtgcacagg caatgagaag    1200
tccattatag actgcaagtt caatgccgag tctcagggct gcaaccacga ggaggatgct    1260
ggtgtgagat gcaacacccc tgccatgggc ttgcagaaga gctgcgcct gaacggcggc     1320
cgcaatccct acgagggccg agtggaggtg ctggtggaga gaaacgggtc ccttgtgtgg    1380
gggatggtgt gtggccaaaa ctggggcatc gtggaggcca tggtggtctg ccgccagctg    1440
ggcctgggat tcgccagcaa cgccttccag gagacctggt attggacgg agatgtcaac     1500
agcaacaaag tggtcatgag tggagtgaag tgctcgggaa cggagctgtc cctggcgcac    1560
tgccgccacg acggggagga cgtggcctgc ccccagggcg gagtgcagta cggggccgga    1620
gttgcctgct cagaaaccgc ccctgacctg gtcctcaatg cggagatggt gcagcagacc    1680
acctacctgg aggaccggcc catgttcatg ctgcagtgtg ccatggagga gactgcctc     1740
tcggcctcag ccgcgcagac cgaccccacc acgggctacc gccggctcct gcgcttctcc    1800
tcccagatcc acaacaatgg ccagtccgac ttccggccca gaacggccg ccacgcgtgg    1860
atctggcacg actgtcacag gcactaccac agcatggagg tgttcaccca ctatgacctg    1920
```

-continued

```
ctgaacctca atggcaccaa ggtggcagag ggccacaagg ccagcttctg cttggaggac    1980
acagaatgtg aaggagacat ccagaagaat tacgagtgtg ccaacttcgg cgatcagggc    2040
atcaccatgg gctgctggga catgtaccgc catgacatcg actgccagtg ggttgacatc    2100
actgacgtgc ccctggaga ctacctgttc caggttgtta ttaacccaa cttcgaggtt     2160 gcagaatccg attactccaa caacatcatg aaatgcagga gccgctatga cggccaccgc    2220
atctggatgt acaactgcca cataggtggt tccttcagcg aagagacgga aaaaaagttt    2280
gagcacttca gcgggctctt aaacaaccag ctgtccccgc agtaa                    2325
```

```
<210> SEQ ID NO 2
<211> LENGTH: 774
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Glu | Arg | Pro | Leu | Cys | Ser | His | Leu | Cys | Ser | Cys | Leu | Ala | Met | Leu |
| 1 | | | | 5 | | | | | 10 | | | | | 15 | |
| Ala | Leu | Leu | Ser | Pro | Leu | Ser | Leu | Ala | Gln | Tyr | Asp | Ser | Trp | Pro | His |
| | | | 20 | | | | | 25 | | | | | 30 | | |
| Tyr | Pro | Glu | Tyr | Phe | Gln | Gln | Pro | Ala | Pro | Glu | Tyr | His | Gln | Pro | Gln |
| | | 35 | | | | | 40 | | | | | 45 | | | |
| Ala | Pro | Ala | Asn | Val | Ala | Lys | Ile | Gln | Leu | Arg | Leu | Ala | Gly | Gln | Lys |
| | 50 | | | | | 55 | | | | | 60 | | | | |
| Arg | Lys | His | Ser | Glu | Gly | Arg | Val | Glu | Val | Tyr | Tyr | Asp | Gly | Gln | Trp |
| 65 | | | | | 70 | | | | | 75 | | | | | 80 |
| Gly | Thr | Val | Cys | Asp | Asp | Asp | Phe | Ser | Ile | His | Ala | Ala | His | Val | Val |
| | | | | 85 | | | | | 90 | | | | | 95 | |
| Cys | Arg | Glu | Leu | Gly | Tyr | Val | Glu | Ala | Lys | Ser | Trp | Thr | Ala | Ser | Ser |
| | | | 100 | | | | | 105 | | | | | 110 | | |
| Ser | Tyr | Gly | Lys | Gly | Glu | Gly | Pro | Ile | Trp | Leu | Asp | Asn | Leu | His | Cys |
| | | 115 | | | | | 120 | | | | | 125 | | | |
| Thr | Gly | Asn | Glu | Ala | Thr | Leu | Ala | Ala | Cys | Thr | Ser | Asn | Gly | Trp | Gly |
| | 130 | | | | | 135 | | | | | 140 | | | | |
| Val | Thr | Asp | Cys | Lys | His | Thr | Glu | Asp | Val | Gly | Val | Val | Cys | Ser | Asp |
| 145 | | | | | 150 | | | | | 155 | | | | | 160 |
| Lys | Arg | Ile | Pro | Gly | Phe | Lys | Phe | Asp | Asn | Ser | Leu | Ile | Asn | Gln | Ile |
| | | | | 165 | | | | | 170 | | | | | 175 | |
| Glu | Asn | Leu | Asn | Ile | Gln | Val | Glu | Asp | Ile | Arg | Ile | Arg | Ala | Ile | Leu |
| | | | 180 | | | | | 185 | | | | | 190 | | |
| Ser | Thr | Tyr | Arg | Lys | Arg | Thr | Pro | Val | Met | Glu | Gly | Tyr | Val | Glu | Val |
| | | 195 | | | | | 200 | | | | | 205 | | | |
| Lys | Glu | Gly | Lys | Thr | Trp | Lys | Gln | Ile | Cys | Asp | Lys | His | Trp | Thr | Ala |
| | 210 | | | | | 215 | | | | | 220 | | | | |
| Lys | Asn | Ser | Arg | Val | Val | Cys | Gly | Met | Phe | Gly | Phe | Pro | Gly | Glu | Arg |
| 225 | | | | | 230 | | | | | 235 | | | | | 240 |
| Thr | Tyr | Asn | Thr | Lys | Val | Tyr | Lys | Met | Phe | Ala | Ser | Arg | Arg | Lys | Gln |
| | | | | 245 | | | | | 250 | | | | | 255 | |
| Arg | Tyr | Trp | Pro | Phe | Ser | Met | Asp | Cys | Thr | Gly | Thr | Glu | Ala | His | Ile |
| | | | 260 | | | | | 265 | | | | | 270 | | |
| Ser | Ser | Cys | Lys | Leu | Gly | Pro | Gln | Val | Ser | Leu | Asp | Pro | Met | Lys | Asn |
| | | 275 | | | | | 280 | | | | | 285 | | | |
| Val | Thr | Cys | Glu | Asn | Gly | Leu | Pro | Ala | Val | Val | Gly | Cys | Val | Pro | Gly |
| | 290 | | | | | 295 | | | | | 300 | | | | |

-continued

Gln Val Phe Ser Pro Asp Gly Pro Ser Arg Phe Arg Lys Ala Tyr Lys
305                 310                 315                 320

Pro Glu Gln Pro Leu Val Arg Leu Arg Gly Ala Tyr Ile Gly Glu
            325                 330                 335

Gly Arg Val Glu Val Leu Lys Asn Gly Glu Trp Gly Thr Val Cys Asp
            340                 345                 350

Asp Lys Trp Asp Leu Val Ser Ala Ser Val Val Cys Arg Glu Leu Gly
            355                 360                 365

Phe Gly Ser Ala Lys Glu Ala Val Thr Gly Ser Arg Leu Gly Gln Gly
370                 375                 380

Ile Gly Pro Ile His Leu Asn Glu Ile Gln Cys Thr Gly Asn Glu Lys
385                 390                 395                 400

Ser Ile Ile Asp Cys Lys Phe Asn Ala Glu Ser Gln Gly Cys Asn His
                405                 410                 415

Glu Glu Asp Ala Gly Val Arg Cys Asn Thr Pro Ala Met Gly Leu Gln
            420                 425                 430

Lys Lys Leu Arg Leu Asn Gly Gly Arg Asn Pro Tyr Glu Gly Arg Val
            435                 440                 445

Glu Val Leu Val Glu Arg Asn Gly Ser Leu Val Trp Gly Met Val Cys
450                 455                 460

Gly Gln Asn Trp Gly Ile Val Glu Ala Met Val Val Cys Arg Gln Leu
465                 470                 475                 480

Gly Leu Gly Phe Ala Ser Asn Ala Phe Gln Glu Thr Trp Tyr Trp His
                485                 490                 495

Gly Asp Val Asn Ser Asn Lys Val Val Met Ser Gly Val Lys Cys Ser
            500                 505                 510

Gly Thr Glu Leu Ser Leu Ala His Cys Arg His Asp Gly Glu Asp Val
            515                 520                 525

Ala Cys Pro Gln Gly Val Gln Tyr Gly Ala Gly Val Ala Cys Ser
530                 535                 540

Glu Thr Ala Pro Asp Leu Val Leu Asn Ala Glu Met Val Gln Gln Thr
545                 550                 555                 560

Thr Tyr Leu Glu Asp Arg Pro Met Phe Met Leu Gln Cys Ala Met Glu
                565                 570                 575

Glu Asn Cys Leu Ser Ala Ser Ala Gln Thr Asp Pro Thr Thr Gly
            580                 585                 590

Tyr Arg Arg Leu Leu Arg Phe Ser Gln Ile His Asn Asn Gly Gln
            595                 600                 605

Ser Asp Phe Arg Pro Lys Asn Gly Arg His Ala Trp Ile Trp His Asp
610                 615                 620

Cys His Arg His Tyr His Ser Met Glu Val Phe Thr His Tyr Asp Leu
625                 630                 635                 640

Leu Asn Leu Asn Gly Thr Lys Val Ala Glu Gly His Lys Ala Ser Phe
                645                 650                 655

Cys Leu Glu Asp Thr Glu Cys Glu Gly Asp Ile Gln Lys Asn Tyr Glu
            660                 665                 670

Cys Ala Asn Phe Gly Asp Gln Gly Ile Thr Met Gly Cys Trp Asp Met
            675                 680                 685

Tyr Arg His Asp Ile Asp Cys Gln Trp Val Asp Ile Thr Asp Val Pro
            690                 695                 700

Pro Gly Asp Tyr Leu Phe Gln Val Val Ile Asn Pro Asn Phe Glu Val
705                 710                 715                 720

Ala Glu Ser Asp Tyr Ser Asn Asn Ile Met Lys Cys Arg Ser Arg Tyr

```
                            725                 730                 735
Asp Gly His Arg Ile Trp Met Tyr Asn Cys His Ile Gly Gly Ser Phe
                740                 745                 750

Ser Glu Glu Thr Glu Lys Lys Phe Glu His Phe Ser Gly Leu Leu Asn
                755                 760                 765

Asn Gln Leu Ser Pro Gln
        770

<210> SEQ ID NO 3
<211> LENGTH: 757
<212> TYPE: PRT
<213> ORGANISM: Homo sapiens

<400> SEQUENCE: 3

Met Met Trp Pro Gln Pro Pro Thr Phe Ser Leu Phe Leu Leu Leu Leu
1               5                   10                  15

Leu Ser Gln Ala Pro Ser Ser Arg Pro Gln Ser Ser Gly Thr Lys Lys
                20                  25                  30

Leu Arg Leu Val Gly Pro Ala Asp Arg Pro Glu Glu Gly Arg Leu Glu
            35                  40                  45

Val Leu His Gln Gly Gln Trp Gly Thr Val Cys Asp Asp Asp Phe Ala
    50                  55                  60

Leu Gln Glu Ala Thr Val Ala Cys Arg Gln Leu Gly Phe Glu Ser Ala
65                  70                  75                  80

Leu Thr Trp Ala His Ser Ala Lys Tyr Gly Gln Gly Glu Gly Pro Ile
                85                  90                  95

Trp Leu Asp Asn Val Arg Cys Leu Gly Thr Glu Lys Thr Leu Asp Gln
                100                 105                 110

Cys Gly Ser Asn Gly Trp Gly Ile Ser Asp Cys Arg His Ser Glu Asp
            115                 120                 125

Val Gly Val Val Cys His Pro Arg Arg Gln His Gly Tyr His Ser Glu
    130                 135                 140

Lys Val Ser Asn Ala Leu Gly Pro Gln Gly Arg Arg Leu Glu Glu Val
145                 150                 155                 160

Arg Leu Lys Pro Ile Leu Ala Ser Ala Lys Arg His Ser Pro Val Thr
                165                 170                 175

Glu Gly Ala Val Glu Val Arg Tyr Asp Gly His Trp Arg Gln Val Cys
            180                 185                 190

Asp Gln Gly Trp Thr Met Asn Asn Ser Arg Val Val Cys Gly Met Leu
    195                 200                 205

Gly Phe Pro Ser Gln Thr Ser Val Asn Ser His Tyr Tyr Arg Lys Val
    210                 215                 220

Trp Asn Leu Lys Met Lys Asp Pro Lys Ser Arg Leu Asn Ser Leu Thr
225                 230                 235                 240

Lys Lys Asn Ser Phe Trp Ile His Arg Val Asp Cys Phe Gly Thr Glu
                245                 250                 255

Pro His Leu Ala Lys Cys Gln Val Gln Val Ala Pro Gly Arg Gly Lys
            260                 265                 270

Leu Arg Pro Ala Cys Pro Gly Gly Met His Ala Val Val Ser Cys Val
    275                 280                 285

Ala Gly Pro His Phe Arg Arg Gln Lys Pro Lys Pro Thr Arg Lys Glu
    290                 295                 300

Ser His Ala Glu Glu Leu Lys Val Arg Leu Arg Ser Gly Ala Gln Val
305                 310                 315                 320
```

```
Gly Glu Gly Arg Val Glu Val Leu Met Asn Arg Gln Trp Gly Thr Val
            325                 330                 335
Cys Asp His Arg Trp Asn Leu Ile Ser Ala Ser Val Val Cys Arg Gln
            340                 345                 350
Leu Gly Phe Gly Ser Ala Arg Glu Ala Leu Phe Gly Ala Gln Leu Gly
            355                 360                 365
Gln Gly Leu Gly Pro Ile His Leu Ser Glu Val Arg Cys Arg Gly Tyr
            370                 375                 380
Glu Arg Thr Leu Gly Asp Cys Leu Ala Leu Glu Gly Ser Gln Asn Gly
385                 390                 395                 400
Cys Gln His Ala Asn Asp Ala Ala Val Arg Cys Asn Ile Pro Asp Met
            405                 410                 415
Gly Phe Gln Asn Lys Val Arg Leu Ala Gly Gly Arg Asn Ser Glu Glu
            420                 425                 430
Gly Val Val Glu Val Gln Val Glu Val Asn Gly Gly Pro Arg Trp Gly
            435                 440                 445
Thr Val Cys Ser Asp His Trp Gly Leu Thr Glu Ala Met Val Thr Cys
            450                 455                 460
Arg Gln Leu Gly Leu Gly Phe Ala Asn Phe Ala Leu Lys Asp Thr Trp
465                 470                 475                 480
Tyr Trp Gln Gly Thr Pro Glu Ala Lys Glu Val Val Met Ser Gly Val
            485                 490                 495
Arg Cys Ser Gly Thr Glu Met Ala Leu Gln Gln Cys Gln Arg His Gly
            500                 505                 510
Pro Val His Cys Ser His Gly Pro Gly Arg Phe Ser Ala Gly Val Ala
            515                 520                 525
Cys Met Asn Ser Ala Pro Asp Leu Val Met Asn Ala Gln Leu Val Gln
            530                 535                 540
Glu Thr Ala Tyr Leu Glu Asp Arg Pro Leu Ser Met Leu Tyr Cys Ala
545                 550                 555                 560
His Glu Glu Asn Cys Leu Ser Lys Ser Ala Asp His Met Asp Trp Pro
            565                 570                 575
Tyr Gly Tyr Arg Arg Leu Leu Arg Phe Ser Ser Gln Ile Tyr Asn Leu
            580                 585                 590
Gly Arg Ala Asp Phe Arg Pro Lys Ala Gly Arg His Ser Trp Ile Trp
            595                 600                 605
His Gln Cys His Arg His Asn His Ser Ile Glu Val Phe Thr His Tyr
            610                 615                 620
Asp Leu Leu Thr Leu Asn Gly Ser Lys Val Ala Glu Gly His Lys Ala
625                 630                 635                 640
Ser Phe Cys Leu Glu Asp Thr Asn Cys Pro Ser Gly Val Gln Arg Arg
            645                 650                 655
Tyr Ala Cys Ala Asn Phe Gly Glu Gln Gly Val Ala Val Gly Cys Trp
            660                 665                 670
Asp Thr Tyr Arg His Asp Ile Asp Cys Gln Trp Val Asp Ile Thr Asp
            675                 680                 685
Val Gly Pro Gly Asp Tyr Ile Phe Gln Val Val Val Asn Pro Thr Asn
            690                 695                 700
Asp Val Ala Glu Ser Asp Phe Ser Asn Asn Met Ile Arg Cys Arg Cys
705                 710                 715                 720
Lys Tyr Asp Gly Gln Arg Val Trp Leu His Asn Cys His Thr Gly Asp
            725                 730                 735
Ser Tyr Arg Ala Asn Ala Glu Leu Ser Leu Glu Gln Glu Gln Arg Leu
```

```
                740               745               750
Arg Asn Asn Leu Ile
        755

<210> SEQ ID NO 4
<211> LENGTH: 2262
<212> TYPE: DNA
<213> ORGANISM: Homo sapiens

<400> SEQUENCE: 4
atgcgacctg tcagtgtctg gcagtggagc ccctgggggc tgctgctgtg cctgctgtgc      60
agttcgtgct tggggtctcc gtccccttcc acgggccctg agaagaaggc cgggagccag     120
gggcttcggt tccggctggc tggcttcccc aggaagccct acgagggccg cgtggagata     180
cagcgagctg gtgaatgggg caccatctgc gatgatgact tcacgctgca ggctgcccac     240
atcctctgcc gggagctggg cttcacagag ccacaggct ggacccacag tgccaaatat      300
ggccctggaa caggccgcat ctggctgac aacttgagct gcagtgggac cgagcagagt      360
gtgactgaat gtgcctcccg ggctggggg aacagtgact gtacgcacga tgaggatgct      420
ggggtcatct gcaaagacca cgcctccct ggcttctcgg actccaatgt cattgaggta      480
gagcatcacc tgcaagtgga ggaggtgcga attcgacccg ccgttgggtg gggcagacga     540
cccctgcccg tgacgaggg gctggtggaa gtcaggcttc ctgacggctg gtcgcaagtg      600
tgcgacaaag ctggagcgc ccacaacagc cacgtggtct gcgggatgct gggcttcccc      660
agcgaaaaga gggtcaacgc ggccttctac aggctgctag cccaacggca gcaacactcc     720
tttggtctgc atggggtggc gtgcgtgggc acggaggccc acctctccct ctgttccctg     780
gagttctatc gtgccaatga caccgccagg tgccctgggg gggcccctgc agtggtgagc     840
tgtgtgccag gccctgtcta cgcggcatcc agtggccaga agaagcaaca acagtcgaag     900 cctcagggg aggcccgtgt ccgtctaaag gcggcgccc accctggaga gggccgggta     960
gaagtcctga aggccagcac atggggcaca gtctgtgacc gcaagtggga cctgcatgca    1020
gccagcgtgg tgtgtcggga gctgggcttc ggagtgctc gagaagctct gagtggcgct    1080 cgcatgggc agggcatggg tgctatccac ctgagtgaag ttcgctgctc tggacaggag    1140
ctctccctct ggaagtgccc ccacaagaac atcacagctg aggattgttc acatagccag    1200
gatgccgggg tccggtgcaa cctaccttac actggggcag agaccaggat ccgactcagt    1260
gggggccgca gccaacatga ggggcgagtc gaggtgcaaa taggggggacc tgggcccctt    1320 cgctgggggcc tcatctgtgg ggatgactgg gggaccctgg aggccatggt ggcctgtagg    1380
caactgggtc tgggctacgc caaccacggc ctgcaggaga cctggtactg ggactctggg    1440
aatataacag aggtggtgat gagtggagtg cgctgcacag gactgagct gtccctggat    1500 cagtgtgccc atcatggcac ccacatcacc tgcaagagga cagggacccg cttcactgct    1560
ggagtcatct gttctgagac tgcatcagat ctgttgctgc actcagcact ggtgcaggag    1620
accgcctaca tcgaagaccg gccctgcat atgttgtact gtgctgcgga agagaactgc    1680
ctggccagct cagcccgctc agccaactgg ccctatggtc accggcgtct gctccgattc    1740
tcctcccaga tccacaacct gggacagagc gacttcaggc caaggctgg cgccactcc    1800 tgggtgtgggc acgagtgcca tgggcattac acacagcatgg acatcttcac tcactatgat    1860
atcctcaccc caaatggcac caaggtggct gagggccaca agctagtttt ctgtctcgaa    1920
gacactgagt gtcaggagga tgtctccaag cggtatgagt gtgccaactt tggagagcaa    1980
```

```
ggcatcactg tgggttgctg ggatctctac cggcatgaca ttgactgtca gtggattgac    2040
atcacggatg tgaagccagg aaactacatt ctccaggttg tcatcaaccc aaactttgaa    2100
gtagcagaga gtgactttac caacaatgca atgaaatgta actgcaaata tgatggacat    2160
agaatctggg tgcacaactg ccacattggt gatgccttca gtgaagaggc aacaggagg     2220 tttgaacgct accctggcca gaccagcaac cagattatct aa                       2262

<210> SEQ ID NO 5
<211> LENGTH: 1725
<212> TYPE: DNA
<213> ORGANISM: Homo sapiens

<400> SEQUENCE: 5
atggctctgg cccgaggcag ccggcagctg ggggccctgg tgtggggcgc ctgcctgtgc      60
gtgctggtgc acgggcagca ggcgcagccc ggcagggct cggaccccgc ccgctggcgg     120
cagctgatcc agtgggagaa caacgggcag gtgtacagct tgctcaactc gggctcagag     180
tacgtgccgg ccggacctca gcgctccgag agtagctccc gggtgctgct ggccggcgcg     240
ccccaggccc agcagcggcg cagccacggg agccccggc gtcggcaggc gccgtccctg     300
cccctgccgg ggcgcgtggg ctcggacacc gtgcgcggcc aggcgcggca ccattcggc     360 tttggccagg tgcccgacaa ctggcgcgag gtggccgtcg gggacagcac gggcatggcc     420
ctggcccgca cctccgtctc ccagcaacgg cacgggggct ccgcctcctc ggtctcggct     480
tcggccttcg ccagcaccta ccgccagcag ccctcctacc gcagcagtt ccctacccg      540 caggcgccct tcgtcagcca gtacgagaac tacgaccccg cgtcgcggac ctacgaccag     600
ggtttcgtgt actaccggcc cgcgggcggc ggcgtgggcg cggggggcgg ggccgtggcc     660
tcggcggggg tcatctaccc ctaccagccc cgggcgcgct acgaggagta cggcggcggc     720
gaagagctgc ccgagtaccc gcctcagggc ttctacccgg cccccgagag gccctacgtg     780
ccgccgccgc cgccgccccc cgacggcctg accgccgct actcgcacag tctgtacagc     840
gagggcaccc ccggcttcga gcaggcctac cctgaccccg gtcccgaggc ggcgcaggcc     900
catggcggag acccacgcct gggctggtac ccgccctacg ccaacccgcc gcccgaggcg     960
tacgggccgc cgcgcgcgct ggagccgccc tacctgccgg tgcgcagctc cgacacgccc    1020
ccgccgggtg gggagcggaa cggcgcgcag cagggccgcc tcagcgtagg cagcgtgtac    1080
cggcccaacc agaacggccg cggtctccct gacttggtcc agaccccaa ctatgtgcaa    1140 gcatccactt atgtgcagag agccaccctg tactccctgc ctgtgctgc ggaggagaag    1200 tgtctggcca gcacagccta tgcccctgag gccaccgact acgatgtgcg ggtgctactg    1260
cgcttccccc agcgcgtgaa gaaccagggc acagcagact tcctcccaa ccggccacgg    1320 cacacctggg agtggcacag ctgccaccag cattaccaca gcatggacga gttcagccac    1380
tacgacctac tggatgcagc cacaggcaag aaggtggccg agggccacaa ggccagtttc    1440
tgcctggagg acagcacctg tgacttcggc aacctcaagc gctatgcatg cacctctcat    1500
acccagggcc tgagcccagg ctgctatgac acctacaatg cggacatcga ctgccagtgg    1560
atcgacataa ccgacgtgca gcctgggaac tacatcctca aggtgcacgt gaacccaaag    1620
tatattgttt tggagtctga cttcaccaac aacgtggtga gatgcaacat tcactacaca    1680
ggtcgctacg tttctgcaac aaactgcaaa attgtccaat cctga                    1725

<210> SEQ ID NO 6
<211> LENGTH: 574
```

<212> TYPE: PRT
<213> ORGANISM: Homo sapiens

<400> SEQUENCE: 6

```
Met Ala Leu Ala Arg Gly Ser Arg Gln Leu Gly Ala Leu Val Trp Gly
1               5                   10                  15

Ala Cys Leu Cys Val Leu Val His Gly Gln Gln Ala Gln Pro Gly Gln
                20                  25                  30

Gly Ser Asp Pro Ala Arg Trp Arg Gln Leu Ile Gln Trp Glu Asn Asn
        35                  40                  45

Gly Gln Val Tyr Ser Leu Leu Asn Ser Gly Ser Glu Tyr Val Pro Ala
    50                  55                  60

Gly Pro Gln Arg Ser Glu Ser Ser Arg Val Leu Leu Ala Gly Ala
65                  70                  75                  80

Pro Gln Ala Gln Gln Arg Ser His Gly Ser Pro Arg Arg Arg Gln
                85                  90                  95

Ala Pro Ser Leu Pro Leu Pro Gly Arg Val Gly Ser Asp Thr Val Arg
                100                 105                 110

Gly Gln Ala Arg His Pro Phe Gly Phe Gly Gln Val Pro Asp Asn Trp
            115                 120                 125

Arg Glu Val Ala Val Gly Asp Ser Thr Gly Met Ala Leu Ala Arg Thr
    130                 135                 140

Ser Val Ser Gln Gln Arg His Gly Gly Ser Ala Ser Ser Val Ser Ala
145                 150                 155                 160

Ser Ala Phe Ala Ser Thr Tyr Arg Gln Gln Pro Ser Tyr Pro Gln Gln
                165                 170                 175

Phe Pro Tyr Pro Gln Ala Pro Phe Val Ser Gln Tyr Glu Asn Tyr Asp
                180                 185                 190

Pro Ala Ser Arg Thr Tyr Asp Gln Gly Phe Val Tyr Tyr Arg Pro Ala
            195                 200                 205

Gly Gly Gly Val Gly Ala Gly Ala Ala Val Ala Ser Ala Gly Val
    210                 215                 220

Ile Tyr Pro Tyr Gln Pro Arg Ala Arg Tyr Glu Glu Tyr Gly Gly Gly
225                 230                 235                 240

Glu Glu Leu Pro Glu Tyr Pro Pro Gln Gly Phe Tyr Pro Ala Pro Glu
                245                 250                 255

Arg Pro Tyr Val Pro Pro Pro Pro Pro Asp Gly Leu Asp Arg
            260                 265                 270

Arg Tyr Ser His Ser Leu Tyr Ser Glu Gly Thr Pro Gly Phe Glu Gln
    275                 280                 285

Ala Tyr Pro Asp Pro Gly Pro Glu Ala Ala Gln Ala His Gly Gly Asp
290                 295                 300

Pro Arg Leu Gly Trp Tyr Pro Pro Tyr Ala Asn Pro Pro Glu Ala
305                 310                 315                 320

Tyr Gly Pro Pro Arg Ala Leu Glu Pro Pro Tyr Leu Pro Val Arg Ser
                325                 330                 335

Ser Asp Thr Pro Pro Gly Gly Glu Arg Asn Gly Ala Gln Gln Gly
            340                 345                 350

Arg Leu Ser Val Gly Ser Val Tyr Arg Pro Asn Gln Asn Gly Arg Gly
    355                 360                 365

Leu Pro Asp Leu Val Pro Asp Pro Asn Tyr Val Gln Ala Ser Thr Tyr
    370                 375                 380

Val Gln Arg Ala His Leu Tyr Ser Leu Arg Cys Ala Ala Glu Glu Lys
385                 390                 395                 400
```

```
Cys Leu Ala Ser Thr Ala Tyr Ala Pro Glu Ala Thr Asp Tyr Asp Val
            405                 410                 415

Arg Val Leu Leu Arg Phe Pro Gln Arg Val Lys Asn Gln Gly Thr Ala
        420                 425                 430

Asp Phe Leu Pro Asn Arg Pro Arg His Thr Trp Glu Trp His Ser Cys
        435                 440                 445

His Gln His Tyr His Ser Met Asp Glu Phe Ser His Tyr Asp Leu Leu
    450                 455                 460

Asp Ala Ala Thr Gly Lys Lys Val Ala Glu Gly His Lys Ala Ser Phe
465                 470                 475                 480

Cys Leu Glu Asp Ser Thr Cys Asp Phe Gly Asn Leu Lys Arg Tyr Ala
            485                 490                 495

Cys Thr Ser His Thr Gln Gly Leu Ser Pro Gly Cys Tyr Asp Thr Tyr
            500                 505                 510

Asn Ala Asp Ile Asp Cys Gln Trp Ile Asp Ile Thr Asp Val Gln Pro
            515                 520                 525

Gly Asn Tyr Ile Leu Lys Val His Val Asn Pro Lys Tyr Ile Val Leu
        530                 535                 540

Glu Ser Asp Phe Thr Asn Asn Val Val Arg Cys Asn Ile His Tyr Thr
545                 550                 555                 560

Gly Arg Tyr Val Ser Ala Thr Asn Cys Lys Ile Val Gln Ser
            565                 570
```

<210> SEQ ID NO 7
<211> LENGTH: 1254
<212> TYPE: DNA
<213> ORGANISM: Homo sapiens

<400> SEQUENCE: 7

```
atgcgcttcg cctggaccgt gctcctgctc gggcctttgc agctctgcgc gctagtgcac    60
tgcgcccctc ccgccgccgg ccaacagcag ccccgcgcg agccgccggc ggctccgggc    120
gcctggcgcc agcagatcca atgggagaac aacgggcagg tgttcagctt gctgagcctg   180
ggctcacagt accagcctca cgccgccgg gaccccgggcg ccgccgtccc tggtgcagcc    240
aacgcctccg cccagcagcc ccgcactccg atcctgctga tccgcgacaa ccgcaccgcc    300
gcggcgcgaa cgcggacggc cggctcatct ggagtcaccg ctggccgccc caggcccacc    360
gcccgtcact ggttccaagc tggctactcg acatctagag cccgcgaagc tggcgcctcg    420
cgcgcggaga accagacagc gccgggagaa gttcctgcgc tcagtaacct gcggccgccc    480
agccgcgtgg acggcatggt gggcgacgac ccttacaacc cctacaagta ctctgacgac    540
aacccttatt acaactacta cgatacttat gaaaggccca gacctggggg caggtaccgg    600
cccggatacg gcactggcta cttccagtac ggtctcccag acctggtggc cgacccctac    660
tacatccagg cgtccacgta cgtgcagaag atgtccatgt acaacctgag atgcgcggcg    720
gaggaaaact gtctggccag tacagcatac agggcagatg tcagagatta tgatcacagg    780
gtgctgctca gattttcccca aagagtgaaa aaccaaggga catcagattt cttacccagc    840
cgaccaagat attcctggga atggcacagt tgtcatcaac attaccacag tatggatgag    900
tttagccact atgacctgct tgatgccaac acccagagga gtggctga aggccacaaa    960
gcaagtttct gtcttgaaga cacatccctgt gactatggct accacaggcg atttgcatgt    1020
actgcacaca cacagggatt gagtcctggc tgttatgata cctatggtgc agacatagac    1080
tgccagtgga ttgatattac agatgtaaaa cctggaaact atatcctaaa ggtcagtgta    1140
```

```
aaccccagct acctggttcc tgaatctgac tataccaaca atgttgtgcg ctgtgacatt    1200
cgctacacag acatcatgc gtatgcctca ggctgcacaa tttcaccgta ttag           1254
```

<210> SEQ ID NO 8
<211> LENGTH: 417
<212> TYPE: PRT
<213> ORGANISM: Homo sapiens

<400> SEQUENCE: 8

```
Met Arg Phe Ala Trp Thr Val Leu Leu Gly Pro Leu Gln Leu Cys
1               5                   10                  15

Ala Leu Val His Cys Ala Pro Ala Ala Gly Gln Gln Gln Pro Pro
                20                  25                  30

Arg Glu Pro Pro Ala Ala Pro Gly Ala Trp Arg Gln Gln Ile Gln Trp
                35                      40                  45

Glu Asn Asn Gly Gln Val Phe Ser Leu Leu Ser Leu Gly Ser Gln Tyr
                50                  55                  60

Gln Pro Gln Arg Arg Arg Asp Pro Gly Ala Ala Val Pro Gly Ala Ala
65                  70                  75                  80

Asn Ala Ser Ala Gln Gln Pro Arg Thr Pro Ile Leu Leu Ile Arg Asp
                85                  90                  95

Asn Arg Thr Ala Ala Ala Arg Thr Arg Thr Ala Gly Ser Ser Gly Val
                100                 105                 110

Thr Ala Gly Arg Pro Arg Pro Thr Ala Arg His Trp Phe Gln Ala Gly
                115                 120                 125

Tyr Ser Thr Ser Arg Ala Arg Glu Ala Gly Ala Ser Arg Ala Glu Asn
                130                 135                 140

Gln Thr Ala Pro Gly Glu Val Pro Ala Leu Ser Asn Leu Arg Pro Pro
145                 150                 155                 160

Ser Arg Val Asp Gly Met Val Gly Asp Pro Tyr Asn Pro Tyr Lys
                165                 170                 175

Tyr Ser Asp Asp Asn Pro Tyr Tyr Asn Tyr Tyr Asp Thr Tyr Glu Arg
                180                 185                 190

Pro Arg Pro Gly Gly Arg Tyr Arg Pro Gly Tyr Gly Thr Gly Tyr Phe
                195                 200                 205

Gln Tyr Gly Leu Pro Asp Leu Val Ala Asp Pro Tyr Tyr Ile Gln Ala
                210                 215                 220

Ser Thr Tyr Val Gln Lys Met Ser Met Tyr Asn Leu Arg Cys Ala Ala
225                 230                 235                 240

Glu Glu Asn Cys Leu Ala Ser Thr Ala Tyr Arg Ala Asp Val Arg Asp
                245                 250                 255

Tyr Asp His Arg Val Leu Leu Arg Phe Pro Gln Arg Val Lys Asn Gln
                260                 265                 270

Gly Thr Ser Asp Phe Leu Pro Ser Arg Pro Arg Tyr Ser Trp Glu Trp
                275                 280                 285

His Ser Cys His Gln His Tyr His Ser Met Asp Glu Phe Ser His Tyr
                290                 295                 300

Asp Leu Leu Asp Ala Asn Thr Gln Arg Arg Val Ala Glu Gly His Lys
305                 310                 315                 320

Ala Ser Phe Cys Leu Glu Asp Thr Ser Cys Asp Tyr Gly Tyr His Arg
                325                 330                 335

Arg Phe Ala Cys Thr Ala His Thr Gln Gly Leu Ser Pro Gly Cys Tyr
                340                 345                 350
```

```
Asp Thr Tyr Gly Ala Asp Ile Asp Cys Gln Trp Ile Asp Ile Thr Asp
            355                 360                 365
Val Lys Pro Gly Asn Tyr Ile Leu Lys Val Ser Val Asn Pro Ser Tyr
    370                 375                 380
Leu Val Pro Glu Ser Asp Tyr Thr Asn Asn Val Val Arg Cys Asp Ile
385                 390                 395                 400
Arg Tyr Thr Gly His His Ala Tyr Ala Ser Gly Cys Thr Ile Ser Pro
                    405                 410                 415
Tyr

<210> SEQ ID NO 9
<211> LENGTH: 752
<212> TYPE: PRT
<213> ORGANISM: Homo sapiens

<400> SEQUENCE: 9

Met Arg Pro Val Ser Val Trp Gln Trp Ser Pro Trp Gly Leu Leu Leu
1               5                   10                  15
Cys Leu Leu Cys Ser Ser Cys Leu Gly Ser Pro Ser Pro Ser Thr Gly
                20                  25                  30
Pro Glu Lys Lys Ala Gly Ser Gln Gly Leu Arg Phe Arg Leu Ala Gly
            35                  40                  45
Phe Pro Arg Lys Pro Tyr Glu Gly Arg Val Glu Ile Gln Arg Ala Gly
    50                  55                  60
Glu Trp Gly Thr Ile Cys Asp Asp Phe Thr Leu Gln Ala Ala His
65                  70                  75                  80
Ile Leu Cys Arg Glu Leu Gly Phe Thr Glu Ala Thr Gly Trp Thr His
                85                  90                  95
Ser Ala Lys Tyr Gly Pro Gly Thr Gly Arg Ile Trp Leu Asp Asn Leu
            100                 105                 110
Ser Cys Ser Gly Thr Glu Gln Ser Val Thr Glu Cys Ala Ser Arg Gly
    115                 120                 125
Trp Gly Asn Ser Asp Cys Thr His Asp Glu Asp Ala Gly Val Ile Cys
130                 135                 140
Lys Asp Gln Arg Leu Pro Gly Phe Ser Asp Ser Asn Val Ile Glu Val
145                 150                 155                 160
Glu His His Leu Gln Val Glu Val Arg Ile Arg Pro Ala Val Gly
                165                 170                 175
Trp Gly Arg Arg Pro Leu Pro Val Thr Glu Gly Leu Val Glu Val Arg
            180                 185                 190
Leu Pro Asp Gly Trp Ser Gln Val Cys Asp Lys Gly Trp Ser Ala His
    195                 200                 205
Asn Ser His Val Val Cys Gly Met Leu Gly Phe Pro Ser Glu Lys Arg
210                 215                 220
Val Asn Ala Ala Phe Tyr Arg Leu Leu Ala Gln Arg Gln His Ser
225                 230                 235                 240
Phe Gly Leu His Gly Val Ala Cys Val Gly Thr Glu Ala His Leu Ser
                245                 250                 255
Leu Cys Ser Leu Glu Phe Tyr Arg Ala Asn Asp Thr Ala Arg Cys Pro
            260                 265                 270
Gly Gly Gly Pro Ala Val Val Ser Cys Val Pro Gly Pro Val Tyr Ala
    275                 280                 285
Ala Ser Ser Gly Gln Lys Lys Gln Gln Gln Ser Lys Pro Gln Gly Glu
290                 295                 300
```

```
Ala Arg Val Arg Leu Lys Gly Gly Ala His Pro Gly Glu Gly Arg Val
305                 310                 315                 320

Glu Val Leu Lys Ala Ser Thr Trp Gly Thr Val Cys Asp Arg Lys Trp
            325                 330                 335

Asp Leu His Ala Ala Ser Val Val Cys Arg Glu Leu Gly Phe Gly Ser
        340                 345                 350

Ala Arg Glu Ala Leu Ser Gly Ala Arg Met Gly Gln Gly Met Gly Ala
    355                 360                 365

Ile His Leu Ser Glu Val Arg Cys Ser Gly Gln Glu Leu Ser Leu Trp
370                 375                 380

Lys Cys Pro His Lys Asn Ile Thr Ala Glu Asp Cys Ser His Ser Gln
385                 390                 395                 400

Asp Ala Gly Val Arg Cys Asn Leu Pro Tyr Thr Gly Ala Glu Thr Arg
            405                 410                 415

Ile Arg Leu Ser Gly Gly Arg Ser Gln His Glu Gly Arg Val Glu Val
        420                 425                 430

Gln Ile Gly Gly Pro Gly Pro Leu Arg Trp Gly Leu Ile Cys Gly Asp
    435                 440                 445

Asp Trp Gly Thr Leu Glu Ala Met Val Ala Cys Arg Gln Leu Gly Leu
450                 455                 460

Gly Tyr Ala Asn His Gly Leu Gln Glu Thr Trp Tyr Trp Asp Ser Gly
465                 470                 475                 480

Asn Ile Thr Glu Val Val Met Ser Gly Val Arg Cys Thr Gly Thr Glu
            485                 490                 495

Leu Ser Leu Asp Gln Cys Ala His His Gly Thr His Ile Thr Cys Lys
        500                 505                 510

Arg Thr Gly Thr Arg Phe Thr Ala Gly Val Ile Cys Ser Glu Thr Ala
    515                 520                 525

Ser Asp Leu Leu Leu His Ser Ala Leu Val Gln Glu Thr Ala Tyr Ile
530                 535                 540

Glu Asp Arg Pro Leu His Met Leu Tyr Cys Ala Ala Glu Glu Asn Cys
545                 550                 555                 560

Leu Ala Ser Ser Ala Arg Ser Ala Asn Trp Pro Tyr Gly His Arg Arg
            565                 570                 575

Leu Leu Arg Phe Ser Ser Gln Ile His Asn Leu Gly Arg Ala Asp Phe
        580                 585                 590

Arg Pro Lys Ala Gly Arg His Ser Trp Val Trp His Glu Cys His Gly
    595                 600                 605

His Tyr His Ser Met Asp Ile Phe Thr His Tyr Asp Ile Leu Thr Pro
610                 615                 620

Asn Gly Thr Lys Val Ala Glu Gly His Lys Ala Ser Phe Cys Leu Glu
625                 630                 635                 640

Asp Thr Glu Cys Gln Glu Asp Val Ser Lys Arg Tyr Glu Cys Ala Asn
            645                 650                 655

Phe Gly Glu Gln Gly Ile Thr Val Gly Cys Trp Asp Leu Tyr Arg His
        660                 665                 670

Asp Ile Asp Cys Gln Trp Ile Asp Ile Thr Asp Val Lys Pro Gly Asn
    675                 680                 685

Tyr Ile Leu Gln Val Val Ile Asn Pro Asn Phe Glu Val Ala Glu Ser
690                 695                 700

Asp Phe Thr Asn Asn Ala Met Lys Cys Asn Cys Lys Tyr Asp Gly His
705                 710                 715                 720

Arg Ile Trp Val His Asn Cys His Ile Gly Asp Ala Phe Ser Glu Glu
```

```
                       725                 730                 735
Ala Asn Arg Arg Phe Glu Arg Tyr Pro Gly Gln Thr Ser Asn Gln Ile
            740                 745                 750

<210> SEQ ID NO 10
<211> LENGTH: 36
<212> TYPE: DNA
<213> ORGANISM: Artificial sequence
<220> FEATURE:
<223> OTHER INFORMATION: Synthetically constructed single strand DNA
      oligonucleotide

<400> SEQUENCE: 10
cgcaagcttg gatccgggat ggagaggcct ctgtgc                              36

<210> SEQ ID NO 11
<211> LENGTH: 37
<212> TYPE: DNA
<213> ORGANISM: Artificial sequence
<220> FEATURE:
<223> OTHER INFORMATION: Synthetically constructed single strand DNA
      oligonucleotide

<400> SEQUENCE: 11
cgctctagag gatccttact gcggggacag ctggttg                             37

<210> SEQ ID NO 12
<211> LENGTH: 21
<212> TYPE: DNA
<213> ORGANISM: Artificial sequence
<220> FEATURE:
<223> OTHER INFORMATION: Synthetically constructed single strand DNA
      oligonucleotide

<400> SEQUENCE: 12
gccatgcgac ctgtcagtgt c                                              21

<210> SEQ ID NO 13
<211> LENGTH: 18
<212> TYPE: DNA
<213> ORGANISM: Artificial sequence
<220> FEATURE:
<223> OTHER INFORMATION: Synthetically constructed single strand DNA
      oligonucleotide

<400> SEQUENCE: 13
gggcagtggc acttagat                                                  18

<210> SEQ ID NO 14
<211> LENGTH: 613
<212> TYPE: DNA
<213> ORGANISM: Homo sapiens

<400> SEQUENCE: 14
ccctgacctg gtcctcaatg cggagatggt gcagcagacc acctacctgg aggaccggcc    60
catgttcatg ctgcagtgtg ccatggagga gaactgcctc tcggcctcag ccgcgcagac   120
cgaccccacc acgggctacc gccggctcct gcgcttctcc tcccagatcc acaacaatgg   180
ccagtccgac ttccggccca gaacggccg ccacgcgtgg atctggcacg actgtcacag    240
gcactaccac agcatggagg tgttcaccca ctatgacctg ctgaacctca atggcaccaa   300
ggtggcagag ggccacaagg ccagcttctg cttggaggac acagaatgtg aaggagacat   360
ccagaagaat tacgagtgtg ccaacttcgg cgatcagggc atcaccatgg gctgctggga   420
```

-continued

```
catgtaccgc catgacatcg actgccagtg ggttgacatc actgacgtgc cccctggaga      480
ctacctgttc caggttgtta ttaaccccaa cttcgaggtt gcagaatccg attactccaa      540
caacatcatg aaatgcagga gccgctatga cggccaccgc atctggatgt acaactgcca      600
cataggtggt tcc                                                          613
```

```
<210> SEQ ID NO 15
<211> LENGTH: 30
<212> TYPE: DNA
<213> ORGANISM: Artificial sequence
<220> FEATURE:
<223> OTHER INFORMATION: Synthetically constructed single strand DNA
      oligonucleotide

<400> SEQUENCE: 15
acatgcatgc cctgacctgg tcctcaatgc                                        30

<210> SEQ ID NO 16
<211> LENGTH: 30
<212> TYPE: DNA
<213> ORGANISM: Artificial sequence
<220> FEATURE:
<223> OTHER INFORMATION: Synthetically constructed single strand DNA
      oligonucleotide

<400> SEQUENCE: 16
cccaagcttg gaaccaccta tgtggcagtt                                        30

<210> SEQ ID NO 17
<211> LENGTH: 210
<212> TYPE: PRT
<213> ORGANISM: Artificial sequence
<220> FEATURE:
<223> OTHER INFORMATION: Synthetically constructed protein sequence
      derived from fusion of LOR-1 fragment (1641-2253) to a 5' 6XHis
      tag

<400> SEQUENCE: 17
```

```
His His His His His His Pro Asp Leu Val Leu Asn Ala Glu Met Val
1               5                   10                  15

Gln Gln Thr Thr Tyr Leu Glu Asp Arg Pro Met Phe Met Leu Gln Cys
            20                  25                  30

Ala Met Glu Glu Asn Cys Leu Ser Ala Ser Ala Gln Thr Asp Pro
        35                  40                  45

Thr Thr Gly Tyr Arg Arg Leu Leu Arg Phe Ser Ser Gln Ile His Asn
    50                  55                  60

Asn Gly Gln Ser Asp Phe Arg Pro Lys Asn Gly Arg His Ala Trp Ile
65                  70                  75                  80

Trp His Asp Cys His Arg His Tyr His Ser Met Glu Val Phe Thr His
                85                  90                  95

Tyr Asp Leu Leu Asn Leu Asn Gly Thr Lys Val Ala Glu Gly His Lys
            100                 105                 110

Ala Ser Phe Cys Leu Glu Asp Thr Glu Cys Glu Gly Asp Ile Gln Lys
        115                 120                 125

Asn Tyr Glu Cys Ala Asn Phe Gly Asp Gln Gly Ile Thr Met Gly Cys
    130                 135                 140

Trp Asp Met Tyr Arg His Asp Ile Asp Cys Gln Trp Val Asp Ile Thr
145                 150                 155                 160

Asp Val Pro Pro Gly Asp Tyr Leu Phe Gln Val Val Ile Asn Pro Asn
                165                 170                 175
```

```
Phe Glu Val Ala Glu Ser Asp Tyr Ser Asn Asn Ile Met Lys Cys Arg
            180                 185                 190

Ser Arg Tyr Asp Gly His Arg Ile Trp Met Tyr Asn Cys His Ile Gly
        195                 200                 205

Gly Ser
    210

<210> SEQ ID NO 18
<211> LENGTH: 660
<212> TYPE: DNA
<213> ORGANISM: Artificial sequence
<220> FEATURE:
<223> OTHER INFORMATION: Synthetically constructed Northern blot probe
      consisting of Nucleotides 1-660 of the LOR-1 cDNA

<400> SEQUENCE: 18
atggagaggc ctctgtgctc ccacctctgc agctgcctgg ctatgctggc cctcctgtcc       60
cccctgagcc tggcacagta tgacagctgg ccccattacc ccgagtactt ccagcaaccg      120
gctcctgagt atcaccagcc ccaggccccc gccaacgtgg ccaagattca gctgcgcctg      180
gctgggcaga agaggaagca cagcgagggc cgggtggagg tgtactatga tggccagtgg      240
ggcaccgtgt gcgatgacga cttctccatc cacgctgccc acgtcgtctg ccgggagctg      300
ggctatgtgg aggccaagtc ctggactgcc agctcctcct acggcaaggg agaagggccc      360
atctggttag acaatctcca ctgtactggc aacgaggcga cccttgcagc atgcacctcc      420
aatggctggg gcgtcactga ctgcaagcac acggaggatg tcggtgtggt gtgcagcgac      480
aaaaggattc ctgggttcaa atttgacaat tcgttgatca accagataga gaacctgaat      540
atccaggtgg aggacattcg gattcgagcc atcctctcaa cctaccgcaa gcgcacccca      600
gtgatggagg gctacgtgga ggtgaaggag ggcaagacct ggaagcagat ctgtgacaag      660

<210> SEQ ID NO 19
<211> LENGTH: 530
<212> TYPE: DNA
<213> ORGANISM: Artificial sequence
<220> FEATURE:
<223> OTHER INFORMATION: Synthetically constructed Northern blot probe
      consisting of nucleotides 1061-1590 of the LOR-2 cDNA

<400> SEQUENCE: 19
gagaagctct gagtggcgct cgcatggggc agggcatggg tgctatccac ctgagtgaag       60
ttcgctgctc tggacaggag ctctccctct ggaagtgccc ccacaagaac atcacagctg      120
aggattgttc acatagccag gatgccgggg tccggtgcaa cctaccttac actggggcag      180
agaccaggat ccgactcagt gggggccgca gccaacatga ggggcgagtc gaggtgcaaa      240 taggggacc tgggcccctt cgctgggggcc tcatctgtgg ggatgactgg ggaccctgg       300 aggccatggt ggcctgtagg caactgggtc tgggctacgc caaccacggc tgcaggaga       360 cctggtactg ggactctggg aatataacag aggtggtgat gagtggagtg cgctgcacag      420
ggactgagct gtccctggat cagtgtgccc atcatggcac ccacatcacc tgcaagagga      480
cagggacccg cttcactgct ggagtcatct gttctgagac tgcatcagat                 530
```